US010016414B2

(12) United States Patent
Morabito et al.

(10) Patent No.: US 10,016,414 B2
(45) Date of Patent: Jul. 10, 2018

(54) MODULATION OF UBIQUITINATION OF SYNAPTIC PROTEINS FOR THE TREATMENT OF NEURODEGENERATIVE AND PSYCHIATRIC DISORDERS

(75) Inventors: Maria Morabito, Boston, MA (US); Michael Bianchetta, Roslindale, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 310 days.

(21) Appl. No.: 13/884,705

(22) PCT Filed: Nov. 14, 2011

(86) PCT No.: PCT/US2011/060650
§ 371 (c)(1),
(2), (4) Date: Aug. 28, 2013

(87) PCT Pub. No.: WO2012/065182
PCT Pub. Date: May 18, 2012

(65) Prior Publication Data
US 2013/0331398 A1    Dec. 12, 2013

Related U.S. Application Data

(60) Provisional application No. 61/413,187, filed on Nov. 12, 2010.

(51) Int. Cl.
| *A61K 31/496* | (2006.01) |
| *A61K 31/519* | (2006.01) |
| *A61K 31/00* | (2006.01) |
| *A61K 31/155* | (2006.01) |
| *A61K 31/381* | (2006.01) |
| *A61K 31/4035* | (2006.01) |
| *A61K 31/4155* | (2006.01) |
| *A61K 31/4164* | (2006.01) |
| *A61K 31/435* | (2006.01) |
| *A61K 31/4439* | (2006.01) |
| *A61K 31/4709* | (2006.01) |
| *A61K 31/5513* | (2006.01) |

(52) U.S. Cl.
CPC ............ *A61K 31/496* (2013.01); *A61K 31/00* (2013.01); *A61K 31/155* (2013.01); *A61K 31/381* (2013.01); *A61K 31/4035* (2013.01); *A61K 31/4155* (2013.01); *A61K 31/4164* (2013.01); *A61K 31/435* (2013.01); *A61K 31/4439* (2013.01); *A61K 31/4709* (2013.01); *A61K 31/519* (2013.01); *A61K 31/5513* (2013.01)

(58) Field of Classification Search
CPC .... A61K 31/00; A61K 31/155; A61K 31/381; A61K 31/4035; A61K 31/4155; A61K 31/4164; A61K 31/435; A61K 31/4439; A61K 31/4709; A61K 31/496; A61K 31/519; A61K 31/5513
See application file for complete search history.

(56) References Cited

U.S. PATENT DOCUMENTS

2003/0105152 A1*  6/2003  Ingram et al. ............... 514/417
2012/0283269 A1* 11/2012  Blagosklonny et al.  514/254.07

OTHER PUBLICATIONS

Ortega, (Cerebral Cortex, Sep. 2010, 2132-2144).*
Uo et al. (The J of Neurosci, Nov. 7, 2007, 27(45),12198-12210).*
Kim et al. (J Neurosci. 2008, 26, 28(48), 12604-12613).*

* cited by examiner

*Primary Examiner* — Umamaheswari Ramachandran
(74) *Attorney, Agent, or Firm* — Lathrop Gage LLP; James H. Velema, Esq.

(57) ABSTRACT

The instant invention is based, at least in part, on a newly-identified proteasome-independent signaling function of ubiquitinated PSD-95. Mdm2 inhibitors, Mdm4 inhibitors, PSD-95 inhibitors, and/or enantiomers and/or derivatives thereof decrease endocytosis via preventing PSD-95 ubiquitination, and thereby increase AMPAR, NMDAR, D1 dopamine receptor surface expression in response to a given stimulus (e.g., NMDA, Aβ). Accordingly, the invention provides methods for modulating AMPARs, NMDARs, or D1 dopamine receptors in a neuronal cell by contacting the neuronal cell with an Mdm2 and/or Mdm4 inhibitor or PSD-95 inhibitor and/or enantiomers and/or derivatives thereof. Mdm2 and/or Mdm4 inhibitors decrease the enzymatic activity of the respective proteins, and/or interactions with their respective substrates. Mdm2 and Mdm4 inhibitors and/or PSD-95 inhibitors of the invention are contemplated for use in the treatment of neurological disorders, neurodevelopmental disorders, and psychiatric disorders. The invention also provides methods to screen for new Mdm2 and Mdm4 inhibitors and PSD-95 inhibitors and/or enantiomers and/or derivatives thereof.

5 Claims, 8 Drawing Sheets

A

B

C

D

A

B

A

B

A

B

MODULATION OF UBIQUITINATION OF SYNAPTIC PROTEINS FOR THE TREATMENT OF NEURODEGENERATIVE AND PSYCHIATRIC DISORDERS

RELATED APPLICATIONS

This application is a 35 U.S.C. 371 national stage filing of International Application No. PCT/US2011/060650 filed Nov. 14, 2011, which claims the benefit of U.S. Provisional Patent Application No. 61/413,187, filed Nov. 12, 2010, the entire contents of which are herein incorporated by reference.

GOVERNMENT LICENSE RIGHTS

This invention was made with government support under Grant No. R01DA019451 awarded by the National Institutes of Health. The government has certain rights in the invention.

BACKGROUND OF THE INVENTION

Ubiquitination of postsynaptic proteins is critical for learning and memory (Ehlers, 2003) and has been implicated in remodeling of synaptic networks in brain development, synaptic function, and brain disorders (Mabb and Ehlers, 2010). Ubiquitination is a regulated post-translational modification that conjugates ubiquitin moieties to lysine residues of target proteins via the sequential actions of an ubiquitin-activating enzyme (E1), an ubiquitin-conjugating enzyme (E2), and an ubiquitin ligase (E3) (Pickart, 2001). While polyubiquitination functions in targeting proteins for degradation by the proteasome, monoubiquitination functions in non-proteasomal signaling, including endocytosis and vesicular trafficking (Mukhopadhyay and Riezman, 2007). While Colledge et al. (2003) published that PSD-95 is ubiquitinated and rapidly removed from synaptic sites by proteasome-dependent degradation, ubiquitination independent of proteasome function has been implicated in N-Methyl-D-aspartic acid (NMDA) receptor (NMDAR)-induced α-amino-3-hydroxy-5-methyl-4-isoxazolepropionic acid receptor (AMPA) receptor (AMPAR) endocytosis and long-term depression (LTD) (Citri et al., 2009).

Postsynaptic density protein 95 (PSD-95) (synapse-associated protein 90(SAP90)) is a major postsynaptic scaffolding protein of glutamatergic synapses implicated in synaptic maturation and regulation of synaptic strength and plasticity (El-Husseini et al., 2000; Kim & Sheng, 2004; Funke et al., 2005; Elias & Nicoll, 2007). PSD-95 associates with AMPARs via its interaction with transmembrane AMPAR regulatory proteins (TARPs) (Chen et al., 2000; Schnell et al., 2002) and determines the synaptic density of AMPARs (Bats et al., 2007; Elias & Nicoll, 2007; Payne, 2008). Overexpression of PSD-95 enhances the surface expression of AMPARs (E1-Husseini et al., 2000; Schnell et al., 2002; Beique & Andrade, 2003), occludes long-term potentiation (LTP) (Stein et al., 2003; Ehrlich & Malinow, 2004), and enhances LTD (Stein et al., 2003). Knocking out (or down) PSD-95 and its family members decreases the synaptic levels of AMPARs (Beique et al., 2006; Elias et al., 2006), and PSD-95 knockdown inhibits NMDAR-induced endocytosis of synaptic AMPARs (Bhattacharyya et al., 2009) and impairs LTD (Xu et al., 2008).

PSD-95 is ubiquitinated by the E3 Ubiquitin Ligase murine double minute (Mdm)2 (also known as human double minute (Hdm)2), and the rapid and transient ubiquitination of PSD-95 has been implicated in NMDAR-induced AMPAR endocytosis by a mechanism involving proteasome degradation of ubiquitinated PSD-95 (Colledge et al., 2003). Since ubiquitination of PSD-95 is not easily detectable (Ehlers, 2003; Bingol & Schuman, 2004) and occurs transiently (Colledge et al., 2003; Mabb and Ehlers, 2010), it has not been clear whether PSD-95 is polyubiquitinated or monoubiquitinated (Colledge et al., 2003). Ubiquitination of PSD-95 requires the PEST motif (Rechsteiner and Rogers, 1996) within the N-terminus of PSD-95 (Colledge et al., 2003), proximal to the residues phosphorylated by cyclin-dependent kinase (Cdk)5 (Morabito et al., 2004). Cdk5 is a proline-directed serine/threonine kinase inactivated by NMDAR stimulation (Wei et al., 2005) that is implicated in synaptic plasticity, learning and memory, and in many disorders including drug addiction and neurodegenerative diseases such as Alzheimer's (Ohshima et al., 2005; Angelo et al., 2006; Cheung et al., 2006; Hawasli and Bibb, 2007; Lai 3 and Ip, 2009). The importance of Cdk5 in synaptic plasticity is underscored by the enhancement of LTP in conditional Cdk5 knockout mice (Hawasli et al., 2007) and the lower threshold for LTP induction (Wei et al., 2005) and impaired LTD (Ohshima et al., 2005) in mice with a deletion for the Cdk5 regulatory subunit p35.

SUMMARY OF THE INVENTION

The present invention is based, at least in part, on the discovery and characterization of a non-proteasomal signaling function of ubiquitinated PSD-95. Consequently, a direct function for PSD-95 monoubiquitination in the recruitment of the AMPAR/PSD-95 complex to the endocytic apparatus is likely. It is demonstrated herein that ubiquitination of PSD-95 is increased in p35 knockout mice, as well as in neurons in which Cdk5 activity has been inhibited pharmacologically. PSD-95 is shown herein to be monoubiquitinated on multiple lysines and, importantly, this posttranslational modification does not affect PSD-95 protein levels in vivo. It is further shown herein that monoubiquitination of PSD-95 correlates with increased interaction of PSD-95 with the β-adaptin subunit of the clathrin adaptor protein (AP) complexes, that both PSD-95 ubiquitination and interaction with β-adaptin are induced by NMDAR activity, and that Mdm2 is required for the NMDAR-induced interaction of PSD-95 with β-adaptin. Thus, these results intimate a non-proteolytic mechanism by which ubiquitinated PSD-95 regulates the endocytosis of AMPARs in response to NMDAR stimulation, and possibly other aspects of synaptic remodeling.

The invention is based, at least in part, on the finding that Mdm2-dependent ubiquitination of PSD-95 regulates PSD-95 interaction with β-adaptin, a component of the clathrin complex, and thus regulates AMPA receptor endocytosis. Based on this finding, the invention features the inhibition of Hdm2/Mdm2 prevents AMPA receptor endocytosis by decreasing the association of AMPA receptor/PSD-95 complex with the clathrin endocytic complex and provides a mechanism, using Hdm2/Mdm2 and Mdm4/MdmX inhibitors, for the treatment of neurodegenerative and psychiatric disorders in which cell surface expression of AMPA receptors is beneficial. Inhibition of binding of Hdm2/Mdm2 to substrates, in particular, PSD-95 (e.g., using binding inhibitory compounds), is an exemplary aspect of the invention, particularly suited to the treatment of, for example, neurodegenerative and psychiatric disorders involving aberrant cell surface expression of AMPA receptors.

The neurodegenerative disease market is a multibillion dollar market in the United States. While disease-modifying drugs for the treatment of, e.g., Alzheimer's Disease (AD), exist, they have limited medical benefit. Inhibitors of Hdm2/Mdm2 activity may be useful and beneficial for the treatment of early stage AD, which is characterized by cognitive impairment and memory loss. Glutamate receptors are also involved in many psychiatric disorders. Accordingly, this invention has the potential to be used for the treatment of disorders in which the cell surface expression of AMPA receptors (and possibly other receptors associated with PSD-95 or related membrane-associated guanylate kinase (MAGUK) proteins such as SAP97, SAP102, PSD93) is altered. In particular, the skilled artisan will appreciate that NMDA receptor and D1 dopamine receptors bind directly to PSD-95, and thus are particular targets for cell surface expression alteration according to the methods of the invention. In fact, in addition to binding PSD-95 (Niethammer et al., 1996), NMDA receptor subunits GluN1, GluN2A, and GluN2B interact with clathrin adaptor proteins (Lavezzari et al., 2004; Scott et al., 2004). PSD-95 also binds D1 dopamine receptors, and this interaction promotes D1 receptor endocytosis (Zhang et al., 2007).

In one aspect, the invention provides a method of modulating AMPAR, NMDAR, D1 dopamine receptor, or a combination thereof; modulating surface levels of AMPAR, NMDAR, D1 dopamine receptor, or a combination thereof; modulating synaptic plasticity of a neuronal cell in a neuronal cell comprising contacting the neuronal cell with a compound, wherein the compound is an Mdm2 inhibitor, an Mdm4 inhibitor, a PSD-95 inhibitor, and/or enantiomers and/or derivatives thereof, or a combination thereof, such that Mdm2 activity, Mdm4 activity, Mdm2 association with a substrate, Mdm4 association with a substrate, or association between PSD-95 and its interacting proteins, or a combination thereof, is inhibited, thereby modulating AMPAR, NMDAR, D1 dopamine receptor, or the combination thereof, in the neuronal cell. Such substrates can be, e.g., PSD-95, a non-PSD-95 MAGUK family protein (e.g., SAP97, SAP102, and PSD-93), a PSD-95-associated protein, and other synaptic or non-synaptic proteins that interact with Mdm2 and/or Mdm4.

In yet another aspect, the invention provides a method for inhibiting the activity of Mdm2 and/or Mdm4, and/or Mdm2 and/or Mdm4 association with a substrate for the treatment of neurological disorders, neurodevelopmental disorders, and psychiatric disorders. Substrates can be, e.g., PSD-95, a non-PSD-95 MAGUK family protein (e.g., SAP97, SAP102, and PSD-93), a PSD-95-associated protein, and other synaptic or non-synaptic proteins that interact with Mdm2 and/or Mdm4. In some embodiments, the compound inhibits ubiquitination or other post-translational modification of a non-PSD-95 membrane-associated guanylate kinase (MAGUK) protein such as SAP97, SAP102, PSD-93, or other related MAGUK protein.

In another aspect, the invention provides a method of improving cognitive impairment or memory loss comprising administration of a therapeutically effective dose of benzodiazepinediones and/or enantiomers and/or derivatives thereof, isoindoline compounds and/or enantiomers and/or derivatives thereof (e.g., those described in US 2011/0224274, which is hereby incorporated by reference in its entirety), cis-imidazolines and/or enantiomers and/or derivatives thereof, benzoylthioureas and/or enantiomers and/or derivatives thereof, spiro-oxindoles and/or enantiomers and/or derivatives thereof, thiophenes and/or enantiomers and/or derivatives thereof, arylsulfonamides and/or enantiomers and/or derivatives thereof, bisarylureas and/or enantiomers and/or derivatives thereof, acylimidazolones and/or enantiomers and/or derivatives thereof, deazaflavins and/or enantiomers and/or derivatives thereof, natural products and/or enantiomers and/or derivatives thereof, acridines and/or enantiomers and/or derivatives thereof, JnJ-26854165, PSD-95 inhibitors and/or enantiomers and/or derivatives thereof, or a combination thereof.

In some embodiments, the compound and enantiomer and/or derivative thereof inhibits ubiquitination or other post-translational modification of a non-PSD-95 membrane-associated guanylate kinase (MAGUK) protein such as SAP97, SAP102, PSD-93, or other related MAGUK protein. In other embodiments, the compound is capable of crossing the blood-brain barrier. In one particular embodiment, PSD-95 inhibitors are inhibitory peptides.

In some embodiments, the compounds used in the methods of the invention are benzodiazepinediones and/or enantiomers and/or derivatives thereof (e.g., TDP521252 and TDP665759), cis-imidazolines and/or enantiomers and/or derivatives thereof (e.g., Nutlin-1, Nutlin-2, Nutlin-3, Nutlin-3a), isoindolines and/or enantiomers and/or derivatives thereof, benzoylureas or benzoylthioureas and/or enantiomers and/or derivatives thereof (e.g., tenovin-1), spiro-oxindoles and/or enantiomers and/or derivatives thereof (e.g., MI-43, MI-63, MI-219, and MI-319), thiophenes and/or enantiomers and/or derivatives thereof (e.g., RITA (NSC652287)), JnJ-26854165 (serdemetan) and combinations thereof.

In other embodiments, the methods above are carried out in vivo, wherein modulation of any one of these activities results in treatment of a neurological disorder (cognitive impairment, cognitive dysfunction, Alzheimer's disease, Parkinson's disease, and dementia), a neurodevelopmental disorder (autism spectrum disorders (ASD), fragile-X syndrome, disorders affecting emotion, learning ability, memory, and Down's syndrome), or a psychiatric disorder (schizophrenia, bipolar disorder, major depressive disorder, depression, anxiety disorders, attention-deficit hyperactivity disorder, and substance abuse).

In some embodiments, the compound inhibits enzymatic activity and/or enzyme-substrate interaction and/or PSD-95 binding with interacting proteins and/or post-translational modification of PSD-95. Such compounds are, for example, arylsulfonamides and/or enantiomers and/or derivatives thereof, bisarylureas and/or enantiomers and/or derivatives thereof, acylimidazolones and/or enantiomers and/or derivatives thereof, deazaflavins and/or enantiomers and/or derivatives thereof (e.g., HLI98 and HLI373), natural products and/or enantiomers and/or derivatives thereof (e.g., sempervirine and resveratrol), acridines and/or enantiomers and/or derivatives thereof, JnJ-26854165, and combinations thereof.

In yet another aspect, the invention provides a method of identifying an agent for use in modulating AMPAR, NMDAR, and/or D1 dopamine receptor endocytosis in a neuron, modulating AMPAR, NMDAR, and/or D1 dopamine receptor surface expression in a neuron, and/or modulating synaptic plasticity, comprising contacting an assay composition or neuron which comprises Mdm2, Mdm4, or PSD-95 with a test agent, assaying for inhibition of activity of Mdm2 and/or Mdm4, and/or Mdm2 and/or Mdm4 association with a substrate, PSD-95 binding with an interaction partner, or post-translational modification of PSD-95, wherein an agent that inhibits the activity or association is identified as an agent capable of modulating the AMPAR, NMDAR, and/or D1 dopamine receptor endocytosis;

AMPAR, NMDAR, and/or D1 dopamine receptor surface expression; and/or synaptic plasticity. In some embodiments, Mdm2 and/or Mdm4 activity or association is inhibited, PSD-95 binding with an interaction partner and/or post-translational modification of PSD-95 is inhibited, AMPAR, NMDAR, and/or D1 dopamine receptor endocytosis is prevented, and/or AMPAR, NMDAR, and/or D1 dopamine receptor surface expression is enhanced. In other embodiments, AMPAR, NMDAR, and/or D1 dopamine receptor endocytosis is prevented by decreasing the association of AMPAR, NMDAR, and/or D1 dopamine receptor complexed with PSD-95 and/or non-PSD-95 MAGUK proteins (e.g., SAP97, SAP102, and PSD-93) with clathrin endocytic complex.

In another aspect, the invention provides a method of identifying an agent for use in the treatment of a neurological disorder, neurodevelopmental disorder, and/or psychiatric disorder comprising contacting an assay composition or cell which comprises Mdm2, Mdm4, and/or PSD-95, or biologically active fragments thereof, with a test agent, assaying for modulation of activity (e.g., enzymatic activity, ubiquitin ligase activity) of Mdm2 and/or Mdm4 or Mdm2 and/or Mdm4 association with a substrate, and/or PSD-95 binding with an interaction partner or post-translational modification of PSD-95, wherein an agent that so modulated activity or association is identified as an agent capable of use in the treatment of a neurological disorder, neurodevelopmental disorder, and/or psychiatric disorder. In some embodiments, the cell is a neuron. In other embodiments, the cell or assay composition comprises a membrane-associated guanylate kinase (MAGUK) protein (e.g., PSD-95, SAP97, SAP102, PSD-93) or biologically active portion thereof, and the activity assayed is inhibition of the interaction of Mdm2 and/or Mdm4 with its substrate MAGUK. In some embodiments, the activity is Mdm2-dependent ubiquitination of PSD-95, SAP97, SAP102, and/or PSD-93. In other embodiments, Mdm2 and/or Mdm4 activity further regulates interaction of a post-synaptic scaffolding protein and/or other synaptic protein with clathrin endocytic complex, and/or further regulates interaction of a post-synaptic scaffolding protein (e.g., PSD-95) with the AP-2 complex, including with beta-adaptin. In some embodiments, the agent is formulated in a pharmaceutical composition.

In some embodiments of the methods of the invention, ubiquitin signaling functions (e.g., intracellular trafficking of proteins, protein degradation, and/or receptor endocytosis) are modulated.

A. Immunoblot showing that p35 knockout mice have increased PSD-95 ubiquitination. PSD-95 immunoprecipitated from brain lysates of p35 knockout (−/−) and wild-type (+/+) mice revealed discrete bands representing increased PSD-95 ubiquitination in p35 knockout mice. Quantification (mean±SEM) revealed that ubiquitination of PSD-95 was increased to 431.3%±84.4% versus wild-type 100%±18.5%; n=3; *, p<0.05. The ubiquitin immunoreactivity was normalized to the level of immunoprecipitated PSD-95 and expressed as a percentage of wildtype control.

B. Immunoblot showing that roscovitine treatment increases PSD-95 ubiquitination. Acute mouse forebrain slices were treated with the specific Cdk5 inhibitor roscovitine (10 μM, 45 min), or dimethyl sulfoxide (DMSO) as control. PSD-95 immunoprecipitated from lysates of the treated slices revealed increased ubiquitination of PSD-95 in roscovitine-treated (R) slices relative to control (D), with a pattern of discrete bands similar to that obtained in p35 knockout mice. Quantification (mean±SEM) revealed that ubiquitination of PSD-95 was increased to 274.6%±71.6% versus 100%±54.5% in untreated control slices; n=4; *, p<0.01. The ubiquitin immunoreactivity was normalized to the level of immunoprecipitated PSD-95 and expressed as a percentage of DMSO control.

C. A schematic view of PSD-95 domain structure with ubiquitinated lysines (K). PSD-95 is ubiquitinated on multiple lysines. Lysine residues ubiquitinated are K10 in the N terminus, K403 in the linker between the PDZ3 and SH3 domains, and K544, K672, and K679 in the GK domain.

Figure 2:
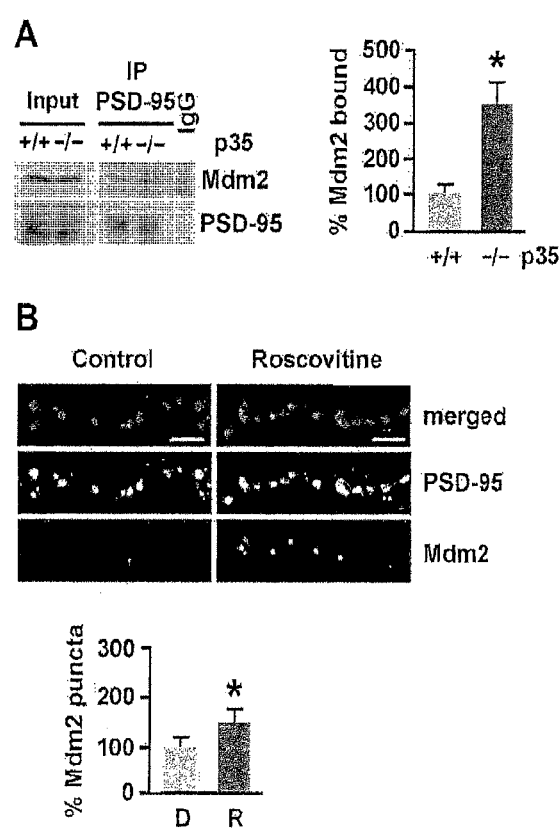

FIG. 2. Reduced Cdk5 activity increases the interaction of the Ubiquitin E3 Ligase Mdm2 with PSD-95

A. Immunoblot showing that p35 knockout mice have increased interaction of PSD-95 with Mdm2. PSD-95 immunoprecipitated from brain lysates of p35 knockout (−/−) and wild-type (+/+) mice revealed increased coimmunoprecipitation of Mdm2 with PSD-95 in p35 knockout mice. Quantification (mean±SEM) revealed that the interaction of Mdm2 with PSD-95 was increased to 360.5%±65.6% versus wild-type 100%±20.6%; n=3; *, p<0.05. Mdm2 immunoreactivity was normalized to the level of immunoprecipitated PSD-95 and expressed as a percentage of wild-type control. IgG: control immunoprecipitation with mouse IgG.

B. Micrograph showing that roscovitine treatment of cultured hippocampal neurons increases the colocalization of Mdm2 with PSD-95. Cultured hippocampal neurons were treated with roscovitine (10 μM, 45 min) or DMSO as control, and immunostained with antibodies against Mdm2 and PSD-95. Representative confocal images from each condition are shown; Mdm2 (green) and PSD-95 (red) (scale bars, 10 μm). Quantification (mean±SEM) revealed that in roscovitine-treated cultures (R) the percentage of puncta positive for both PSD-95 and Mdm2 was increased to 149%±27.4% versus 100%±24.8% in control DMSO cultures (D); n=4, *, p<0.05. The number of costained puncta, as a percentage of total PSD-95 puncta, are expressed as a percentage of the number for DMSO controls.

Figure 3:
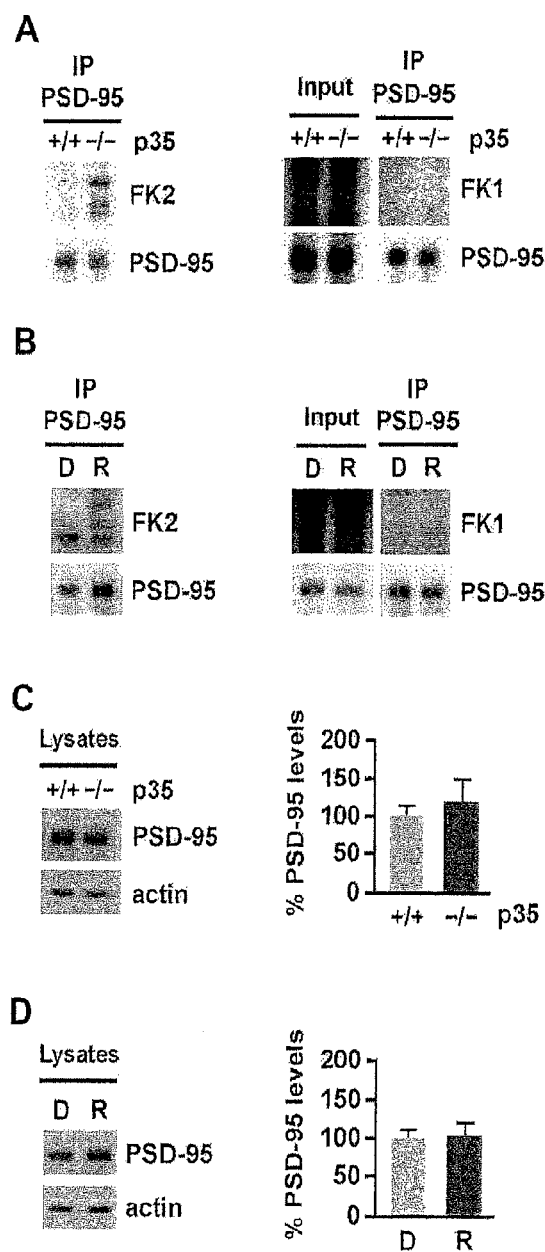

FIG. 3. Monoubiquitination of PSD-95 does not alter PSD-95 protein levels

A. Immunoblot showing that PSD-95 is monoubiquitinated on multiple sites in p35 knockout mice. PSD-95 immunoprecipitated from brain lysates of p35 knockout (−/−) and wild-type (+/+) mice immunoblotted with the FK2 antibody, which recognizes monoubiquitin-conjugated proteins, revealed ubiquitination of PSD-95 in p35 knockout, with a pattern of discrete bands. Immunoblot with the FK1 antibody, which recognizes only polyubiquitin-conjugated proteins, did not reveal immunoreactive bands (right panel). Staining of polyubiquitinated proteins in the input is a positive control for FK1 blotting.

B. Immunoblot showing that roscovitine treatment increases PSD-95 monoubiquitination on multiple lysines. Acute mouse forebrain slices were treated with the specific Cdk5 inhibitor roscovitine (R) (10 μM, 45 min), or DMSO (D) as control. Immunoblots of PSD-95 immunoprecipitated from lysates of the treated slices revealed FK2 immunoreactivity with a pattern of discrete bands similar to that obtained in p35 knockout mice. FK1 immunoblots did not reveal immunoreactive bands (right panel).

C. Immunoblot showing that ubiquitination of PSD-95 does not affect PSD-95 protein levels. Brain lysates from p35 knockout (−/−) and wild-type (+/+) mice were immunoblotted for PSD-95 and actin. Quantification (mean±SEM) revealed that PSD-95 protein levels in the p35 knockout mice were 120.7%±30.5% versus wild-type, 100%±15.7%;

n=4; p>0.5. (PSD-95 immunoreactivity was normalized to that of actin and expressed as a percentage of wild-type control mice).

D. Immunoblot showing that roscovitine treatment does not affect the protein levels of PSD-95. Brain lysates from acute mouse forebrain slices treated with roscovitine (10 µM, 45 min) (R), or DMSO as control (D), were immunoblotted for PSD-95 and actin. Quantification (mean±SEM) revealed that PSD-95 protein levels in the roscovitine samples were 103.7%±18.7% versus DMSO control, 100%±15.8%; n=3; p>0.5. PSD-95 immunoreactivity was normalized to that of actin and expressed as a percentage of DMSO control.

Figure 4:
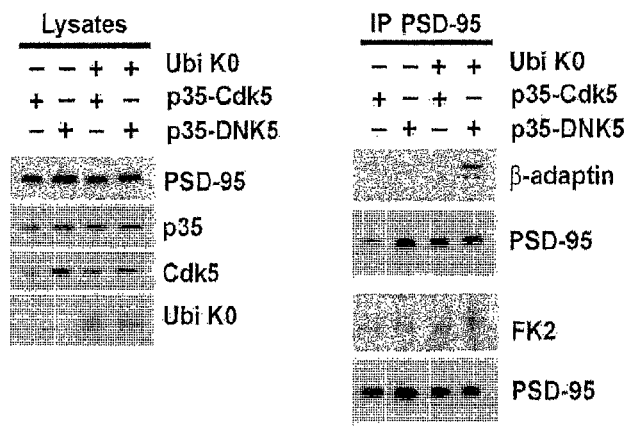
Figure 4:
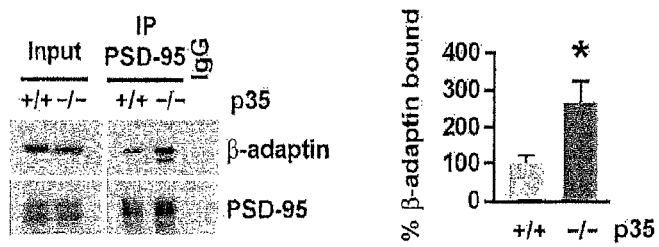
Figure 4:
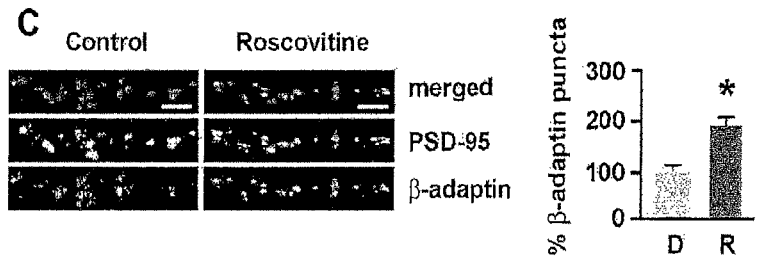
Figure 4:
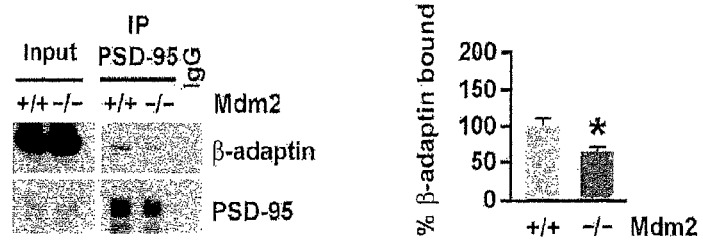

FIG. 4. Monoubiquitination of PSD-95 promotes the interaction with β-adaptin

A. Immunoblot showing that Cdk5-dependent ubiquitination regulates β-adaptin interaction with PSD-95. CAD cells were transfected with PSD-95 and p35-Cdk5 or p35-DNK5 (a dominant negative mutant of Cdk5) and with or without HA-Ubi K0 (a lysine K0 mutant of ubiquitin). Immunoblots of PSD-95 immunoprecipitated from transfected cell lysates revealed that coexpression of HA-Ubi K0 and p35-DNK5 increases PSD-95 monoubiquitination on multiple sites (FK2 immunoreactivity) and PSD-95 interaction with endogenous β-adaptin.

B. Immunoblot showing that p35 knockout mice have increased interaction of O-adaptin with PSD-95. PSD-95 immunoprecipitated from brain lysates of p35 knockout (−/−) and wild-type (+/+) mice revealed increased coimmunoprecipitation of β-adaptin with PSD-95 in p35 knockout. Quantification (mean±SEM) revealed that the interaction of β-adaptin with PSD-95 was increased to 265%±55.8% versus wild-type, 100%±16.4%; n=4; *, p<0.05. β-adaptin immunoreactivity was normalized to the level of immunoprecipitated PSD-95 and expressed as a percentage of wild-type control. IgG: control immunoprecipitation with mouse IgG.

C. Micrograph showing that roscovitine treatment of cultured hippocampal neurons increases the colocalization of β-adaptin with PSD-95. Cultured hippocampal neurons treated with roscovitine (10 µM, 45 min) or DMSO as control, were immunostained with antibodies against β-adaptin and PSD-95. Representative confocal images from each condition are shown; β-adaptin and PSD-95 (scale bars, 10 µm). Quantification (mean±SEM) revealed that in roscovitine-treated cultures (R) the percentage of puncta positive for both PSD-95 and β-adaptin was increased to 192.5%±19% versus 100%±15.6% DMSO control (D); n=5; *, p<0.01. The number of costained puncta, as a percentage of total number of PSD-95 puncta, is expressed as a percentage of the number for DMSO control.

D. Immunoblot showing that Mdm2 null mice have decreased interaction of PSD-95 with β-adaptin. PSD-95 immunoprecipitated from brain lysates of p53/Mdm2 double knockout (−/−) and p53 knockout control mice (+/+) revealed decreased coimmunoprecipitation of β-adaptin with PSD-95 in p53/Mdm2 double knockout mice. Quantification (mean±SEM) revealed that the interaction of β-adaptin with PSD-95 was decreased to 63.7%±8.8% of p53 knockout control 100%±10.8%; n=5; *, p<0.05. β-adaptin immunoreactivity was normalized to the level of immunoprecipitated PSD-95 and expressed as a percentage of p53 knockout control mice.

Figure 5:
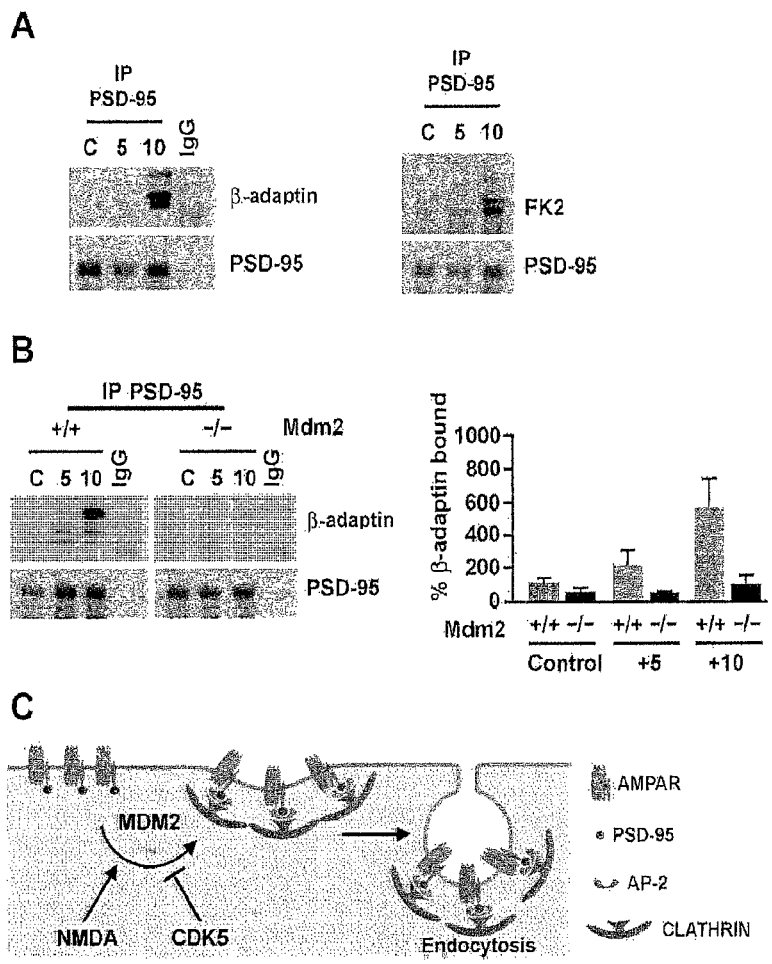

FIG. 5. NMDA receptors and Mdm2 regulate the interaction of PSD-95 with β-adaptin.

A. Immunoblot showing that NMDA receptors regulate the interaction of PSD-95 with β-adaptin. Acute forebrain slices from wild-type mice were stimulated with NMDA (100 µM, 3 min) and, after NMDA washout, incubated for additional 5 or 10 min. Immunoblots of PSD-95 immunoprecipitated from lysates revealed coimmunoprecipitation of β-adaptin with PSD-95 10 min after NMDA washout (10) compared to unstimulated control (C). FK2 immunoblots of PSD-95 revealed increased ubiquitination at 10 min after NMDA washout (10) compared to unstimulated control (C).

B. Immunoblot showing that genetic deletion of Mdm2 reduces the NMDA-dependent interaction of PSD-95 with β-adaptin. Acute forebrain slices from p53 knockout (control) and Mdm2/p53 double knockout mice were stimulated with NMDA (100 µM, 3 min) and, after NMDA washout, incubated for an additional 5 or 10 min. Immunoblots of PSD-95 immunoprecipitated from p53 knockout lysates (Mdm2+/+) revealed increased coimmunoprecipitation of β-adaptin with PSD-95 5 and 10 min after NMDA washout (5 and 10) compared to unstimulated control (C). Immunoblots of PSD-95 immunoprecipitated from lysates of Mdm2/p53 double knockout mice (Mdm2−/−) revealed an overall decrease in β-adaptin coimmunoprecipitated with PSD-95 compared to p53 knockout control mice (Mdm2+/+), both prior to (C) and after (5 and 10) NMDA treatment. In p53 knockout slices the interaction of β-adaptin with PSD-95 was increased 5 min after the end of 16 NMDA treatment compared to unstimulated control (209.0%±72.6%, versus control 100%±14.9%, n=3) and a further increase was observed at 10 min (549.8%±167.7%, n=3). In contrast, the levels of interaction between β-adaptin and PSD-95 were lower in unstimulated slices from Mdm2/p53 double knockout mice (50.5%±13.8% versus unstimulated control 100%±14.9%, n=3) as well as at 5 min (45.6%±1.8%, n=3) and 10 min (99.8%±43.7%, n=3) after the end of NMDA treatment. β-adaptin immunoreactivity was normalized to the level of immunoprecipitated PSD-95 and expressed as a percentage of p53 knockout unstimulated control.

C. Model: ubiquitination of PSD-95 as a signaling mechanism in AMPAR endocytosis. Both NMDAR stimulation and Cdk5 inactivation promote ubiquitination of PSD-95 by Mdm2. In turn, ubiquitinated PSD-95, by promoting its interaction with the AP-2/clathrin endocytic complex, recruits AMPARs to the AP-2/clathrin endocytic complex with subsequent internalization of AMPARs by clathrin-mediated endocytosis.

Figure 6:
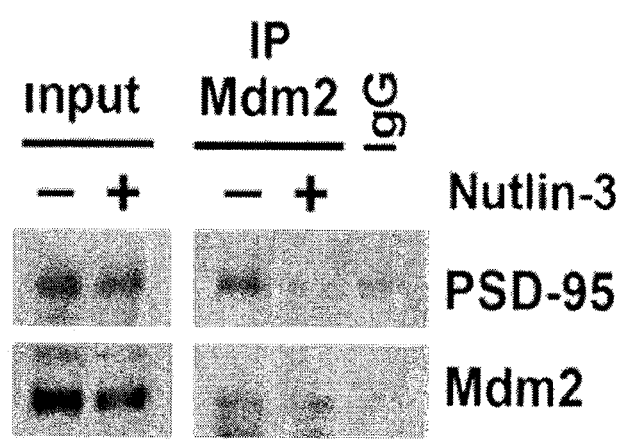
Figure 6:
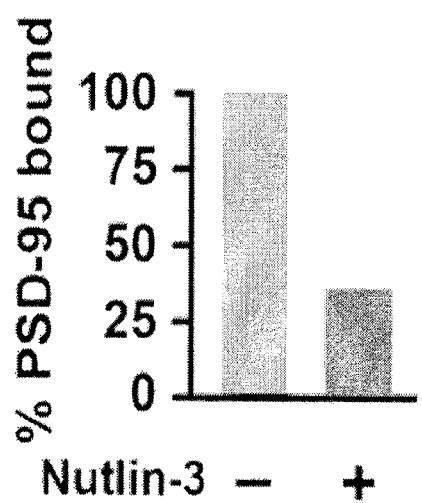

FIG. 6. Nutlin-3 reduces Mdm2 binding to PSD-95.

A. Immunoblot showing the interaction between Mdm2 and PSD-95 in the presence or absence of the Mdm2 inhibitor Nutlin-3. Acute mouse forebrain slices were treated with Nutlin-3 (5 µM for 30 min), followed by immunoprecipitation of Mdm2. Immunoprecipitates were subjected to Western blot analysis with anti-PSD-95 and anti-Mdm2 antibodies. IgG: control immunoprecipitation with mouse IgG.

B. A bar graph depicting the proportion of PSD-95 bound to Mdm2 from FIG. 6A, normalized to levels of PSD-95 bound to Mdm2 in the absence of Nutlin-3. There was a 60% decrease in the interaction of PSD-95 with Mdm2.

Figure 7:
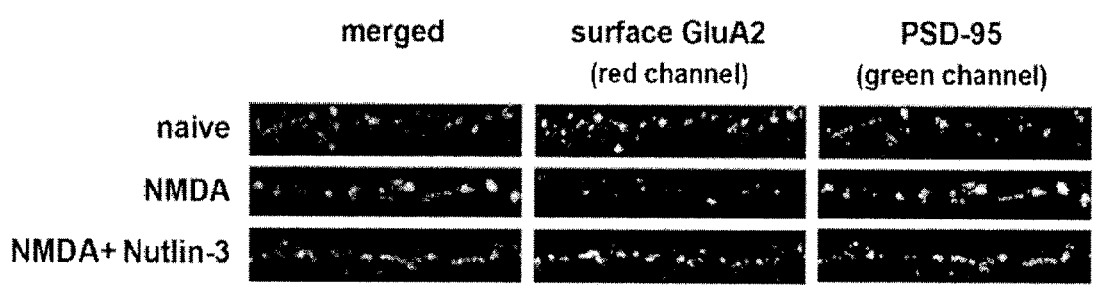
Figure 7:
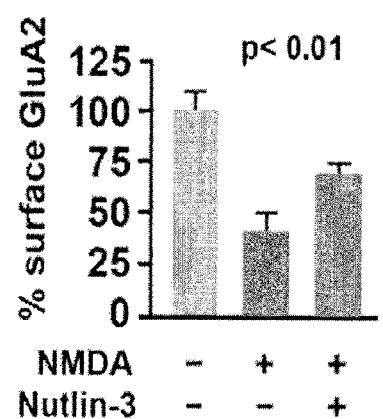

FIG. 7. Nutlin-3 reduces NMDA-induced AMPAR endocytosis

A. Micrograph showing GluA2 surface expression upon NMDA treatment in the presence or absence of Nutlin-3. Cultured hippocampal neurons were subjected to an antibody feeding protocol using an antibody that recognizes an extracellular domain of GluA2. The neurons were subsequently pretreated with Nutlin-3 (5 µM for 30 min) prior to NMDA treatment (100 µM for 3 min), followed by agonist washout. Neurons were incubated for an additional 15 min (with or without Nutlin-3) before immunocytochemical analysis of PSD-95 and surface GluA2 by confocal microscopy.

B. A bar graph depicting the proportion of GluA2 found at the surface of cultured hippocampal neurons upon treatment with or without NMDA, in the presence or absence of Nutlin-3. Results are presented as mean±SEM.

Figure 8:
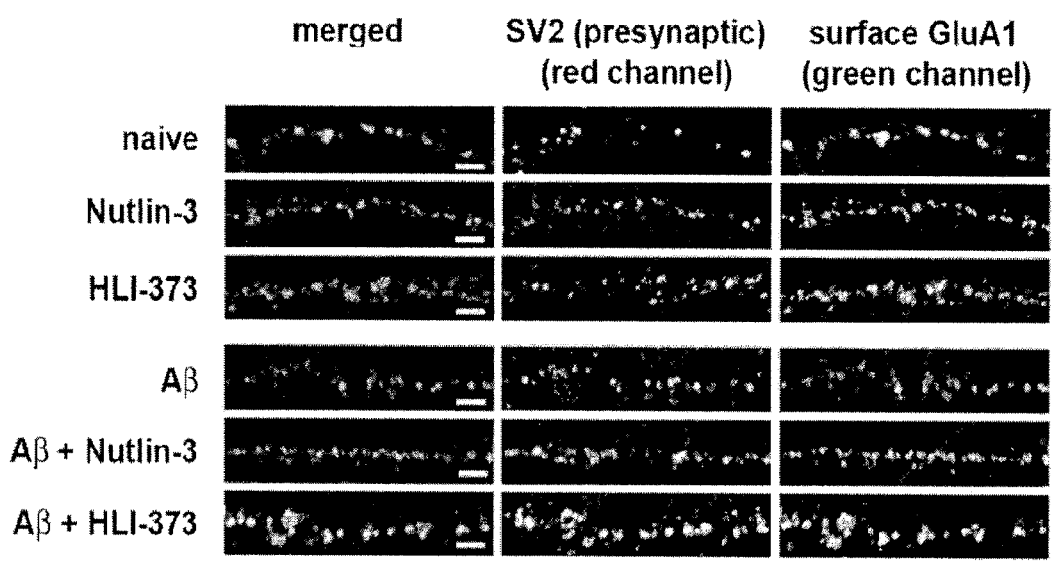
Figure 8:
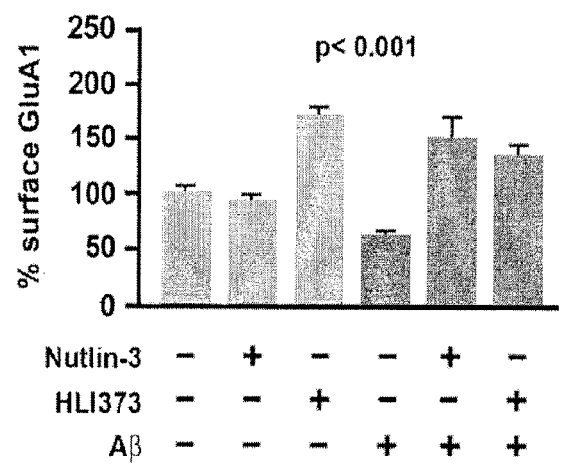

FIG. 8. Nutlin-3 and HLI373 reduce amyloid beta (Aβ)-induced AMPAR endocytosis A. Micrograph showing GluA2 surface expression upon Aβ treatment in the presence or absence of Nutlin-3. Rat hippocampal neurons were cultured, and treated with Aβ or Aβ together with either Nutlin-3 (5 µM) or HLI373 (15 µM) for 2 hours. The final concentration of Aβ was 0.3 ng/mL. Naïve and Nutlin-3 and HLI373 treatments, without Aβ treatment, were used as controls. Surface expression of AMPARs was measured by labeling the cultured neurons in vivo with an antibody to the AMPAR subunit GluA1, followed by confocal microscopy and immunofluorescence quantification by MetaMorph. The number of GluA1 puncta was normalized to SV2 puncta (a presynaptic marker) and to the value in control naïve cultures. As can be seen from the Figure, Nutlin-3 and HLI-373 prevented the loss of surface GluA1 induced by Aβ treatment. Scale bar=5 µm. B. Bar graph showing quantification of the percentage of surface GluA1 in response to the various treatment described in A. Results are presented as mean±SEM.

DETAILED DESCRIPTION OF THE INVENTION

The present invention is based, at least in part, on a newly-identified proteasome-independent signaling function of ubiquitinated PSD-95. It is demonstrated herein that genetic or pharmacological reduction of Cdk5 activity enhances PSD-95 monoubiquitination without resulting in changes in PSD-95 protein levels. The data presented herein indicate that PSD-95 monoubiquitination correlates with an increased interaction of PSD-95 with β-adaptin, a subunit of the clathrin adaptor protein complexes. It is also shown herein that NMDA receptor activity induces PSD-95 ubiquitination and interaction with β-adaptin and that this requires Mdm2 activity. These data indicate that monoubiquitination of PSD-95 functions in a proteasome-independent manner to recruit the clathrin endocytic complex and suggest a novel mechanism by which monoubiquitination of PSD-95 promotes NMDA receptor-induced AMPA receptor endocytosis.

Accordingly, the instant invention relates to the finding that in mammalian central nervous system (CNS) neurons, the ubiquitination of PSD-95 by the ubiquitin ligase (E3) Hdm2/Mdm2 regulates the interaction of PSD-95 with the clathrin adaptor complex and thus regulates the endocytosis of AMPA receptors. This mechanism is regulated by the kinase Cdk5.

Further, the instant invention relates to the finding that Mdm2 inhibitors that prevent the interaction between Mdm2 and its substrates, or inhibit Mdm2 enzymatic activity, prevent the decrease in surface expression of AMPARs induced by amyloid beta (Aβ) peptide.

The invention features the use of compounds that inhibit the activity, enzymatic activity and/or substrate binding activity of the ubiquitin ligase (E3) Hdm2/Mdm2 and its related protein Mdm4 (also known as Hdm4 and Hdmx)/MdmX. Such inhibitors are collectively referred to herein as "Mdm2 inhibitors" or "Mdm4 inhibitors." By way of example, such enzymatic activity modulators are deazaflavin compounds and their derivatives, including, but not limited to 7-nitro-5-deazaflavin; such modulators/inhibitors of substrate binding are Nutlin-3a, that (for the purpose of example) acts as inhibitors of the ubiquitin ligases Hdm2/Mdm2 and Mdm4/MdmX. Also contemplated are "PSD-95 inhibitors," (e.g., PSD-95 inhibitory peptides) which inhibit the binding between endogenous PSD-95 and its interacting proteins and/or inhibit the post-translational modification of endogenous PSD-95 (e.g., ubiquitination).

A separate aspect of the invention features a screen for compounds for the treatment of neurodegenerative diseases and/or psychiatric disorders, where the screen is comprised of Membrane-Associated Guanylate Kinase (MAGUK) proteins such as PSD-95/SAP90, PSD-95/SAP90/discs large homolog (DLG4), Channel-associate protein of synapse-110 (Chapsyn-110)/PSD-93/DLG2, SAP97/DLG1, SAP102/DLG3, and an ubiquitin ligase such as Hdm2/Mdm2. Compounds will be identified in this screen by the ability of the compounds to inhibit the interaction of the ubiquitin ligase Hdm2/Mdm2 protein with its substrate MAGUK protein. Assays for carrying out such screens are described infra.

Definitions

Unless otherwise indicated, all terms used herein have the same meaning as they would to one skilled in the art, and the practice of the present invention will employ conventional techniques of microbiology and recombinant DNA technology, which are within the knowledge of those of skill in the art. The practice of the present invention will employ, unless otherwise indicated, conventional methods of virology, microbiology, molecular biology, and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.).

As used herein, the term "Mdm2 inhibitor" or "Mdm4 inhibitor" refers to agents that decrease the E3 ubiquitin ligase activity of Mdm2 and/or Mdm4. The term also encompasses agents that decrease the binding between Mdm2 and/or Mdm4 and their respective substrates. In addition to art-recognized agents (e.g., Nutlin-3a [(−)-4-(4,5-bis(4-chlorophenyl)-2-(2-isopropoxy-4-methoxyphenyl)-4,5-dihydro-1H-imidazole-1-carbonyl)piperazin-2-one], HLI-373), an Mdm2 inhibitor and/or Mdm4 inhibitor is intended to encompass as of yet unidentified compounds that can readily be identified by the screening assays described infra.

As used herein, the term "derivative" or "derivatives" refers to a chemical substance or compound related structurally to another substance or compound and theoretically obtainable from it, i.e., a substance or compound that can be made from another substance or compound. Derivatives can include compounds obtained via a chemical reaction.

As used herein, the term "enantiomer" or "enantiomers" refers to stereoisomers of molecules that are non-superimposable mirror images of each other. Enantiomers have identical physical properties, such as melting points and boiling points, and also have identical spectroscopic properties. Enantiomers differ from each other with respect to their interaction with plane-polarized light and with respect to biological activity.

As used herein, the terms "enzymatic activity of Mdm2," "enzymatic activity of Mdm4," "Mdm2 activity," or "Mdm4 activity" all refer to the E3 ubiquitin ligase activity of Mdm2 and/or Mdm4. Accordingly, "inhibit the enzymatic activity of Mdm2 and/or Mdm4" or "inhibit Mdm2 and/or Mdm4 activity" is intended to mean the inhibition of Mdm2 and/or Mdm4 E3 ubiquitin ligase activity, as measured by, e.g., the methods described infra.

As used herein, the term "PSD-95 inhibitors" refers to compounds that inhibit the binding between PSD-95 and its interacting proteins and/or decrease the post-translational modifications of PSD-95 (e.g., ubiquitination). For example, in one embodiment, PSD-95 inhibitors are PSD-95-inhibitory peptides. Such inhibitory peptides may or may not be fused to a cell penetrating sequence, e.g., a human immunodeficiency virus (HIV) transactivator of transcription (TAT) polypeptide. In another embodiment, PSD-95 inhibitors are small molecule inhibitors. In yet another embodiment, PSD-95 inhibitors are peptidomimetics. Compounds that function as PSD-95 inhibitors can be identified using, e.g., assays described infra.

As used herein, the term "modulate" or "modulating" means changing or altering, and embraces downmodulating or upmodulating, downregulating or upregulating, inhibition or activation, or decreasing or increasing, a particular activity or function of a protein.

As used herein, the term "inhibit" refers to the act of diminishing, decreasing, suppressing, alleviating, preventing, reducing, or eliminating. The term "inhibit" can be used to describe the effect of a compound on an enzymatic activity. Thus, the term "inhibit" as it applies to the analysis of enzymatic activity encompasses a range of effects, from completely eliminating to partially reducing. Accordingly, inhibition of enzymatic activity (e.g., Mdm2 or Mdm4 ubiquitin ligase activity) refers to inhibition of at least 10%, or at least 20%, or at least 30%, or at least 40%, or at least 50%, or at least 60%, or at least 70%, or at least 80%, or at least 90%, or at least 95% of enzymatic activity. The term "inhibit" as it applies to the interaction or binding between Mdm2 and/or Mdm4 and PSD-95, non-PSD-95 MAGUK proteins, and/or PSD-95 associated proteins refers to complete or partial reduction in binding as assessed using methods described infra. Accordingly, inhibition of interaction or binding refers to inhibition of at least 10%, or at least 20%, or at least 30%, or at least 40%, or at least 50%, or at least 60%, or at least 70%, or at least 80%, or at least 90%, or at least 95%, or at least 97%, or at least 99% of the interaction or binding. The term "inhibit" can be applied to both in vitro as well as in vivo systems.

As used herein, the term "substrate" refers to a substance (e.g., protein, peptide) on which an enzyme performs its catalytic activity to generate a product. For example, in the context of the present invention, PSD-95 is a substrate of Mdm2 and/or Mdm4, wherein Mdm2 and/or Mdm4 catalyzes the monoubiquitination of PSD-95.

As used herein, the term "in vitro" has its art recognized meaning, i.e., involving components of an organism that have been isolated from their usual biological context, e.g., involving (a) cells derived from multicellular organisms (cell culture or tissue culture living cells, e.g., immortalized cells, primary cells, cell lines, and an the like), (b) subcellular components (e.g. mitochondria or ribosomes), (c) extracts including cellular and/or subcellular extracts (e.g. wheat germ or reticulocyte extracts), or (d) purified reagents or molecules in the test tube (often proteins, DNA, or RNA, either individually or in combination). The term "in vivo" also has its art recognized meaning, e.g., involving organisms in their normal, intact state. The term "ex vivo" also has its art recognized meaning, i.e., involving functional tissues or organs that have been removed from the intact organism.

As used herein, the term "test compound" or "test agent" refers to a compound or molecule that has not previously been conclusively identified as a compound having a particular, tested biological, biochemical or chemical activity. In exemplary aspects of the invention, the term "test compound" or "test agent" refers to a compound or molecule that inhibits the enzymatic activity of, e.g., Mdm2 and/or Mdm4, a compound with the ability to inhibit the binding of Mdm2 and/or Mdm4 with their respective substrates (e.g., p53, PSD-95), a peptide or chemical compound that inhibits the binding between PSD-95 and its interacting proteins, and a peptide that inhibits the post-translational modification of PSD-95. In addition to Mdm2 and Mdm4 inhibitors, an "agent" and "compound" is intended to encompass PSD-95 inhibitors.

As used herein, the term "subject" includes humans and non-human animals amenable to therapy, e.g., preferably mammals and animals susceptible to neurological disorders, neurodevelopmental disorders, or psychiatric disorders, such as non-human primates, transgenic animals, dogs, cats, horses, and cows. The term "subject" also includes patients, more preferably patients having, or suspected of having a neurological disorder, neurodevelopmental disorder, or psychiatric disorder. The term "subject" also can be used to refer to a cell or a tissue, preferably a cell or diseased tissue.

As used herein, the term "neurological disorder" is intended to encompass disorders or the nervous system of a subject, including, for example, the brain, spinal cord and/or nerves. Neurological disorders can result from structural, biochemical and/or electrical abnormalities in the brain, spinal cord, and/or in the nerves leading to or from the brain or spinal cord. Neurological disorders can result from genetic defects, developmental defects, degenerative processes, disorders of the blood vessels that supply neuronal tissues, seizure disorders, cancers of neuronal tissues or organs, and/or neuronal infections. Neurologic disorders are characterized by one or more symptoms including, but not limited to, paralysis, muscle weakness, poor coordination, loss of sensation, seizures, confusion, pain, altered levels of consciousness, impairments in moving, speaking, swallowing, breathing and/or learning, and/or affected memory, senses and/or mood.

The term "neurodegenerative disease" refers to the loss, e.g., the progressive loss, of structure and/or function of neurons, including death of neurons. Neurodegenerative diseases are frequently characterized by the development of cognitive impairment and dementia. These include, but are not limited to, cognitive impairment, cognitive dysfunction, Alzheimer's disease, Parkinson's disease, and dementia. Definitions of these and other dementia-related disorders can be found in the Diagnostic and Statistical Manual (DSM-IV), American Psychological Association (APA).

As used herein, the term "neurodevelopmental disorder" is intended to encompass disorders that result from abnormal development of the nervous system, e.g., brain, and are often, but not always (some result from epigenetic factors), genetic in nature. Non-limiting examples of neurodevelopmental disorders include autism spectrum disorders, fragile- X, disorders affecting emotion, learning ability, and memory, and Down's syndrome. Definitions of these and other neurodevelopmental disorders can be found in, e.g., Rachidi et al., 2008; Pardo et al., 2007; Karlsgodt et al., 2008; Segawa et al., 2005; Mayes, 1999.

As used herein, the term "psychiatric disorder" refers to a pattern or profile of psychological or behavioral symptoms that causes a subject significant distress, impairs their ability to function normally, and/or significantly increases their risk of death, pain, disability, or loss of freedom. The term "psychiatric disorder" is intended to encompass, but not limited to, schizophrenia, bipolar disorder, depression, major depressive disorder, anxiety disorder, attention-deficit hyperactivity disorder, and substance abuse. Definitions for various psychiatric disorders can be found in DSM-IV.

Contemplated in the present invention are the use of newly identified (i.e., based on screens described infra) Mdm2 and/or Mdm4 inhibitors that are blood-brain barrier permeable.

As used herein, "treatment" refers to a process, manner, or regimen which allows for medicinal or surgical care for an illness or injury in a subject. In certain embodiments, the treatment comprises diminishing or alleviating at least one symptom directly or indirectly associated with or caused by a neurological disorder, neurodevelopmental disorder, or psychiatric disorder.

As used herein, a "treatment regimen" refers to a regulated course of treatment intended to preserve or restore health, or attain some result, e.g., inhibit or suppress a neurological disorder, neurodevelopmental disorder, or psychiatric disorder. In one embodiment, the treatment regimen may include administering an Mdm2 and/or Mdm4 inhibitor (e.g., Nutlin-3a, HLI-373) or PSD-95 inhibitor. In a further embodiment, the treatment regimen may include combinatorial treatments, such as combining an Mdm2 and/or Mdm4 inhibitor or PSD-95 inhibitor with, e.g., an NMDAR antagonist (e.g., memantine; 1-amino-3,5-dimethyl-adamantane) to a subject. Memantine has been shown to improve cognition and reduce AD-like neuropathology in 3×Tg-AD mice (Martinez-Coria-LaFeria, 2010). This, of course, is by way of example, and depending on the disease or disorder to be treated, an Mdm2 and/or Mdm4 inhibitor or PSD-95 inhibitor can be used in conjunction with an agent known to be beneficial for treating said disease or disorder.

As used herein, the term "diseased tissue" refers to a tissue sample from an organism or a tissue within an organism that has or exhibits characteristics of a disease or disorder. In one embodiment, the diseased tissue is from a subject with a neurological disorder, neurodevelopmental disorder, or psychiatric disorder.

As used herein, the term "non-PSD-95 MAGUK protein" refers to a MAGUK protein other than PSD-95. Some non-limiting examples of non-PSD-95 MAGUK proteins are SAP97, SAP102, and PSD-93.

A "therapeutically effective amount" of a substance is an amount capable of producing a medically desirable result in a treated patient, e.g., inhibition of the activity or interaction with binding partners or substrates of a specific protein, e.g., Mdm2, Mdm4, or PSD-95. A therapeutically effective amount of a Mdm2 and/or Mdm4 inhibitor or a PSD-95 inhibitor refers to an amount capable of inhibiting the activity of Mdm2 and/or Mdm4, interactions with their respective substrates or binding between PSD-95 and its interacting partners.

As used herein, "substantially identical" refers to a target, for instance a nucleic acid or peptide, which is at least 50% identical in sequence to the reference. In a non-limiting example, the reference can be a stretch of amino acids in a protein (e.g., PSD-95) that functions as a binding interface with a target interacting protein. In this context, a substantially identical peptide refers to a peptide that is at least 50, 60, 70, 80, 90, 95, 96, 97, 98, or 99% identical in amino acid sequence to the stretch of amino acids in, e.g., PSD-95, that functions as a binding interface with a target interacting protein. Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10. In some embodiments, global identity is over the entire sequence being compared.

As used herein, a "peptide mimetic" or "peptidomimetic", which are used interchangeably, refers to a peptide-like molecule that has the activity of the peptide upon which it is structurally based. Such peptide mimetics include chemically modified peptides, peptide-like molecules containing non-naturally occurring amino acids, and peptoids (see, e.g., Goodman and Ro, Peptidomimetics for Drug Design, in "Burger's Medicinal Chemistry and Drug Discovery" Vol. 1 (ed. M. E. Wolff; John Wiley & Sons 1995). In some embodiments of the invention, up to 20 peptide bonds have been replaced with an alternative type of covalent bond that is not susceptible to cleavage by peptidases. In other embodiments, up to 15, up to 10, or up to 5 peptide bonds have been replaced with an alternative type of covalent bond that is not susceptible to cleavage by peptidases. Particularly in instances where proteolytic degradation upon administration to a mammal is an issue, sensitive peptide bonds can be replaced with a non-cleavable peptide mimetic renders the peptide more stable. Such peptide mimetics, and methods of introducing them into peptides, are well known in the art.

It should be understood that when the term "about" is used in the context of specific values or ranges of values, the disclosure should be read as to include the specific value or range referred to.

Various methodologies of the instant invention include steps involving comparing, e.g., a value, level, feature, characteristic, property, to a "suitable control," referred to interchangeably herein as an "appropriate control." A "suitable control," is any control or standard familiar to the skilled artisan useful for comparison purposes. In one embodiment, a "suitable control" or "appropriate control" is, e.g., a value, level, feature, characteristic, property determined prior to performing a given methodology, as described herein. For example, a transcription rate, mRNA level, translation rate, protein level, biological activity, cellular characteristics or property, genotype, or phenotype can be determined prior to introduction of a compound (e.g., a Mdm2 inhibitor) of the invention into a cell or organism. In certain embodiments, a suitable control is, e.g., a value, level, feature, characteristic, or property, determined in a cell or organism, e.g., a cell or organism afflicted with a neurological disorder, neurodevelopmental disorder, or psychiatric disorder, in the absence of, e.g., a Mdm2 and/or Mdm4 inhibitor. In methodologies that involve initiating a neurological disorder, neurodevelopmental disorder, or psychiatric disorder in an organism, the properties of a "suitable control" or an "appropriate control" can also be determined in cells or organisms that are healthy or do not have the neurological disorder, neurodevelopmental disorder, or psychiatric disorder. In another embodiment, a "suitable control" is a value, level, feature, characteristic, property, etc., determined in a cell or organism, e.g., a control of normal cell or organism, exhibiting, e.g., normal traits. In yet another embodiment, a "suitable control" or "appropriate control" is, e.g., a predefined value, level, feature, characteristic, or property.

I. Components and Process Involved in AMPA, NMDAR, and D1 Dopamine Receptor Endocytosis

A. PSD-95

PSD-95 is a major postsynaptic scaffolding protein of glutamatergic synapses that regulates synaptic strength and plasticity. Ubiquitination of PSD-95 by Mdm2, and NMDA receptor-dependent ubiquitination of PSD-95, is critical in regulating AMPA receptor surface expression in long-term depression (LTD).

PSD-95 is a neuronal PDZ protein that associates with receptors and cytoskeletal elements at synapses. PSD-95, a prototypical structural and signaling scaffold in the postsynaptic density, inhibits D1-NMDA receptor.

PSD-95, also known as disks large homolog 4 (DLG4), is member of the membrane-associated guanylate kinase (MAGUK) family. It heteromultimerizes with DLG2 and is subsequently recruited into the same NMDA receptor and potassium channel clusters. These two MAGUK proteins may interact at postsynaptic sites to form a multimeric scaffold for the clustering of receptors, ion channels, and associated signaling proteins.

PSD-95 is the best-studied member of the MAGUK-family of PDZ domain-containing proteins. Like all MAGUK-family proteins, its basic structure includes three PDZ domains, an src homology (SH)3 domain, and a guanylate kinase-like domain (GK) connected by disordered linker regions. It is almost exclusively located in the post synaptic density of neurons, and is involved in anchoring synaptic proteins. Its direct and indirect binding partners include neuroligin, NMDA receptors, AMPA receptors, beta-1 adrenergic receptors, v-Erb A Erythroblastic Leukemia Viral Oncogene Homolog (ErbB)4 (Garcia et al., 2000), Apolipoprotein E receptor (ApoER2) (Hoe et al., 2006), as well as other membrane proteins that associate with PSD-95 and neuroligin, and potassium channels. PSD-95 has also been shown to bind to $D_1$ and $D_2$ dopamine receptors and regulate their endocytic trafficking (Zhang et al., *JBC* (2007) 282:15778-89; Sun et al., *Cell Research* (2009) 19:612-624). In fact, PSD-95 has an extensive interaction network with 118 protein interactors identified (Fernandez et al., 2009).

PSD-95 is a member of the MAGUK superfamily, and part of a subfamily which also includes PSD-93, SAP97 and SAP102. The MAGUKs are defined by their inclusion of PDZ, SH3 and GUK domains, although many also contain regions homologous of Calcium/Calmodulin-Dependent Protein Kinase (CaMK)II, WW and L27 domains. The guanylate kinase (GUK) domain is structurally very similar to that of guanylate kinases, however it is known to be catalytically inactive, as the P-Loop which binds ATP is absent. It is thought that the MAGUKs have subfunctionalized the GUK domain for their own purposes, primarily based on their ability to participate in protein-protein interactions with cytoskeleton proteins, microtubule/actin based machinery and molecules involved in signal transduction.

The PDZ domain, which is contained in MAGUKs in varying numbers, is replicated three times over in DLG4. PDZ domains are short peptide binding sequences commonly found at C-terminals of interacting proteins. The three copies within the gene have different binding partners, due to amino acid substitutions within the DLG4 protein and its ligands. The SH3 domain is again a protein-protein interaction domain. Its family generally binds to PXXP sites, but in MAGUKs it is known to bind to other sites as well. One of the most well-known features is that it can form an intramolecular bond with the GUK domain, creating what is known as a GUK-SH3 'closed' state. The regulatory mechanisms and function are unknown, but it is hypothesized that it may involve a hook region and a calmodulin (CaM) binding region located elsewhere in the gene.

```
LOCUS       NP_001122299            721 aa      linear   PRI 04 NOV. 2010
DEFINITION  disks large homolog 4 isoform 2 [Homo sapiens].
ACCESSION   NP_001122299
VERSION     NP_001122299.1  GI:192447426
DBSOURCE    REFSEQ: accession NM_001128827.1
KEYWORDS    .
SOURCE      Homo sapiens (human)
  ORGANISM  Homo sapiens Transcript Variant: This variant (2) contains a distinct 5' UTR and
            5' coding region and uses an alternate in-frame splice site,
            compared to variant 1. The resulting isoform (2) has a shorter and
            distinct N-terminus and lacks a 3 amino acid internal segment when
            compared to isoform 1.
```

-continued

```
FEATURES        Location/Qualifiers
  source        1..721
                /organism="Homo sapiens"
                /db_xref="taxon:9606"
                /chromosome="17"
                /map="17p13.1"
  Protein       1..721
                /product="disks large homolog 4 isoform 2"
                /note="discs large homolog 4; synapse-associated protein
                90; Tax interaction protein 15; post-synaptic density
                protein 95; postsynaptic density protein 95; disks large
                homolog 4"
                /calculated_mol_wt=79994
  Region        10..61
                /region_name="MAGUK_N_PEST"
                /note="Polyubiquitination (PEST) N-terminal domain of
                MAGUK; pfam10608"
                /db_xref="CDD:151134"
  Region        62..145
                /region_name="PDZ_signaling"
                /note="PDZ domain found in a variety of Eumetazoan
                signaling molecules, often in tandem arrangements. May be
                responsible for specific protein-protein interactions, as
                most PDZ domains bind C-terminal polypeptides, and binding
                to internal (non-C-terminal)...; cd00992"
                /db_xref="CDD:29049"
  Site          order(71..74,76,130..131,134..135)
                /site_type="other"
                /note="protein binding site"
                /db_xref="CDD:29049"
  Region        155..241
                /region_name="PDZ_signaling"
                /note="PDZ domain found in a variety of Eumetazoan
                signaling molecules, often in tandem arrangements. May be
                responsible for specific protein-protein interactions, as
                most PDZ domains bind C-terminal polypeptides, and binding
                to internal (non-C-terminal)...; cd00992"
                /db_xref="CDD:29049"
  Site          order(166..169,171,225..226,229..230)
                /site_type="other"
                /note="protein binding site"
                /db_xref="CDD:29049"
  Region        242..309
                /region_name="PDZ_assoc"
                /note="PDZ-associated domain of NMDA receptors; pfam10600"
                /db_xref="CDD:151128"
  Region        308..388
                /region_name="PDZ_signaling"
                /note="PDZ domain found in a variety of Eumetazoan
                signaling molecules, often in tandem arrangements. May be
                responsible for specific protein-protein interactions, as
                most PDZ domains bind C-terminal polypeptides, and binding
                to internal (non-C-terminal)...; cd00992"
                /db_xref="CDD:29049"
  Site          order(319..322,324,372..373,376..377)
                /site_type="other"
                /note="protein binding site"
                /db_xref="CDD:29049"
  Region        429..487
                /region_name="SH3"
                /note="Src homology 3 domains; SH3 domains bind to
                proline-rich ligands with moderate affinity and
                selectivity, preferentially to PxxP motifs; they play a
                role in the regulation of enzymes by intramolecular
                interactions, changing the subcellular localization...;
                cd00174"
                /db_xref="CDD:29136"
  Site          order(434,436,448,467,486)
                /site_type="other"
                /note="proline-rich ligand binding site"
                /db_xref="CDD:29136"
  Site          order(439..440,447..448,459..460,465..466)
                /site_type="other"
                /note="RTand n-Src loops"
                /db_xref="CDD:29136"
```

```
Region          533..649
                /region_name="GMPK"
                /note="Guanosine monophosphate kinase (GMPK, EC 2.7.4.8),
                also known as guanylate kinase (GKase), catalyzes the
                reversible phosphoryl transfer from adenosine triphosphate
                (ATP) to guanosine monophosphate (GMP) to yield adenosine
                diphosphate (ADP) and...; cd00071"
                /db-xref="CDD:73180"
Site            order(538,541,558,565,568,577,601,606)
                /site_type="other"
                /note="catalytic site"
                /db_xref="CDD:73180"
Site            order(538,541)
                /site_type="other"
                /note="G-X2-G-X-G-K"
                /db_xref="CDD:73180"
CDS             1..721
                /gene="DLG4"
                /gene_synonym="FLJ97752; FLJ98574; PSD95; SAP-90; SAP90"
                /coded_by="NM_001128827.1:463..2628"
                /note="isoform 2 is encoded by transcript variant 2"
                /db_xref="CCDS:CCDS45600.1"
                /db_xref="GeneID:1742"
                /db_xref="HGNC:2903"
                /db_xref="MIM:602887"
ORIGIN
    1 mdclcivttk kyryqdedtp plehspahlp nqansppviv ntdtleapgy vngtegemey
   61 eeitlergns glgfsiaggt dnphigddps ifitkiipgg aaaqdgrlry ndsilfvnev
  121 dvrevthsaa vealkeagsi vrlyvmrrkp paekvmeikl ikgpkglgfs iaggvgnqhi
  181 pgdnsiyvtk iieggaahkd grlqigdkil avnsvgledv mhedavaalk ntydvvylkv
  241 akpsnaylsd syappditts ysqhldneis hssylgtdyp tamtptsprr yspvakdllg
  301 eedipreprr ivihrgstgl gfnivggedg egifisfila ggpadlsgel rkgdqilsvn
  361 gvdlrnashe qaaialknag qtvtilaqyk peeysrfeak ihdlreqlmn sslgsgtasl
  421 rsnpkrgfyi ralfdydktk dcgflsqals frfgdvlhvi dasdeewwqa rrvhsdsetd
  481 digfipskrr verrewsrlk akdwgsssgs qgredsvlsy etvtqmevhy arpiiilgpt
  541 kdranddlls efpdkfgscv phttrpkrey eidgrdyhfv ssrekmekdi qahkfieagq
  601 ynshlygtsv qsvrevaeqg khcildvsan avrrlqaahl hpiaifirpr slenvleink
  661 riteeqarka fdratkleqe ftecfsaive gdsfeeiyhk vkrviedlsg pyiwvparer
  721 l
//
```

B. Regulation of PSD-95 by CDK5

Cyclin-dependent kinase 5, also known as cell division protein kinase 5 is proline-directed serine/threonine kinase encoded by the CDK5 gene. The protein encoded by this gene is part of the cyclin-dependent kinase family. Recently Cdk5 has emerged as an essential kinase in sensory pathways. CDK5 was originally named NCLK for Neuronal cell division control (CDC)2-Like Kinase due to its similar phosphorylation motif, and when in combination with an activator, was also referred to as Tau Protein Kinase II. CDK5 is required for proper development of the brain and to be activated, CDK5 must associate with CDK5 regulatory subunit (R)1 or CDK5R2. Unlike other cyclin dependent kinases, CDK5 does not also require phosphorylation on the T loop. Accordingly, binding with the activator is sufficient to activate the kinase.

Cdk5 plays an important role in neurodevelopment, particularly neuronal maturation and migration, via phosphorylation of the key intracellular adaptor of the reelin signaling chain. Experiments performed on mice lacking p35, a necessary activator of cdk5 in early brain development, showed that the normal layering of neurons was reversed in the cortex. This disrupted lamination again implicated cdk5 in neuronal migration and plasticity. Cdk5 is also involved in the regulation of synaptic vesicle exocytosis via phosphorylation of munc-18. Dysregulation of this enzyme has been implicated in several neurodegenerative diseases including Alzheimer's disease.

Cdk5 is activated by the regulatory subunit p35 or p39 and is involved, as described above, in brain development, as well as synaptic plasticity and drug addiction. Cdk5 activity is regulated by NMDA receptor activity and in turn regulates NMDA-dependent synaptic plasticity such as LTP and LTD (Wei et al, 2005; Ohshima et al., 2005; Hawasli et al., 2007). Previous studies by the same contributors have shown that Cdk5 phosphorylates PSD-95 (Morabito et al., 2004), a major postsynaptic scaffolding protein of glutamatergic synapses that associates with AMPA receptors via its interaction with transmembrane AMPA receptor regulatory proteins (TARPs) (Chen et al., 2000; Schnell et al., 2002). PSD-95 plays a role in the regulation of surface expression of AMPA receptors (Elias & Nicoll, 2007) and of NMDA receptor-dependent LTP and LTD (Kim & Sheng, 2004).

With respect to the regulation of PSD-95 by Cdk5, PSD-95 is known to harbor two PEST motifs in the N-terminus that are critical for PSD-95 ubiquitination (Colledge et al., 2003). Importantly, these motifs include two Cdk5 phosphorylation sites (Morabito et al., 2004), and pharmacological inhibition of Cdk5 by roscovitine in acute mouse brain slices resulted in increased PSD-95 ubiquitination. Similarly, in brain lysates from p35 knockout mice, which have reduced Cdk5 activity, the degree of PSD-95 ubiquitination was also increased relative to wild-type brain lysates. Consistent with increased PSD-95 ubiquitination, the interaction of PSD-95 with Mdm2 was greater under conditions of reduced Cdk5 activity. Furthermore, the studies presented herein indicate that in both roscovitine-treated slices and p35 knockout mice, PSD-95 was monoubiquitinated rather than polyubiquitinated. Consistent with mono-rather than polyubiquitination of PSD-95, quantification of PSD-95 protein levels in lysates from both roscovitine-treated neurons and p35 knockout brain revealed that overall PSD-95 protein levels were not altered. Together, these results identify Cdk5 as a regulator of PSD-95 ubiquitination and provide insight into the mechanisms by which Cdk5 regulates AMPAR surface expression and synaptic plasticity.

C. Ubiquitination

Ubiquitination is an enzymatic, protein post-translational modification (PTM) process in which the carboxylic acid of the terminal glycine from the di-glycine motif in the activated ubiquitin forms an amide bond to the epsilon amine of the lysine in the modified protein. The process of ubiquitinating a protein involves a series of steps:

Activation of ubiquitin: Ubiquitin is activated in a two-step reaction by an E1 ubiquitin-activating enzyme in a process requiring ATP as an energy source. The initial step involves production of an ubiquitin-adenylate intermediate. The second step transfers ubiquitin to the E1 active site cysteine residue, with release of AMP. This step results in a thioester linkage between the C-terminal carboxyl group of ubiquitin and the E1 cysteine sulfhydryl group.

Transfer of ubiquitin from E1 to the active site cysteine of a ubiquitin-conjugating enzyme E2 via a trans(thio)esterification reaction. Mammalian genomes contain 30-40 UBCs.

The final step of the ubiquitination cascade creates an isopeptide bond between a lysine of the target protein and the C-terminal glycine of ubiquitin. In general, this step requires the activity of one of the hundreds of E3 ubiquitin-protein ligases (often termed simply ubiquitin ligase). E3 enzymes function as the substrate recognition modules of the system and are capable of interaction with both E2 and substrate.

In the ubiquitination cascade E1 can bind with dozens of E2s which can bind with hundreds of E3s in a hierarchical way. Other ubiquitin-like proteins (ULPs) are also modified via the E1-E2-E3 cascade.

E3 enzymes possess one of two domains:

The HECT (Homologous to the E6-AP Carboxyl Terminus) domain

The RING (Really Interesting New Gene) domain (or the closely-related U-box domain)

Transfer can occur in two ways:

Directly from E2, catalyzed by RING domain E3s.

Via an E3 enzyme, catalyzed by HECT domain E3s. In this case, a covalent E3-ubiquitin intermediate is formed before transfer of ubiquitin to the substrate protein.

Ubiquitination of synaptic proteins is thought to regulate activity-dependent synaptic plasticity and remodeling. PSD-95 ubiquitination by the E3 ubiquitin ligase Mdm2 has been implicated in NMDA induced AMPA receptor endocytosis (Colledge et al., 2003). Although ubiquitination of PSD-95 has been difficult to detect (Bingol & Schuman, 2004), a recent study indicates that NMDA-induced AMPA receptor endocytosis and LTD depend at least in part on ubiquitination but occur independently of proteasome function (Citri et al., 2009).

D. AMPA, NMDA, and D1 Dopamine Receptors

The α-amino-3-hydroxy-5-methyl-4-isoxazolepropionic acid receptor (also known as AMPA receptor, AMPAR, or quisqualate receptor) is a non-NMDA-type ionotropic transmembrane receptor for glutamate that mediates fast synaptic transmission in the central nervous system (CNS). Its name is derived from its ability to be activated by the artificial glutamate analog AMPA. AMPARs are found in many parts of the brain and are the most commonly found receptor in the nervous system.

AMPARs are composed of four types of subunits, designated as GluR1 (GRIA1), GluR2 (GRIA2), GluR3 (GRIA3), and GluR4, alternatively called GluRA-D2 (GRIA4), which combine to form tetramers. Most AMPARs are heterotetrameric, consisting of symmetric 'dimer of dimers' of GluR2 and either GluR1, GluR3 or GluR4. Dimerization starts in the Endoplasmic reticulum with the interaction of n-terminal leucine, isoleucine, and valine binding protein (LIVBP) domains, then "zips up" through the ligand-binding domain into the transmembrane ion pore.

The conformation of the subunit protein in the plasma membrane caused controversy for some time. While the amino acid sequence of the subunit indicated that there were four transmembrane domains (parts of the protein that pass through the plasma membrane), proteins interacting with the subunit indicated that the N-terminus was extracellular while the C-terminus was intracellular. If each of the four transmembrane domains went all the way through the plasma membrane, then the two termini would have to be on the same side of the membrane. Eventually, it was discovered that the second transmembrane domain is not in fact trans at all, but kinks back on itself within the membrane and returns to the intracellular side (see schematic diagram). When the four subunits of the tetramer come together, this second membranous domain forms the ion-permeable pore of the receptor.

AMPAR subunits differ most in their c-terminal sequence, which determines their interactions with scaffolding proteins. All AMPARs contain PDZ-binding domains, but which PDZ domain they bind to differs. For example, GluR1 binds to SAP97 through SAP97's class I PDZ domain, while GluR2 binds to protein interacting with C kinase (PICK)1 and glutamate receptor-interacting protein (GRIP)/ABP. Of note, AMPARs cannot directly bind to the common synaptic protein PSD-95 due to incompatible PDZ domains.

AMPA receptors (AMPAR) are both glutamate receptors and cation channels that are integral to plasticity and synaptic transmission at many postsynaptic membranes. One of the most widely and thoroughly investigated forms of plasticity in the nervous system is known as long-term potentiation, or LTP. There are two necessary components of LTP: presynaptic glutamate release, and postsynaptic depolarization. Therefore, LTP can be induced experimentally in a paired electrophysiological recording when a presynaptic cell is stimulated to release glutamate on a postsynaptic cell that is depolarized. The typical LTP induction protocol involves a "tetanus" stimulation, which is a 100 Hz stimulation for 1 second. When one applies this protocol to a pair of cells, one will see a sustained increase of the amplitude of the excitatory postsynaptic potential (EPSP) following tetanus. This response is very intriguing because it is thought to be the physiological correlate for learning and memory in the cell. In fact, it was recently shown that, following a single paired-avoidance paradigm in mice, LTP could be recorded in some hippocampal synapses in vivo.

The molecular basis for LTP has been extensively studied, and AMPARs have been shown to play an integral role in the process. Both GluR1 and GluR2 play an important role in synaptic plasticity. It is now known that the underlying physiological correlate for the increase in EPSP size is a postsynaptic upregulation of AMPARs at the membrane, which is accomplished through the interactions of AMPARs with many cellular proteins.

The simplest explanation for LTP is as follows. Glutamate binds to postsynaptic AMPARs and another glutamate receptor, the NMDA receptor (NMDAR). Ligand binding causes the AMPARs to open, and Na+ flows into the postsynaptic cell, resulting in a depolarization. NMDARs, on the other hand, do not open directly because their pores are occluded at resting membrane potential by Mg2+ ions. NMDARs can open only when a depolarization from the AMPAR activation leads to repulsion of the Mg2+ cation out into the extracellular space, allowing the pore to pass current. Unlike AMPARs, however, NMDARs are permeable to both Na+ and Ca2+. The Ca2+ that enters the cell triggers the upregulation of AMPARs to the membrane, which results in a long-lasting increase in EPSP size underlying LTP. The calcium entry also phosphorylates CaMKII, which phosphorylates AMPARs, increasing their single-channel conductance.

Equally critical to synaptic plasticity is long-term depression (LTD), form of synaptic plasticity that involves the endocytosis of AMPARs. In LTD, AMPARs are dynamically regulated by changes in trafficking and channel function to express changes in synaptic efficacy. As such, LTD is a most relevant aspect of synaptic plasticity, and accordingly, particularly suited to modulation according to the methodologies of the instant invention.

Dopamine receptors are metabotropic G protein-coupled receptors that are widely expressed throughout the brain, and are important for learning and memory, as well as motivation, cognition, motor control, and pleasure. These receptors are activated by the neurotransmitter dopamine. Dopamine receptors are comprised of many subtypes (at least $D_1$-$D_5$). Aberrant dopamine receptor signaling has been implicated in many nervous system diseases, such as, but not limited to, attention-deficit hyperactivity disorder, Parkinson's disease, schizophrenia, Tourette's syndrome, social phobia, and drug and alcohol dependence. Dopamine receptors are also targets of antipsychotics (e.g., haloperidol) and stimulants (e.g., cocaine, heroin, amphetamine, alcohol, and nicotine).

E. Mdm2

Mdm2 is an important negative regulator of the p53 tumor suppressor. It is the name of a gene as well as the protein encoded by that gene. Mdm2 functions both as an E3 ubiquitin ligase that recognizes the N-terminal trans-activation domain (TAD) of the p53 tumor suppressor and an inhibitor of p53 transcriptional activation.

The murine double minute (MDM2) oncogene, which codes for the Mdm2 protein, was originally cloned, along with two other genes (MDM1 and MDM3) from the transformed mouse cell line 3T3-DM. The human ortholog of Mdm2 is Hdm2. Mdm2 overexpression, in cooperation with oncogenic Ras, promotes transformation of primary rodent fibroblasts, and mdm2 expression led to tumor formation in nude mice. The human homologue of this protein was later identified and is sometimes called Hdm2. Further supporting the role of mdm2 as an oncogene, several human tumor types have been shown to have increased levels of Mdm2, including soft tissue sarcomas and osteosarcomas as well as breast tumors. An additional Mdm2 family member, Mdm4 (also called MdmX), has been discovered and is also an important negative regulator of p53.

The key target of Mdm2 is the p53 tumor suppressor. Mdm2 has been identified as a p53 interacting protein that represses p53 transcriptional activity. Mdm2 achieves this repression by binding to and blocking the N-terminal transactivation domain of p53. Mdm2 is a p53 responsive gene—that is, its transcription can be activated by p53. Thus when p53 is stabilized, the transcription of Mdm2 is also induced, resulting in higher Mdm2 protein levels.

Mdm2 also acts as an E3 ubiquitin ligase, targeting both itself and p53 for degradation by the proteasome (see also Ubiquitin). Several lysine residues in p53 C-terminus have been identified as the sites of ubiquitination, and it has been shown that p53 protein levels are downregulated by Mdm2 in a proteasome-dependent manner. Mdm2 is capable of auto-polyubiquitination, and in complex with p300, a cooperating E3 ubiquitin ligase, is capable of polyubiquitinating p53. In this manner, Mdm2 and p53 are the members of a negative feedback control loop that keeps the level of p53 low in the absence of p53-stabilizing signals. This loop can be interfered with by kinases and genes like p14arf when p53 activation signals, including DNA damage, are high.

The full-length transcript of the mdm2 gene encodes a protein of 491 amino acids with a predicted molecular weight of 56 kDa. This protein contains several conserved structural domains including an N-terminal p53 interaction domain, the structure of which has been solved using x-ray crystallography. The Mdm2 protein also contains a central acidic domain (residues 230-300). The phosphorylation of residues within this domain appears to be important for regulation of Mdm2 function. In addition, this region contains nuclear export and import signals that are essential for proper nuclear-cytoplasmic trafficking of Mdm2. Another conserved domain within the Mdm2 protein is a Zinc finger domain, the function of which is poorly understood.

Mdm2 also contains a C-terminal RING domain (amino acid residues 430-480), which contains a Cis3-His2-Cis3 consensus that coordinates two molecules of zinc. These residues are required for zinc binding, which is essential for proper folding of the RING domain. The RING domain of Mdm2 confers E3 ubiquitin ligase activity and is sufficient for E3 ligase activity in Mdm2 RING autoubiquitination. The RING domain of Mdm2 is unique in that it incorporates a conserved Walker A or P-loop motif characteristic of nucleotide binding proteins, as well as a nucleolar localization sequence. The RING domain also binds specifically to RNA, although the function of this is poorly understood.

There are several known mechanisms for regulation of Mdm2. One of these mechanisms is phosphorylation of the Mdm2 protein. Mdm2 is phosphorylated at multiple sites in cells. Following DNA damage, phosphorylation of Mdm2 leads to changes in protein function and stabilization of p53. Additionally, phosphorylation at certain residues within the central acidic domain of Mdm2 may stimulate its ability to target p53 for degradation. The induction of the p14arf protein, the alternate reading frame product of the p16INK4a locus, is also a mechanism of negatively regulating the p53-Mdm2 interaction. p14arf directly interacts with Mdm2 and leads to upregulation of p53 transcriptional response. ARF sequesters Mdm2 in the nucleolus, resulting in inhibition of nuclear export and activation of p53, since nuclear export is essential for proper p53 degradation.

Levels and stability of Mdm2 are also modulated by ubiquitination. Mdm2 autoubiquitinates itself, which allows for its degradation by the proteasome. Mdm2 also interacts with a ubiquitin specific protease, USP7, which can reverse Mdm2-ubiquilyation and prevent it from being degraded by the proteasome. It is interesting to note that USP7 also protects from degradation the p53 protein, which is a major target of Mdm2. Thus Mdm2 and USP7 form an intricate circuit to finely regulate the stability and activity of p53, whose levels are critical for its function.

```
LOCUS           NP_002383             497 aa         linear        PRI 13 NOV. 2011
DEFINITION      E3 ubiquitin-protein ligase Mdm2 isoform MDM2 [Homo sapiens].
ACCESSION       NP_002383
VERSION         NP_002383.2  GI:89993689
DBSOURCE        REFSEQ: accession NM_002392.3
KEYWORDS        .
SOURCE          Homo_sapiens (human)
  ORGANISM      Homo_sapiens
source          1..497
                /organism="Homo sapiens"
                /db_xref="taxon:9606"
                /chromosome="12"
                /map="12q14.3-q15"
Protein         1..497
                /product="E3 ubiquitin-protein ligase Mdm2 isoform MDM2"
                /note="double minute 2, human homolog of; p53-binding
                protein; E3 ubiquitin-protein ligase Mdm2; MDM2 variant
                FB30; MDM2 variant FB28; oncoprotein Mdm2; Mdm2,
                transformed 3T3 cell double minute 2, p53 binding protein"
                /calculated_mol_wt=55860
Region          46..106
                /region name="SWIB"
                /note="SWIB/MDM2 domain; c102489"
                /db_xref="CDD:154937"
Site            166
                /site_type="phosphorylation"
                /experiment="experimental evidence, no additional details
                recorded"
                /citation=[6]
                /db_xref="HPRD:01261"
Site            172
                /site_type="phosphorylation"
                /experiment="experimental evidence, no additional details
                recorded"
                /citation=[9]
                /db_xref="HPRD:01261"
Site            188
                /site type="modified"
                /experiment="experimental evidence, no additional details
                recorded"
                /note="sumoylation site"
                /citation=[7]
                /db_xref="HPRD:03111"
Site            191
                /site_type="modified"
                /experiment="experimental evidence, no additional details
                recorded"
                /note="sumoylation site"
                /citation=[7]
                /db_xref="HPRD:03111"
Site            192
                /site_type="phosphorylation"
                /experiment="experimental evidence, no additional details
                recorded"
                /citation=[9]
                /db_xref="HPRD:01261"
Region          305..333
                /region name="zf-RanBP"
                /note="Zn-finger in Ran binding protein and others;
                c102656"
                /db_xref="CDD:198756"
Site            367
                /site_type="modified"
                /experiment="experimental evidence, no additional details
                recorded"
                /note="proteolytic cleavage site"
                /citation=[11]
                /db_xref="HPRD:02799"
```

```
Site            400
                /site_type="phosphorylation"
                /experiment="experimental evidence, no additional details
                recorded"
                /citation=[8]
                /db_xref="HPRD:01809"
Site            401
                /site_type="phosphorylation"
                /experiment="experimental evidence, no additional details
                recorded"
                /citation=[10]
                /db_xref="HPRD:06347"
Region          444..488
                /region_name="RING"
                /note="RING-finger (Really Interesting New Gene) domain, a
                specialized type of Zn-finger of 40 to 60 residues that
                binds two atoms of zinc; defined by the 'cross-brace'
                motif C-X2-C-X(9-39)-C-X(1-3)-
                H-X(2-3)-(N/C/H)-X2-C-X(4-48)C-X2-C; probably involved
                in...; cd00162"
                /db_xref="CDD:29102"
Site            order(444,447,461,463,467,470,481,484)
                /site_type="other"
                /note="cross-brace motif"
                /db_xref="CDD:29102"
CDS             1..497
                /gene="MDM2"
                /gene_synonym="hdm2; HDMX"
                /coded_by="NM_002392.3:288..1781"
                /note="isoform MDM2 is encoded by transcript variant MDM2"
                /db_xref="CCDS:CCDS8986.2"
                /db_xref="GeneID:4193"
                /db_xref="HGNC:6973"
                /db_xref="HPRD:01272"
                /db_xref="MIM:164785"

ORIGIN
   1   mvrsrqmcnt nmsvptdgav ttsqipaseq etlvrpkpll lkllksvgaq kdtytmkevl 61   fylgqyimtk rlydekqqhi vycsndllgd lfgvpsfsvk ehrkiytmiy rnlvvvnqqe 121   ssdsgtsyse nrchleggsd qkdlvqelge ekpssshlvs rpstssrrra iseteensde 181   lsgerqrkrh ksdsislsfd eslalcvire iccersssse stgtpsnpdl dagvsehsgd 241   wldqdsysdq fsvefevesl dsedyslsee ggelsdedde vyqvtvyqag esdtdsfeed 301   peisladywk ctscnemnpp lpshcnrcwa lrenwlpedk gkdkgeisek aklenstqae 361   egfdvpdckk tivndsresc veenddkitq asgsgesedy sqpstsssii yssqedvkef 421   ereetqdkee svesslpina iepcvicqgr pkngcivhgk tghlmacftc akklkkrnkp 481   cpvcrqpiqm ivltyfp//
```

Compounds that inhibit the enzymatic activity and/or substrate binding activity of Mdm2 and/or Mdm4 that are useful in the present invention include arylsulfonamides and/or enantiomers and/or derivatives thereof, bisarylureas and/or enantiomers and/or derivatives thereof, acylimidazolones and/or enantiomers and/or derivatives thereof, deazaflavins and/or enantiomers and/or derivatives thereof (e.g., HLI98 and HLI373), natural products and/or enantiomers and/or derivatives thereof (e.g., sempervirine and resveratrol), acridines and/or enantiomers and/or derivatives thereof, and JnJ-26854165 (serdemetan; as disclosed in Tabernero et al., Clin Cancer Res. 2011 Oct. 1; 17(19):6313-21). Non-limiting examples of compounds that inhibit substrate binding activity include benzodiazepinediones and/or enantiomers and/or derivatives thereof (e.g., TDP521252 and TDP665759), isoindoline compounds and/or enantiomers and/or derivatives thereof (e.g., those disclosed in US 2011/0224274, hereby incorporated by reference in its entirety), cis-imidazolines and/or enantiomers and/or derivatives thereof (e.g., Nutlin-1, Nutlin-2, Nutlin-3, Nutlin-3a), benzoylthioureas and/or enantiomers and/or derivatives thereof (e.g., tenovin-1 as described in EP2099445, herein incorporated by reference in its entirety), spiro-oxindoles and/or enantiomers and/or derivatives thereof (e.g., MI-43, MI-63, MI-219, and MI-319), thiophenes and/or enantiomers and/or derivatives thereof (e.g., RITA (NSC652287)). RO5045337 [RG7112], and RO5503781 are Nutlin compounds currently in clinical trials. Other nutlin compounds and derivatives thereof can be used in the present invention and are disclosed, e.g., in U.S. Pat. No. 7,893,278, hereby incorporated by reference in its entirety.

F. Mdm4

The human MDM4 gene (also known as MDMX), which plays a role in apoptosis, encodes a 490-amino acid protein containing a RING finger domain and a putative nuclear localization signal. The Mdm4 putative nuclear localization signal, which all Mdm proteins contain, is located in the C-terminal region of the protein. The mRNA is expressed at a high level in thymus and at lower levels in all other tissues tested. Mdm4 protein produced by in vitro translation interacts with p53 via a binding domain located in the N-terminal region of the Mdm4 protein. Mdm4 shows significant structural similarity to p53-binding protein Mdm2, and has been shown to ubiquitinate p53 in a RING-finger dependent manner (Badciong and Haas, 2002). Moreover, Mdm2 is expressed in neurons and is regulated by neurotoxic stimuli (Benosman et al., 2007).

```
LOCUS       NP_001191100     440 aa     linear    PRI 23 OCT. 2011
DEFINITION  protein Mdm4 isoform 2 [Homo sapiens].
ACCESSION   NP_001191100
VERSION     NP-001191100.1 GI:323510634
DBSOURCE    REFSEQ: accession NM_001204171.1
KEYWORDS    .
SOURCE      Homo sapiens (human)

Transcript Variant: This variant (2) lacks an in-frame coding exon
compared to variant 1, resulting in a shorter isoform (2) missing
an internal protein segment in the 3' coding region compared to
isoform 1.

Sequence Note: This RefSeq record was created from transcript and
genomic sequence data because no single transcript was available
for the full length of the gene. The extent of this transcript is
supported by transcript alignments.

Publication Note: This RefSeq record includes a subset of the
publications that are available for this gene. Please see the Gene
record to access additional publications.

FEATURES         Location/Qualifiers
  source         1..440
                 /organism="Homo sapiens"
                 /db_xref="taxon:9606"
                 /chromosome="1"
                 /map="1q32"
  Protein        1..440
                 /product="protein Mdm4 isoform 2"
                 /note="double minute 4, human homolog of; p53-binding
                 protein; MDM4-related protein 1; protein Mdmx; mdm2-like
                 p53-binding protein; Mdm4, transformed 3T3 cell double
                 minute 4, p53 binding protein"
                 /calculated mol wt=49410
  Region         26..101
                 /region name="SWIB"
                 /note="SWIB/MDM2 domain; c102489"
                 /db_xref="CDD:154937"
  Region         254..278
                 /region name="zf-RanBP"
                 /note="Zn-finger in Ran binding protein and others;
                 c102656"
                 /db_xref="CDD:198756"
  CDS            1..440
                 /gene="MDM4"
                 /gene_synonym="HDMX; MDMX; MRP1"
                 /coded_by="NM_001204171.1:167..1489"
                 /note="isoform 2 is encoded by transcript variant 2"
                 /db_xref="CCDS:CCDS55674.1"
                 /db_xref="GeneID:4194"
                 /db_xref="HGNC:6974"
                 /db_xref="MIM:602704"
```

```
               -continued
ORIGIN
    1 mtsfstsaqc stsdsacris pgqinqvrpk lpllkilhaa gaqgemftvk evmhylgqyi 61 mvkqlydqqe qhmvycggdl lgellgrqsf svkdpsplyd mlrknlvtla tattdaaqtl 121 alaqdhsmdi psqdqlkqsa eesstsrkrt teddiptlpt sehkcihsre dedlienlaq 181 detsrldlgf eewdvaglpw wflgnlrsny tprsngstdl qtnqvievgk nddledsksl 241 sddtdvevts edewqcteck kfnspskryc frcwalrkdw ysdcsklths lstsditaip 301 ekenegndvp dcrrtisapv vrpkdayikk ensklfdpcn svefldlahs sesqetissm 361 geqldnlseq rtdtenmedc qnllkpcslc ekrprdgnii hgrtghlvtc fhcarrlkka 421 gascpickke iqlvikvfia
//
```

G. Synaptic Plasticity

Synaptic plasticity is the ability of the connection, or synapse, between two neurons to change in strength. There are several underlying mechanisms that cooperate to achieve synaptic plasticity, including changes in the quantity of neurotransmitters released into a synapse and changes in how effectively cells respond to those neurotransmitters. Since memories are postulated to be represented by vastly interconnected networks of synapses in the brain, synaptic plasticity is one of the important neurochemical foundations of learning and memory.

There are two known molecular mechanisms for synaptic plasticity. The first mechanism involves modification of existing synaptic proteins (typically protein kinases) resulting in altered synaptic function. The second mechanism depends on second messenger neurotransmitters regulating gene transcription and changes in the levels of key proteins at synapses. This second mechanism can be triggered by protein phosphorylation but takes longer and lasts longer, providing the mechanism for long-lasting memory storage. Long-lasting changes in the efficacy of synaptic connections (long-term potentiation, or LTP) between two neurons can involve the making and breaking of synaptic contacts.

A synapse's strength also depends on the number of ion channels it has. Several facts suggest that neurons change the density of receptors on their postsynaptic membranes as a mechanism for changing their own excitability in response to stimuli. In a dynamic process that is maintained in equilibrium, N-methyl D-aspartate receptors (NMDA receptors) and alpha-amino-3-hydroxy-5-methyl-4-isoxazolepropionic acid receptors (AMPA receptors) are added to the membrane by exocytosis and removed by endocytosis. These processes, and by extension the number of receptors on the membrane, can be altered by synaptic activity. Experiments have shown that AMPA receptors are delivered to the membrane due to repetitive NMDA receptor activation.

If the strength of a synapse is only reinforced by stimulation or weakened by its lack, a positive feedback loop will develop, causing some cells never to fire and some to fire too much. But two regulatory forms of plasticity, called scaling and metaplasticity, also exist to provide negative feedback. Synaptic scaling serves to maintain the strengths of synapses relative to each other, lowering amplitudes of small excitatory postsynaptic potentials in response to continual excitation and raising them after prolonged blockage or inhibition. This effect occurs gradually over hours or days, by changing the numbers of NMDA receptors at the synapse (Pérez-Otaño and Ehlers, 2005). Metaplasticity, another form of negative feedback, reduces the effects of plasticity over time. Thus, if a cell has been affected by a lot of plasticity in the past, metaplasticity makes future plasticity less effective. Since LTP and LTD (long-term depression) rely on the influx of $Ca^{2+}$ through NMDA channels, metaplasticity may be due to changes in NMDA receptors, for example changes in their subunits to allow the concentration of $Ca^{2+}$ in the cell to be lowered more quickly.

H. Nervous System Disorders and Surface Expression of AMPARs, NMDARs, and D1 Dopamine Receptors Alzheimer's Disease Cognitive impairment in Alzheimer's disease (AD) correlates strongly with increased levels of soluble amyloid beta (Aβ) peptides and with alterations and loss of synapses (Lue et al., 1999; McLean et al., 1999; Shankar et al., 2008; DeKosky and Scheff, 1990; Terry et al., 1991; DeKosky et al., 1996; Masliah, 1997, Knobloch and Mansuy, 2008). Soluble Aβ peptides affect cognitive processes by depressing excitatory synaptic transmission and disrupting synaptic structure and function. A molecular correlate of Aβ-induced synaptic dysfunction is a decrease in the surface expression of glutamate AMPA- and NMDA-type receptors (Malinow and Malenka, 2002). Indeed, decreased levels of the AMPAR subunits GluA1 and GluA2/3 are observed in entorhinal cortex and hippocampal CA1 of AD brains (Geddes et al., 1992; Armstrong et al., 1994; Yasuda et al., 1995;

Ikonomovic et al., 1995; Carter et al., 2004) and in transgenic mouse models of AD (Cha et al., 2001; Almeida et al., 2005; Chang et al., 2006; Hsieh et al., 2006; Ting et al., 2007).

Several lines of evidence suggest that soluble Aβ peptides affect cognitive processes by depressing excitatory synaptic transmission and disrupting mechanisms of synaptic plasticity. Studies from many laboratories have shown that soluble oligomers of Aβ peptides disrupt synaptic structure (Lacor et al., 2004, 2007; Snyder et al., 2005; Hsieh et al., 2006; Chin et al., 2007; Shankar et al., 2007; Shughrue et al., 2010), impact synaptic plasticity (Lambert et al., 1998; Walsh et al., 2002; Wang et al., 2002; Townsend et al., 2006; Li et al., 2009), and induce memory deficits (Walsh et al, 2002; Cleary et al., 2005; Shankar et al., 2008). Aβ peptides are known to induce AMPAR endocytosis and Aβ-induced synapse loss and decreased dendritic spine density are accompanied by decreased AMPARs at the synapse (Almeida et al, 2005; Shankar et al., 2007).

One effect of Aβ on synapses is the internalization of AMPARs through a clathrin-dependent mechanism (Ehlers, 2000). Accordingly, pharmacological strategies that block Aβ-induced endocytosis of glutamate receptors may prevent the synaptic dysfunction and cognitive decline observed in AD. Since PSD-95 is major a scaffolding protein of glutamatergic synapses and interacts directly and indirectly with many membrane proteins such as neurotransmitter receptors, neurotrophic factors receptors, and adhesion molecules, the ubiquitination of PSD-95 by Mdm2, by promoting the association with the endocytic complex, may regulate the endocytosis of interacting neurotransmitter receptors, neurotrophic factors receptors, and adhesion molecules. Therefore, pharmacological strategies that block the ubiquitination of PSD-95 (e.g., Mdm2 and/or Mdm4 inhibitors or PSD-95 inhibitors) may impact any disorder in which glutamatergic synapses are affected, including, but not limited to, cognitive impairment, cognitive dysfunction, Alzheimer's disease, Parkinson's disease, dementia, autism, spectrum disorders, fragile-X syndrome, Down's syndrome, disorders affecting emotion, learning ability, and memory, schizophrenia, bipolar disorder, depression, major depressive disorder, anxiety disorders, attention-deficit hyperactivity disorder, and substance abuse.

II. Screening Methods

Based on the experiments described infra, Mdm2 and Mdm4 are targets for screening protocols, including protocols to screen for molecules that inhibit Mdm2 or Mdm4 binding to their respective substrates, as well as Mdm2 and/or Mdm4 E3 ligase activity. PSD-95, non-PSD-95 MAGUK proteins, and PSD-95 associated proteins are also targets for the screening protocols described infra. Candidate molecules identified in the screen with these activities are candidate drugs for use in the treatment of disorders of the nervous system, including neurological disorders, neurodevelopmental disorders, or psychiatric disorders.

A. Methods to Investigate Protein-Protein Interactions

Biochemical Methods

Many methods exist to assess protein-protein interactions. Each approach has its strengths and weaknesses, especially with regard to the sensitivity and specificity. High sensitivity means that many of the interactions that occur in reality are detected by the screen. High specificity indicates that most of the interactions detected by the screen are also occurring in reality.

Co-immunoprecipitation is considered the gold standard assay for protein-protein interactions, especially when it is performed with endogenous (not overexpressed and not tagged) proteins. The protein of interest is isolated with a specific antibody. Interaction partners which stick to this protein are subsequently identified by western blotting. Interactions detected by this approach are considered to be real. However, this method can only verify interactions between suspected interaction partners. Positive results may indicate that two proteins interact directly or may interact via one or more bridging molecules. This could include bridging proteins, nucleic acids (DNA or RNA), or other molecules.

Bimolecular fluorescence complementation (BiFC) is a new technique in observing the interactions of proteins. Combined with other new techniques, this method can be used to screen protein-protein interactions and their modulators, dual expression recombinase based (DERB).

Affinity electrophoresis is used to estimate binding constants, e.g., as in lectin affinity electrophoresis, or characterization of molecules with specific features like glycan content or ligand binding.

Pull-down assays are a common variation of immunoprecipitation and immunoelectrophoresis and are used identically, although this approach is more amenable to an initial screen for interacting proteins.

Label transfer can be used for screening or confirmation of protein interactions and can provide information about the interface where the interaction takes place. Label transfer can also detect weak or transient interactions that are difficult to capture using other in vitro detection strategies. In a label transfer reaction, a known protein is tagged with a detectable label. The label is then passed to an interacting protein, which can then be identified by the presence of the label.

The yeast two-hybrid screen investigates the interaction between artificial fusion proteins inside the nucleus of yeast. This approach can identify binding partners of a protein in an unbiased manner.

Phage display can be used for the high-throughput screening of protein interactions.

Photo-reactive amino acid analogs can be used to crosslink protein complexes in vivo. With this method, cells are grown with photoreactive diazirine analogs to leucine and methionine, which are incorporated into proteins. Upon exposure to ultraviolet light, the diazirines are activated and bind to interacting proteins that are within a few angstroms of the photo-reactive amino acid analog.

Tandem affinity purification (TAP) method allows high throughput identification of protein interactions. In contrast to yeast two-hybrid approach the accuracy of the method can be compared to those of small-scale experiments and the interactions are detected within the correct cellular environment as by co-immunoprecipitation. However, the TAP tag method requires two successive steps of protein purification and consequently cannot readily detect transient protein-protein interactions. Recent genome-wide TAP experiments were performed by Krogan et al. (2011) and Gavin et al. (2002), providing updated protein interaction data for yeast organism.

Chemical crosslinking is often used to "fix" protein interactions in place before trying to isolate/identify interacting proteins. Common crosslinkers for this application include the non-cleavable NHS-ester crosslinker, bissulfosuccinimidyl suberate (BS3); a cleavable version of BS3, dithiobis(sulfosuccinimidyl propionate) (DTSSP); and the imidoester crosslinker dimethyl dithiobispropionimidate (DTBP) that is popular for fixing interactions in chromatin immunoprecipitation (ChIP) assays.

Chemical crosslinking followed by high mass matrix-assisted laser desorption/ionization (MALDI) mass spectrometry can be used to analyze intact protein interactions in place before trying to isolate/identify interacting proteins. This method detects interactions among non-tagged proteins and is available from CovalX.

SPINE (Strep-protein interaction experiment) uses a combination of reversible crosslinking with formaldehyde and an incorporation of an affinity tag to detect interaction partners in vivo.

Quantitative immunoprecipitation combined with knockdown (QUICK) relies on co-immunoprecipitation, quantitative mass spectrometry (SILAC) and RNA interference (RNAi). This method detects interactions among endogenous non-tagged proteins. Thus, it has the same high confidence as co-immunoprecipitation. However, this method also depends on the availability of suitable antibodies.

Biophysical and Theoretical Methods

Dual polarization interferometry (DPI) can be used to measure protein-protein interactions. DPI provides real-time, high-resolution measurements of molecular size, density and mass. While tagging is not necessary, one of the protein species must be immobilized on the surface of a waveguide. As well as kinetics and affinity, conformational changes during interaction can also be quantified.

Static light scattering (SLS) measures changes in the Rayleigh scattering of protein complexes in solution and can non-destructively characterize both weak and strong interactions without tagging or immobilization of the protein. The measurement consists of mixing a series of aliquots of different concentrations or compositions with the anylate, measuring the effect of the changes in light scattering as a result of the interaction, and fitting the correlated light scattering changes with concentration to a model. Weak, non-specific interactions are typically characterized via the second virial coefficient. This type of analysis can determine the equilibrium association constant for associated complexes.

Dynamic light scattering (DLS), also known as quasielastic light scattering (QELS), or photon correlation spectroscopy, processes the time-dependent fluctuations in scattered light intensity to yield the hydrodynamic radius of particles in solution. The hydrodynamic radius is the radius of a solid sphere with the same translational diffusion coefficient as that measured for the sample particle. As proteins associate, the average hydrodynamic radius of the solution increases. Application of the Method of Continuous Variation, otherwise known as the Job plot, with the solution hydrodynamic radius as the observable, enables in vitro determination of Kd, complex stoichiometry, complex hydrodynamic radius, and the $\Delta H°$ and $\Delta S°$ of protein-protein interactions. This technique does not entail immobilization or labeling. Transient and weak interactions can be characterized. Relative to static light scattering, which is based upon the absolute intensity of scattered light, DLS is insensitive to background light from the walls of containing structures. This insensitivity permits DLS measurements from 1 µL volumes in 1536 well plates, and lowers sample requirements into the femtomolar range. This technique is also suitable for screening of buffer components and/or small molecule inhibitors/effectors.

Surface plasmon resonance can be used to measure protein-protein interaction.

Fluorescence polarization/anisotropy can be used to measure protein-protein or protein-ligand interactions. Typically one binding partner is labeled with a fluorescence probe (although sometimes intrinsic protein fluorescence from tryptophan can be used) and the sample is excited with polarized light. The increase in the polarization of the fluorescence upon binding of the labeled protein to its binding partner can be used to calculate the binding affinity.

With fluorescence correlation spectroscopy, one protein is labeled with a fluorescent dye and the other is left unlabeled. The two proteins are then mixed and the data outputs the fraction of the labeled protein that is unbound and bound to the other protein, allowing you to get a measure of KD and binding affinity. You can also take time-course measurements to characterize binding kinetics. Fluorescence correlation spectroscopy (FCS) also tells you the size of the formed complexes so you can measure the stoichiometry of binding. A more powerful method is fluorescence cross-correlation spectroscopy (FCCS) that employs double labeling techniques and cross-correlation resulting in vastly improved signal-to-noise ratios over FCS. Furthermore, the two-photon and three-photon excitation practically eliminates photobleaching effects and provides ultra-fast recording of FCCS or FCS data.

Fluorescence resonance energy transfer (FRET) is a common technique when observing the interactions of only two different proteins.

Protein activity determination by nuclear magnetic resonance (NMR) multi-nuclear relaxation measurements, or 2D-FT NMR spectroscopy in solutions, combined with nonlinear regression analysis of NMR relaxation or two-dimensional fourier transform (2D-FT) spectroscopy data sets. Whereas the concept of water activity is widely known and utilized in the applied biosciences, its complement—the protein activity which quantitates protein-protein interactions—is much less familiar as it is more difficult to determine in dilute solutions of proteins; protein activity is also much harder to determine for concentrated protein solutions when protein aggregation, not merely transient protein association, is often the dominant process.

Theoretical modeling of protein-protein interactions involves a detailed physical chemistry/thermodynamic understanding of several effects involved, such as intermolecular forces, ion-binding, proton fluctuations and proton exchange. The theory of thermodynamically linked functions is one such example in which ion-binding and protein-protein interactions are treated as linked processes; this treatment is especially important for proteins that have enzymatic activity which depends on cofactor ions dynamically bound at the enzyme active site, as for example, in the case of oxygen-evolving enzyme system (OES) in photosynthetic biosystems where the oxygen molecule binding is linked to the chloride anion binding as well as the linked state transition of the manganese ions present at the active site in Photosystem II (PSII). Another example of thermodynamically linked functions of ions and protein activity is that of divalent calcium and magnesium cations to myosin in mechanical energy transduction in muscle. Last but not least, chloride ion and oxygen binding to hemoglobin (from several mammalian sources, including human) is a very well-known example of such thermodynamically linked functions for which a detailed and precise theory has been already developed.

Molecular dynamics (MD) computations of protein-protein interactions can also be used.

Protein-protein docking, the prediction of protein-protein interactions based only on the three-dimensional protein structures from X-ray diffraction of protein crystals might not be satisfactory.

Isothermal Titration calorimetry (ITC) can be used to measure protein-protein interactions. ITC provides information regarding the stoichiometry, enthalpy, entropy, and binding kinetics between two interacting proteins.

B. Methods for Identifying Novel Mdm2 and/or Mdm4 Inhibitors

The invention provides methods for identifying compounds for the treatment of a neurological disorder, neurodevelopmental disorder, or psychiatric disorder. In one embodiment, the identification of a suitable compound, and/or enantiomer and/or derivatives thereof, is based on an observed decrease in the E3 ubiquitin ligase activity of Mdm2 and/or Mdm4, or a decrease in the level of binding to a synaptic or non-synaptic substrate protein. Inhibition of enzymatic activity can be on the order of at least 10%, or preferably at least 20%, or more preferably at least 30%, or even more preferably at least 40%, or even more preferably at least 50%, or even more preferably at least 60%, or even more preferably at least 70%, or even more preferably at least 80%, or even more preferably at least 90%, or even more preferably at least 95% of enzymatic activity. Inhibition of the interaction or binding between Mdm2 and/or Mdm4 and PSD-95, non-PSD-95 MAGUK proteins, and/or PSD-95 associated proteins is at least 10%, or preferably at least 20%, or more preferably at least 30%, or even more preferably at least 40%, or even more preferably at least 50%, or even more preferably at least 60%, or even more preferably at least 70%, or even more preferably at least 80%, or even more preferably at least 90%, or even more preferably at least 95% of the interaction or binding. Methods to determine the extent of inhibition of enzymatic activity (e.g., E3 ubiquitin ligase activity) or interaction or binding are described infra. The substrate protein can be, for example, a synaptic or non-synaptic protein (e.g., p53, PSD-95, non-PSD-95 MAGUK proteins such as SAP97, SAP102, PSD-93, PSD-95-associated proteins).

The following assays and screens can be used to identify compounds and/or enantiomers and/or derivatives thereof that are inhibitors of Mdm2 and/or Mdm4 activity or inhibitors of the interaction between Mdm2 and/or Mdm4 with their respective substrates (herein, "Mdm2 inhibitor" and/or "Mdm4 inhibitor"). The assays and screens can be carried out through physical selection of agents or molecules from libraries (e.g., small molecule libraries), and computer comparisons of digital models of compounds in molecular libraries and a digital model of the active site of Mdm2 and/or Mdm4. Molecules known to inhibit the activity of Mdm2 and/or Mdm4, or their binding to substrates (e.g., Nutlin-3a, HLI-373) can serve as lead compounds for further modification using art-recognized techniques, to develop more potent inhibitors. The inhibitors identified in the assays and screens may act by, but are not limited to, binding to Mdm2 and/or Mdm4 or interfering with the interaction between Mdm2 and/or Mdm4 with its substrates.

Compounds and/or enantiomers and/or derivatives thereof that can be screened by the methods described herein include, but are not limited to, peptides and other organic compounds (e.g., peptidomimetics) that bind to Mdm2 and/or Mdm4 or inhibit their activities in any way. Such compounds may include, but are not limited to, peptides; for example, soluble peptides, including but not limited to members of random peptide libraries (see, e.g., Lam et al., Nature 354:82-84, 1991; Houghten et al., Nature 354:84-86, 1991), and combinatorial chemistry-derived molecular libraries made of D- and/or L-amino acids, phosphopeptides (including, but not limited to, members of random or partially degenerate, directed phosphopeptide libraries; see, e.g., Songyang et al., Cell 72:767-778, 1993), and small organic or inorganic molecules.

Compounds and molecules can be screened to identify those that affect the activity of Mdm2 and/or Mdm4 proteins (e.g., by inhibiting Mdm2 and/or Mdm4 activity) or the activity of a molecule involved in regulating Mdm2 and/or Mdm4 activity. Such compounds or molecules are not limited to those that directly bind to Mdm2 and/or Mdm4, but also include those that indirectly inhibit Mdm2 and/or Mdm4 activity by binding to and inhibiting, e.g., an interacting partner required for Mdm2 and/or Mdm4 activity.

Computer modeling or searching technologies are used to identify compounds, or identify modified compounds, that modulate or are candidates to modulate the activity or substrate binding affinity of Mdm2 and/or Mdm4. For example, compounds likely to interact with the active site of Mdm2 and/or Mdm4 protein can be identified. The active site of Mdm2 has been well characterized in the art (McCoy et al., PNAS 2003; 100:1645-48; Chène, 2004; Hu and Hu, 2008; Moll and Petrenko, 2003; Shumizu and Hupp, 2003).

The active site of Mdm4 can be identified using methods known in the art including, e.g., analysis of the amino acid sequence of the Mdm4, and from a study of complexes formed by Mdm4 and its native substrates. Chemical or X-ray crystallographic methods can be used to identify the active site of Mdm4 by the location of bound ligand (which can be identified and/or screened for using art-recognized methods).

The three-dimensional structure of the active site of Mdm4 can also be determined using known methods, such as X-ray crystallography, which can be used to determine a complete molecular structure. Solid or liquid phase NMR can be used to determine certain intra-molecular distances. Other methods of structural analysis can be used to determine partial or complete geometrical structures. Geometric structure can be determined with Mdm4 bound to a natural or artificial ligand (which can be identified and/or screened for using art-recognized methods) which may provide a more accurate active site structure determination. Computer-based numerical modeling can be used to complete an incomplete or insufficiently accurate structure. Modeling methods that can be used are, e.g., parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups are necessary, and can be selected from force fields known in physical chemistry. Information on incomplete or less accurate structures determined as above can be incorporated as constraints on the structures computed by these modeling methods.

Having determined the structure of the active site of Mdm4, either experimentally, by modeling, or by a combination of methods, or using the known active site of the Mdm2 protein, candidate modulating compounds can be identified by searching databases containing compounds along with information on their molecular structure. The compounds identified in such a search are those that have structures that match the active site structure, fit into the active site, or interact with groups defining the active site. The compounds identified by the search are potential Mdm2 and/or Mdm4 inhibitors.

These methods may also be used to identify improved Mdm2 and/or Mdm4 inhibitors from an already known inhibiting compound or ligand. The structure of the known compound is modified and effects are determined using experimental and computer modeling methods as described herein. The altered structure is compared to the active site structure of Mdm2 and/or Mdm4 to determine or predict how a particular modification to the ligand or modulating compound will affect its interaction with that protein. Systematic variations in composition, such as by varying side groups, can be evaluated to obtain modified modulating compounds or ligands of preferred specificity or activity.

Given the teachings herein, additional experimental and computer modeling methods useful to identify Mdm2 and/or Mdm4 inhibitors based on the known active site of Mdm2 or identification of the active site of Mdm4 can be developed by those skilled in the art.

Examples of molecular modeling systems are the QUANTA programs, e.g., CHARMm, MCSS/HOOK, and X-LIGAND, (Molecular Simulations, Inc., San Diego, Calif.). QUANTA provides a modeling environment for two dimensional and three dimensional modeling, simulation, and analysis of macromolecules and small organics. Specifically, CHARMm analyzes energy minimization and molecular dynamics functions. MCSS/HOOK characterizes the ability of an active site to bind a ligand using energetics calculated via CHARMm. X-LIGAND fits ligand molecules to electron density patterns of protein-ligand complexes. The program also allows interactive construction, modification, visualization, and analysis of the behavior of molecules with each other.

Articles reviewing computer modeling of compounds interacting with specific proteins can provide additional guidance. For example, see, Rotivinen et al., Acta Pharmaceutical Fennica 97:159-166, 1988; Ripka, New Scientist 54-57 (Jun. 16, 1988); McKinaly and Rossmann, Ann. Rev. Pharmacol. Toxicol. 29:111-122, 1989; Perry and Davies, OSAR: Quantitative Structure-Activity Relationships in Drug Design pp. 189-193 (Alan R. Liss, Inc., 1989); Lewis and Dean, Proc. R. Soc. Lond. 236:125-140, 141-162, 1989; and, regarding a model receptor for nucleic acid components, see Askew et al., Am. J. Chem. Soc. 111:1082-1090. Computer programs designed to screen and depict chemicals are available from companies such as MSI (supra), Allelix, Inc. (Mississauga, Ontario, Canada), and Hypercube, Inc. (Gainesville, Fla.). These applications are largely designed for drugs specific to particular proteins; however, they may be adapted to the design of drugs specific to identified regions of DNA or RNA. Commercial sources of candidate compounds include ArQule, Inc. (Medford, Mass.).

In addition to designing and generating compounds that alter binding, as described above, libraries of known compounds, including natural products, synthetic chemicals, and biologically active materials including peptides, can be screened for compounds that inhibit Mdm2 and/or Mdm4 activity.

Compounds identified by methods described above may be useful, for example, for elaborating the biological functions of Mdm2 or Mdm4, and in treatment of nervous system disorders, e.g., neurological disorders, neurodevelopmental disorders, or psychiatric disorders, in which Mdm2 or Mdm4 activity is deleterious. Assays for testing the effectiveness of compounds such as those described herein are further described below.

C. In Vitro Assays to Screen for Compounds that Inhibit Mdm2 and/or Mdm4 Enzymatic Activity Candidate compounds and/or molecules and/or enantiomers and/or derivatives thereof that inhibit the enzymatic activity of Mdm2 and/or Mdm4 can readily be screened for using, e.g., in vitro assays. Such assays can include, but are not limited to, in vitro ubiquitination assays. These assays are well-characterized in the art, and have been carried out for Mdm2 and Mdm4 (e.g., Li et al., *JBC* 2002; 277:50607-11; Kitagaki et al., 2008; Badciong and Haas, 2002). By way of example, these assays include in vitro ubiquitination assays with purified proteins (e.g., recombinant ubiquitin, substrate, and E1, E2, and E3 enzymes) in an appropriate buffer (with an energy source) that allows for ubiquitination to occur, in the presence or absence of a test compound. The mixture can then be separated by gel electrophoresis (e.g., sodium dodecyl sulfate polyacrylamide gel electrophoresis (SDS-PAGE)), followed by visualization of ubiquitinated species by, e.g., Western blot analysis, or, in the case of radiolabeled substrate, radiography. Inhibition of Mdm2 enzymatic activity by a test compound in this context refers to a decrease in the extent of ubiquitination of a synaptic or non-synaptic substrate protein (e.g., PSD-95, non-PSD-95 MAGUK proteins, PSD-95-associated proteins, p53) by at least 10%, at least 20%, at least 30%, at least 40%, at least 50%, at least 60%, at least 70%, at least 80%, at least 90%, or at least 95%, in comparison to a reaction carried out in the absence of the compound or in the presence of a compound that does not inhibit Mdm2 activity. Preferably, the decrease in Mdm2 activity is greater than 25%, or preferably greater than 50%, or more preferably greater than 75%, or even more preferably greater than 90%. It is well within the abilities of one of ordinary skill to design, optimize, and carry out similar assays for Mdm4. In vitro ubiquitination assays can also be carried out in cell lines or primary cells. Such assays can involve, for example, treating cells with a stimulus known to induce ubiquitination of a substrate protein (e.g., Aβ as described in the Examples infra) in the presence or absence of a test compound, lysing the cells in an appropriate extraction buffer, immunoprecipitating the target substrate (e.g., p53, PSD-95, non-PSD-95 MAGUK proteins such as SAP97, SAP102, PSD-93, PSD-95-associated proteins), running immunoprecipitates on an agarose gel (e.g., SDS-PAGE), followed by Western blot analysis using commercially available ubiquitin antibodies. Aβ peptide is commercially available (e.g., rPeptide, Bogart, G A). Ubiquitin antibodies used can be those that specifically recognize poly-ubiquitinated proteins (e.g., FK1 antibody; Biomol/ENZO Life Sciences), or those that do not discriminate between mono- and poly-ubiquitinated proteins (e.g., FK2 antibody; Biomol/ENZO Life Sciences). The extent of inhibition of Mdm2 activity can be visualized by a decrease in the extent of ubiquitination, preferably mono-ubiquitination, or a decrease in signal intensity of the ubiquitination ladder that forms, which represents poly-ubiquitinated species of the immunoprecipitated substrate. Inhibition of Mdm2 enzymatic activity by a test compound in this context refers to a decrease in the extent of ubiquitination of a substrate protein (e.g., PSD-95, non-PSD-95 MAGUK protein, PSD-95-associated proteins, p53, and the like) by at least 10%, or at least 20%, or at least 30%, or at least 40%, or at least 50%, or at least 60%, or at least 70%, or at least 80%, or at least 90%, or at least 95%, in comparison to a reaction carried out in the absence of the compound or in the presence of a compound that does not inhibit Mdm2 activity. Such assays are described in, e.g., Kitagaki et al., 2008).

D. In Vitro Assays to Screen for Mdm2 and/or Mdm4 Binding Compounds

Compounds and/or enantiomers and/or derivatives thereof that interact with or bind to Mdm2 and/or Mdm4 can be identified using in vitro assays. Such compounds may be useful, for example, for decreasing the enzymatic activity of Mdm2 and/or Mdm4, inhibiting the interaction between Mdm2 and/or Mdm4 and binding partners (e.g., p53, PSD-95, non-PSD-95 MAGUK protein such as SAP97, SAP102, PSD-93, PSD-95-associated proteins), or treating disorders caused or exacerbated by Mdm2 and/or Mdm4 activity.

Assays for identifying compounds that interact with or bind to Mdm2 and/or Mdm4 involve preparation of a reaction mixture of the protein and the test compound under conditions sufficient to allow the two components to interact and bind, thus forming a complex that can be detected and/or isolated.

Numerous methods are known in the art that can be applied to screening for molecules that can interact with or bind to Mdm2 and/or Mdm4. For example, Mdm2 and/or Mdm4, a peptide thereof, or fusion proteins thereof can be immobilized onto a solid phase, reacted with the test compound, and complexes detected by direct or indirect labeling of the test compound. Alternatively, the test compound can be immobilized, reacted with Mdm2 and/or Mdm4 polypeptide, and any complexes detected. Microtiter plates can be used as the solid phase and the immobilized component anchored by covalent or noncovalent interactions. Non-covalent attachment may be achieved by coating the solid phase with a solution containing the molecule, and drying. Alternatively, an antibody specific for Mdm2 and/or Mdm4 is used to anchor the molecule to the solid surface. Such surfaces may be prepared in advance of use, and stored. Mdm2 and Mdm4 antibodies can be produced using conventional methods such as those described in Coligan et al. (Current Protocols in Immunology, John Wiley & Sons, Inc., 1994, see Volume 1, chapter 2). In the assay, the non-immobilized component is added to the coated surface containing the immobilized component under conditions that permit interaction and binding between the two components. The unreacted components are then washed away under conditions such that any complexes formed will remain immobilized on the solid phase. The detection of the complexes can be accomplished by art-recognized methods. For example, the nonimmobilized component of the assay may be prelabeled with a radioactive or enzymatic label and detected using appropriate means. If the non-immobilized entity was not prelabeled, an indirect method is used. For example, if the non-immobilized entity is Mdm2 and/or Mdm4, an antibody the respective protein can be used to detect the bound molecule, and a secondary, labeled antibody is used to detect the entire complex. Alternatively, a reaction can be conducted in a liquid phase, the reaction products separated from unreacted components, and complexes detected (e.g., using an immobilized antibody specific for Mdm2 and/or Mdm4). Such methods can be adapted to larger scale high-throughput screens for compounds that interact with or bind to Mdm2 and/or Mdm4.

Cell-based assays can be used to identify compounds that interact with or bind to Mdm2 and/or Mdm4. Cell lines that naturally express such proteins or have been genetically engineered to express such proteins (e.g., by transfection or transduction with expression vectors for Mdm2 and/or Mdm4 of, e.g., mammalian origin) can be used. Test compounds can be added to cell cultures and the expression of or extent of ubiquitination of known Mdm2 and/or Mdm4 substrates can be assessed using art recognized techniques (e.g., Western blot, Enzyme-linked immunosorbent assay (ELISA)). A decrease in the amount of expression of, e.g., a Mdm2 substrate (e.g., p53) in the presence of a test compound indicates that the test compound is an Mdm2 inhibitor (i.e., an inhibitor of Mdm2 E3 ligase activity). For ubiqutination events that do not alter the expression of a substrate, e.g., monoubiquitination, a decrease in the amount of monoubiquitination of, e.g., a Mdm2 substrate (e.g., PSD-95), in the presence of a test compound also indicates that the test compound is an Mdm2 inhibitor and thus is a candidate for use in the treatment of disorders associated with aberrant surface expression of AMPARs, NMDARs, and/or D1 dopamine receptors.

E. Assays for Compounds that Disrupt Interactions Between Mdm2 or Mdm4 and their Respective Substrates Art-recognized methods can also be used to screen for and/or confirm compounds and/or enantiomers and/or derivatives thereof that disrupt the interaction between Mdm2 or Mdm4 and their respective substrates (e.g., synaptic or non-synaptic proteins such as PSD-95, non-PSD-95 MAGUK proteins, PSD-95-associated proteins, p53). Such methods include assays that detect protein-protein interactions described supra and in the Examples (e.g., coimmunoprecipitation assays). For instance, Mdm2 immobilized to a support (e.g., agarose beads) can be incubated with a sample containing a known binding partner for Mdm2 (e.g., p53, PSD-95) in the presence or absence of a test molecule or compound. Such assays need not involve purified components, and can be carried out using whole cell extracts. For example, primary cells (e.g., neurons) or cell lines can be cultured in the presence or absence of a candidate Mdm2 and/or Mdm4 inhibitor. This step can also include a treatment with a drug (e.g., NMDA, Aβ known to promote the interaction between Mdm2 or Mdm4 with a binding protein or substrate (e.g., p53, PSD-95, non-PSD-95 MAGUK proteins such as SAP97, SAP102, PSD-93, PSD-95-associated proteins). After the treatments, whole cell extracts can be prepared from the treated cells, from which Mdm2 can be immunoprecipitated. This step can be followed by, e.g., Western blot analysis to examine the degree of interaction with known binding partners or substrates. A candidate Mdm2 and/or Mdm4 inhibitor is identified when the interaction between Mdm2 and/or Mdm4 with the known binding partner is decreased in the presence of the test compound or molecule compared to a control compound or molecule (e.g., vehicle treatment or a compound without affinity for Mdm2 and/or Mdm4). In general, the test molecule is tested over a range of a 100 fold molar excess over the most abundant component (e.g., the component immobilized or in solution). If the test molecule is predicted to interact with the immobilized component of the assay, then it can be pre-incubated with that component before adding the cell lysate or purified protein. After washing away unbound material, the bound proteins are detected with antibodies (e.g., ELISA or Western blot) or through the use of labeled proteins (e.g. radioactive or fluorescent) using methods known in the art. Test molecules that decrease the amount of substrate bound to Mdm2 and/or Mdm4 are thus molecules that interfere with Mdm2/Mdm2 substrate and/or Mdm4/Mdm4 substrate interactions.

F. PSD-95 Inhibitors and Assays to Identify PSD-95 Inhibitors

With respect to PSD-95 inhibitors, and/or enantiomers and/or derivatives thereof, such inhibitors (e.g., inhibitory peptides) can be used in any situation in which inhibition of the interaction between PSD-95 and its interacting proteins is beneficial, e.g., as in the methods of the present invention. In a preferred embodiment, the PSD-95 inhibitor inhibits the interaction between PSD-95 and Mdm2 and/or Mdm4, thereby preventing PSD-95 monoubiquitination, and consequently increasing surface AMPAR, NMDAR, and/or D1 dopamine receptor expression. In yet other embodiments, PSD-95 inhibitors (e.g., PSD-inhibitory peptides) bind to or interact with PSD-95 and thereby disrupt PSD-95 binding with interacting proteins.

The PSD-95 inhibitors can be obtained or produced using art-recognized methods, e.g., genetic engineering, chemical synthesis, peptide synthesizer. In one embodiment, the candidate PSD-95 inhibitor can be a peptide mimetic, in which up to 20, or up to 15, or up to 10, or up to 5 peptide bonds have been replaced with an alternative type of covalent bond that is not susceptible to cleavage by peptidases. Particularly in instances where proteolytic degradation upon administration to a mammal is an issue, sensitive peptide bonds can be replaced with a non-cleavable peptide mimetic renders the peptide more stable. Such mimetics, and methods of introducing them into peptides, are well known in the art.

The present invention also encompasses nucleic acids that encode PSD-95 inhibitors (e.g., inhibitory peptides). Such nucleic acids can be readily obtained using art-recognized methods, such as polymerase chain reaction (PCR) amplification. For recombinant expression of the PSD-95 inhibitory peptides, the nucleic acid sequence encoding the peptide can be inserted into an appropriate expression vector (with regulatory elements required for transcription and translation) known in the art. The expression vector can be, e.g., a mammalian expression vector, bacterial expression vector, viral expression vector, baculovirus expression vector, and the like. The regulatory elements of the expression vector can be such that it promotes the expression of the PSD-95 inhibitory peptide in a cell-specific, or tissue-specific, manner. Such regulatory elements are well known in the art. PSD-95 inhibitory peptides can be delivered to cells using, e.g., a viral delivery system (e.g., herpes simplex virus, lentivirus, adenovirus, adeno-associated virus), or can be rendered cell permeable by fusing with a cell penetrating sequence (e.g., HIV TAT peptide on the N- or C-terminus).

Also contemplated in the invention are host cell strains engineered to express nucleic acids encoding the PSD-95 inhibitory peptide. Such nucleic acids may be episomal or integrate into the host cell genome. The nucleic acids are transcribed and translated by the host cell transcriptional and translational machinery. Appropriate cell lines or host systems may be chosen to ensure the desired modification and processing of the PSD-95 inhibitory peptide is achieved. In one embodiment, a bacterial expression vector including the coding sequence of a PSD-95 inhibitory peptide is introduced into bacteria, and recombinant PSD-95 inhibitory peptide is subsequently affinity purified from bacterial lysates using art-recognized methods.

Use of the term "peptide" does not imply a size limit to the number of amino acids in the peptide. In one embodiment, the PSD-95 inhibitory peptide spans the entire PSD-95 amino acid sequence. In other embodiments, the peptide is less than 700, 650, 600, 550, 500, 450, 400, 350, 300, 250, 200, 150, 100, 50, 25, or 10 amino acids in length. Accordingly, in some embodiments, the PSD-95 inhibitory peptide may contain more amino acids than native PSD-95 when, e.g., fused to a cell penetrating sequence (e.g., HIV TAT). In some embodiments, the peptide will comprise a stretch of amino acids that is identical, or substantially homologous, to a stretch of amino acids in native mammalian PSD-95. PSD-95 amino acid sequences of various mammalian species are known in the art. In other embodiments, the stretch of amino acids that is identical, or substantially homologous, to the native PSD-95 amino acid sequence spans the entire PSD-95 amino acid sequence. In yet other embodiments, the stretch of amino acids that is identical, or substantially homologous, to native PSD-95 is less than 700, 650, 600, 550, 500, 450, 400, 350, 300, 250, 200, 150, 100, 50, 25, or 10 amino acids in length. In some embodiments, the peptide has an amino acid identity to mammalian PSD of at least 70%, or preferably at least 75%, or more preferably at least 80%, or even more preferably at least 85%, or even more preferably at least 90%, or even more preferably at least 95%, in the stretch of amino acids that is homologous to the stretch of amino acids in native PSD-95 (i.e., excluding any exogenously added sequences, e.g., HIV TAT trafficking sequence).

PSD-95 inhibitors and/or enantiomers and/or derivatives thereof of the present invention that serve to disrupt the binding between endogenous PSD-95 and its interacting proteins are exemplified by amino acid sequences that are identical, or substantially homologous, to regions of PSD-95 that are important for PSD-95 function. Accordingly, in one embodiment, PSD-95 inhibitory peptides comprise amino acid sequences of regions known to be important for binding between PSD-95 and its interacting proteins. In many cases, the interaction domains are known in the art. In some embodiments, potential inhibitory peptides can be identified by initially mapping interaction domains between PSD-95 and its interacting proteins using art-recognized methods. Once the interaction domain with a target interacting protein has been mapped, the mapped domain alone can be expressed using methods described supra and tested for its inhibitory effect on the binding between PSD-95 and target interacting protein. Peptides that inhibit the binding between endogenous PSD-95 and a target interacting protein are candidate PSD-95 inhibitory peptides. Candidate PSD-95 inhibitory peptides can be tested for the ability to increase surface expression of AMPAR, NMDAR, and/or D1 dopamine receptors using assays described infra. In a preferred embodiment, the PSD-95 inhibitory peptide comprises the PSD-95-Mdm2 and/or PSD-95-Mdm4 interaction domain. The skilled artisan will recognize that substantially homologous variations of the PSD-95 inhibitory peptide will also disrupt binding between endogenous PSD-95 and its target interacting protein.

PSD-95 inhibitory peptides of the present invention that bind to or interact with PSD-95 can be identified using art-recognized methods, including, but not limited to, direct binding assays with peptide libraries as described supra. Once identified, such candidate PSD-95 inhibitory peptides can be tested for efficacy using assays described infra.

Other PSD-95 inhibitors can be identified using the methods described for Mdm2 and Mdm4 supra. Such compounds may include, but are not limited to, peptides; e.g., soluble peptides, including but not limited to members of random peptide libraries (see, e.g., Lam et al., Nature 354:82-84, 1991; Houghten et al., Nature 354:84-86, 1991), and combinatorial chemistry-derived molecular libraries made of D- and/or L-amino acids, phosphopeptides (including, but not limited to, members of random or partially degenerate, directed phosphopeptide libraries; see, e.g., Songyang et al., Cell 72:767-778, 1993), and small organic or inorganic molecules. Methods known in the art for peptidomimetic approaches to modulate the p53-Mdm2 interaction can be adapted to the screens of the present invention (e.g., peptidomimetic approaches to screen for compounds (e.g., peptide, peptidomimetic, small-molecule antagonists) that inhibit the interaction of Mdm2 and/or Mdm4 with PSD-95, non-PSD-95 MAGUK proteins, and PSD-95 associated proteins) and are described in, e.g., Fisher, 2006; Hardcastle, 2007, and Murray 2007.

The skilled artisan would appreciate that non-PSD-95 MAGUK protein and/or PSD-95-associated protein inhibitors can readily be identified using the methods described supra for PSD-95 and tested for efficacy using the assays described infra.

III. Assays to Assess the Efficacy of Mdm2 and/or Mdm4 Inhibitors, or PSD-95 Inhibitors Candidate compounds and/or enantiomers and/or derivatives thereof that have been identified by the in vitro methods described supra, test compounds that are predicted to inhibit Mdm2 and/or Mdm4 activity and/or interactions with binding partners or substrates (e.g., p53, PSD-95, non-PSD-95 MAGUK proteins such as SAP97, SAP102, PSD-93, PSD-95-associated proteins), and/or PSD-95 inhibitors are administered to animals, e.g., as described infra, that serve as models for various disease paradigms. Treated animals are then assayed for inhibition of Mdm2 and/or Mdm4 enzymatic activity or interactions with binding partners or substrates as described, e.g., in the Examples section, as well as alleviation of symptoms or characteristics associated with the particular disease being treated. Such assays may be indirect or inferential; for example, increased surface expression of receptors (e.g., AMPARs, NMDARs, and/or D1 dopamine receptors) upon treatment with an Mdm2 and/or Mdm4 inhibitor or PSD-95 inhibitor in cultured neurons prepared from brains of animal models, improved performance in behavior tasks after treatment with Mdm2 and/or Mdm4 inhibitors or PSD-95 inhibitory inhibitors, improved electrophysiological properties in acute brain slices treated with Mdm2 and/or Mdm4 inhibitors or PSD-95 inhibitors prepared from animal models, and/or increased dendritic spine density as assessed from immunohistological staining using art-recognized techniques, when compared to treatment without the candidate or test compound or treatment with a compound that does not affect the enzymatic activity of or interaction with binding partners or substrates. Assays can also be direct, for example, a decrease in the amount of ubiquitinated substrates of Mdm2 (e.g., PSD-95, non-PSD-95 MAGUK proteins, PSD-95-associated proteins, p53) and/or Mdm4, or binding between PSD-95 and its interacting proteins, as assessed in brain homogenates prepared from the animal models, or a decrease in interaction between Mdm2 and/or Mdm4 with their respective substrates can be readily measured using the methods described supra.

A. Assays to Assess Surface Expression of Receptors

Candidate compounds and molecules and/or enantiomers and/or derivatives thereof identified as above, or known Mdm2 and/or Mdm4 inhibitors or PSD-95 inhibitors and/or enantiomers and/or derivatives thereof, may be useful for treating nervous system disorders such as neurological disorders (e.g., cognitive impairment, cognitive dysfunction, Alzheimer's disease, Parkinson's disease, and dementia), neurodevelopmental disorders (e.g., autism spectrum disorders (ASD), fragile-X syndrome, disorders affecting emotion, learning ability, memory, and Down's syndrome), or psychiatric disorders (schizophrenia, bipolar disorder, major depressive disorder, depression, anxiety disorders, attention-deficit hyperactivity disorder, and substance abuse) associated with decreased surface expression or endocytosis of AMPARs, NMDARs, and/or D1 dopamine receptors, or reduced synaptic plasticity. Accordingly, the compounds and molecules identified above are useful for decreasing AMPAR, NMDAR, and/or D1 dopamine receptor endocytosis and/or increasing surface expression of AMPAR, NMDAR, and/or D1 dopamine receptors and/or increasing synaptic plasticity.

The efficacy of these compounds for treating the aforementioned disorders can be tested using a variety of assays, including, but not limited to, those directed to assessing surface expression of the receptors in live cells or biochemically, behavior experiments, electrophysiological assays, and assays directed to assess dendritic spine morphology and density.

Surface expression of receptors in neurons can be readily assessed using art-recognized techniques, including, but not limited to, antibody feeding protocols or surface biotinylation assays (see, e.g., Ehlers, 2000; Lin et al., 2000; Bhattacharyya et al., 2009; Man et al., 2000). Antibody feeding protocols involve labeling surface receptors, e.g., AMPARs, NMDARs, or D1 dopamine receptors, with antibodies specific to respective receptor subunits (e.g., GluA1, GluA2, NR-1), followed by analysis of the density and size of receptor puncta. After treatment with a stimulus known to affect surface expression of receptors (e.g., NMDA, Aβ) in the presence or absence of an Mdm2 and/or Mdm4 inhibitor or PSD-95 inhibitor, neurons can be subsequently fixed, labeled with conjugated secondary antibodies (to label receptors still on the surface), permeabilized, and immunostained for postsynaptic markers such as PSD-95 (to analyze colocalization with the particular receptor puncta being assessed) and for presynaptic markers such as synapsin 1 or Bassoon (to identify synapses). Images can be obtained with confocal microscopy (with maximum projection reconstructions of Z-series confocal images), and the number and size of puncta quantified with commercially available software (e.g., MetaMorph (Molecular Devices)).

Alternatively, surface expression can be assessed biochemically with surface biotinylation assays (Lin et al., 2000; Man et al., 2000). Briefly, neuronal cultures can be treated with a stimulus in the presence or absence of an Mdm2 and/or Mdm4 inhibitor or PSD-95 inhibitor as described above, followed by incubation of cultures with, e.g., Sulfo-NHS-LC-Biotin (Sulfosuccinimidyl 6-[biotinamido] Hexanoate; Thermo Scientific) to label proteins expressed on the cell surface. Biotin-labeled proteins can then be isolated by incubation with neutravidin agarose beads and analyzed by quantitative western blot analysis using receptor-specific antibodies (e.g., GluA1, GluA2, NR-1 antibodies), or transferrin antibody as control. These assays can be supplemented with those that assess the amount of internalized receptor subunits will be assessed after a treatment (e.g., NMDA, Aβ). Briefly, receptors on the cell-surface of cultured neurons can be labeled with Sulfo-NHS-LC-Biotin prior to treatments, the remaining surface biotin cleaved with glutathione, and cultures lysed in an appropriate lysis buffer. Biotinylated proteins can then be isolated by neutravidin agarose beads and analyzed by quantitative immunoblot.

B. Behavior Tests, Electrophysiology, and Assessment of Dendritic Spines

Tests to assess behavior, including those relating to anxiety, hyperactivity, hypoactivity, appetite, eating habits, attention, drug abuse, drug addiction, learning and memory, mood, depression, schizophrenia, pain, sleep, arousal, sexuality, and social dominance, are well-known in the art, and are disclosed in, e.g., US2008/0260744, US2011/0212888, US2011/0160181, (all of which are hereby incorporated by reference in their entirety).

Any number of behavioral tests can be used to test performance during behavioral testing. The particular type of performance test may depend upon at least one of several factors including the behavioral repertoire of the animal (e.g., an animal model of a nervous system disorder) and the purpose of the testing. Non-limiting examples of tests for assessing the reflex function of mice include assessments of approach response, touch response, eyelid reflex, pinna reflex, sound response, tail pinch response, pupillary reflex, and righting reflex. Non-limiting examples of behavioral tests suitable for assessing the motor function of mice include open field locomotor activity assessment, the rotarod test, the grip strength test, the cylinder test, the limb-placement or grid walk test, the vertical pole test, the inverted grid test, the adhesive removal test, the painted paw or catwalk (gait) tests, the beam traversal test, and the inclined plane test. Non-limiting examples of behavioral tests suitable for assessing the long-term memory function of mice include the elevated plus maze test, the Morris water maze swim test, contextual fear conditioning, the Y-maze test, the T-maze test, the novel object recognition test, the active avoidance test, the passive (inhibitory) avoidance test, the radial arm maze test, the two-choice swim test, the hole board test, the olfactory discrimination (go-no-go) test, and the pre-pulse inhibition test. Non-limiting examples of behavioral tests suitable for assessing the anxiety of mice include the open field locomotion assessment, observations of marble-burying behavior, the elevated plus maze test, and the light/dark box test. Non-limiting examples of behavioral tests suitable for assessing the depression of mice includes the forced swim test, the hot plate test, the tail suspension test, anhedonia observations, and the novelty suppressed feeding test.

Methods relating to the assessment of glutamatergic synapses and synaptic plasticity are well-known in the art and described, e.g., in Bhattacharyya et al., 2009; Futai et al., 2007; Nakagawa et al., 2004; and Schlüter et al., 2006.

Methods to assess the morphology and quantity of dendritic spines are well known in the art (see, e.g., Honig et al., 1986; Kim et al., 2007), and can be readily assessed using commercially available kits (e.g., FD NeuroTechnologies, Ellicott City, Md.).

IV. Animal Models of Nervous System Disorders

Animal models that track the progression of nervous system diseases can be used to test the efficacy of Mdm2 and/or Mdm4 inhibitors or PSD-95 inhibitors and/or enantiomers and/or derivatives thereof using the assays described supra. One aspect of the invention relates to treating neurological disorders (e.g., cognitive impairment, cognitive dysfunction, Alzheimer's disease, Parkinson's disease, and dementia), neurodevelopmental disorders (e.g., autism spectrum disorders (ASD), fragile-X syndrome, disorders affecting emotion, learning ability, memory, and Down's syndrome), or psychiatric disorders (schizophrenia, bipolar disorder, major depressive disorder, depression, anxiety disorders, attention-deficit hyperactivity disorder, and substance abuse) with Mdm2 and/or Mdm4 inhibitors or PSD-95 inhibitors. Accordingly, animal models that track the symptoms and features of these disorders are useful for testing the efficacy of Mdm2 and/or Mdm4 inhibitors (known or candidate Mdm2 and/or Mdm4 inhibitors) or PSD-95 inhibitors in treating the respective disorders.

For example, transgenic mouse models of Alzheimer's disease have been described in the literature. In one non-limiting example, triple transgenic mouse model (3×Tg-AD), which expresses both mutant APP (SWE: K670N, M671L) and Tau (P301L) on a mutant presenilin (PS)1 (M146V) background, closely mimics AD progression in humans (Oddo et al., 2003). In these mice intracellular Aβ is present in 3-4 month old mice in the neocortex and in 6-month old mice in the CA1 region of the hippocampus (Id.). Extracellular Aβ deposits are present in 6-month old mice and are readily evident by 12 months in neocortex and hippocampus (Id.). Basal synaptic transmission is impaired and synaptic plasticity is strongly compromised by 6-months of age (Id.). Transgenic animal models are also known in the art for other diseases, including, but not limited to, Parkinson's disease (Dehay et al., 2011), schizophrenia (Young et al., 2010), neuropsychiatric disorders (Nestler and Hyman, 2010), Fragile X (Casten et al., 2011; Hunsaker et al., 2012), Alzheimer's disease (Chin, 2011; Obulesu et al., 2010), and autism (Moy, 2008).

V. Therapeutic Applications

As described herein, Mdm2 and/or Mdm4 inhibitors or PSD-95 inhibitors and/or enantiomers and/or derivatives thereof have therapeutic utility via, e.g., inhibiting the ubiquitination of PSD-95 or non-PSD-95 MAGUK proteins (e.g., SAP97, SAP102, PSD-93) and/or the interaction between Mdm2 and/or Mdm4 and PSD-95, non-PSD-95 MAGUK proteins, and/or PSD-95 associated proteins. Accordingly, the present invention provides for both prophylactic and therapeutic methods of treating a subject at risk of (or susceptible to) a disorder caused by a neurological disorder (e.g., cognitive impairment, cognitive dysfunction, Alzheimer's disease, Parkinson's disease, and dementia), neurodevelopmental disorder (e.g., autism spectrum disorders (ASD), fragile-X syndrome, disorders affecting emotion, learning ability, memory, and Down's syndrome), or psychiatric disorder (schizophrenia, bipolar disorder, major depressive disorder, depression, anxiety disorders, attention-deficit hyperactivity disorder, and substance abuse) associated with aberrant endocytosis of AMPAR, NMDAR and/or D1 dopamine receptors and/or aberrant surface expression of AMPARs, NMDARs, and/or D1 dopamine receptors (e.g., Alzheimer's disease) comprising administering to a subject in need thereof, or contacting a neuron with, a Mdm2 and/or Mdm4 inhibitor, or PSD-95 inhibitor. The present invention also provides for a method of modulating synaptic plasticity comprising administering to a subject in need thereof a Mdm2 and/or Mdm4 inhibitor, or PSD-95 inhibitor. In one embodiment, the invention provides an Mdm2 and/or Mdm4 inhibitor for decreasing the enzymatic activity of Mdm2 and/or Mdm4, or decreasing the level of binding to a protein (e.g., PSD-95, non-PSD-95 MAGUK protein such as SAP97, SAP102, PSD-93, PSD-95-associated proteins) that associates with Mdm2 and/or Mdm4. In another embodiment, the invention provides an PSD-95 inhibitor to disrupt binding between PSD-95 and its interacting proteins. In another embodiment of the invention, treatment with an Mdm2 and/or Mdm4 inhibitor, or PSD-95 inhibitor, results in decreased ubiquitination of PSD-95, non-PSD-95 MAGUK proteins, or PSD-95 associated proteins, allowing for decreased endocytosis of and increased surface expression of AMPAR, NMDAR, and/or D1 dopamine receptors. It is understood that "treatment" or "treating" as used herein, is defined as the administration of a therapeutic agent to a subject, or application of a therapeutic agent to an isolated tissue or cell line from a subject, who has a disease or disorder, with the purpose to cure, heal, alleviate, relieve, later, remedy, ameliorate, improve or affect the disease or disorder, the symptoms of the disease or disorder, or the predisposition toward the disease.

In another aspect, the invention provides a method for preventing in a subject, a disease or condition associated with aberrant surface expression of AMPARs, NMDARs, and/or D1 dopamine receptors. Subjects at risk for a disease which is caused or contributed to by aberrant surface expression of these receptors can be identified by, for example, any or a combination of diagnostic or prognostic assays as described herein. Administration of a prophylactic agent can occur prior to the manifestation of symptoms characteristic of the decreased surface expression of AMPAR, NMDAR, and/or D1 dopamine receptors, such that a disease or disorder is prevented or, alternatively, delayed in its progression. In addition to known Mdm2 and/or Mdm4 inhibitors (e.g., Nutlin-3a) or PSD-95 inhibitors, additional Mdm2 and/or Mdm4 inhibitors or PSD-95 inhibitors can be identified based on screening assays described herein.

In the therapeutic applications described herein, the Mdm2 and/or Mdm4 inhibitors, or PSD-95 inhibitors, can be formulated to cross the blood-brain barrier as necessary.

In exemplary embodiments, the invention features selecting a subject that will particularly benefit from the treatment methodologies of the instant invention. Such subjects can be selected on the basis of certain phenotypic, genotypic, symptomatic and/or behavioral criteria. In exemplary embodiments, a subject particularly benefiting from the treatment methodologies of the instant invention is one having aberrant Mdm2 and/or Mdm4 activity, optionally in combination with aberrant surface expression of AMPARs, NMDARs, and/or D1 dopamine receptors. Subjects who may benefit from the methods of the present invention include, but are not limited, those who have been diagnosed with or are at risk of developing a neurological disorder, neurodevelopmental disorder, or psychiatric disorder, based on art-recognized behavior criteria. Diagnostic criteria for various disorders of the nervous system are provided by the Diagnostic and Statistical Manual of Mental Disorders (DSM-IV). Although by no means limiting, those at risk of developing nervous system disorders can be identified by, e.g., the presence of genetic mutations that predispose the subject to a genetic disorder. In a non-limiting example, the risk of developing Alzheimer's disease is reflected in the presence of a genetic mutation in the amyloid precursor protein (APP) gene that increases or alters processing of APP to Aβ, particularly processing of APP to increased amounts of the long form of Aβ (i.e., Aβ1-42 and Aβ1-43). Other predisposing factors for Alzheimer's disease, such as mutations in the presenilin genes, PS1 and PS2, are thought to indirectly affect APP processing and generate increased amounts of the long form of Aβ. Other genetic markers of risk and method for identifying those with Alzheimer's Disease are detailed in, e.g., US2008/0279846, which is hereby incorporated by reference in its entirety. Predisposing factors are also known in the art for other nervous system disorders (autism spectrum disorders: SHANK3 (Prosap2), contactin-associated protein-like 2 (CNTNP2), mTOR, TSC2, FOX1 (A2BP1), neuroligin 4, semaphorin 5A, patched domain containing (PTCH D)1, fragile X mental retardation protein (FMRP), methyl CpG binding protein (MeCP2), phosphatase and tensin homolog (PTEN); Alzheimer's disease: apolipoprotein E (ApoE), presenilin, (calcium homeostasis modulator) CALHM1, BchE-K, TOMM40; schizophrenia: disrupted-in-schizophrenia (DISC)1, dopamine- and cyclic AMP-regulated phosphoprotein (DARPP-32), dysbindin, glutathione, catechol-O-methyltransferase (COMT), KIAA0513, oligodendrocyte lineage transcription factor $(OLIG)_2$, zinc finger protein (ZNF)804A, regulator of G-protein signaling (RGS4), sterol regulatory element-binding transcription factor (SREBF)1/2, trace amine associated receptor $(TAAR)_6$, vasoactive intestinal peptide receptor (VIPR2), reelin, ErbB4, neuregulin; anxiety: COMT, corticotropin-releasing factor (CRF)-2, delta-aminolevulinate dehydratase (ALAD), dynein light chain (DYNLL)2, prosaposin, transmembrane protein (TMEM)132d; Fragile X: fragile X mental retardation (FMR)1). Determination of the presence of genetic polymorphisms and/or mutations can be readily carried out using routine methods in the art (e.g., DNA sequencing). Thus, subjects at risk for developing nervous system disorders can be readily identified and treated with the methods of the present invention.

VI. Pharmaceutical Compositions

Mdm2 and Mdm4 inhibitors or PSD-95 inhibitors and/or enantiomers and/or derivatives thereof, and agents capable of modulating the course of the target disease (e.g., a neurological disorder, neurodevelopmental disorder, or psychiatric disorder), can be used therapeutically or prophylactically either alone or in combination. Accordingly, the present invention provides compositions comprising a Mdm2 and/or Mdm4 inhibitor or PSD-95 inhibitor and/or agents capable of modulating the course of the target disease, and a pharmaceutically acceptable carrier. The invention further provides methods of treating or attenuating a neurological disorder, neurodevelopmental disorder, or psychiatric disorder in a subject in need thereof by administering compositions that include a Mdm2 and/or Mdm4 inhibitor or PSD-95 inhibitor and/or agents capable of modulating the course of the target disease, or a composition comprising the same.

The invention features the use of compounds that inhibit the enzymatic activity and/or substrate binding activity of Mdm2 and/or Mdm4. Non-limiting examples of compounds that inhibit enzymatic activity include, but are not limited to, arylsulfonamides and/or enantiomers and/or derivatives thereof, bisarylureas and/or enantiomers and/or derivatives thereof, acylimidazolones and/or enantiomers and/or derivatives thereof, deazaflavins and/or enantiomers and/or derivatives thereof (e.g., HLI98 and HLI373), natural products and/or enantiomers and/or derivatives thereof (e.g., sempervirine and resveratrol), acridines and/or enantiomers and/or derivatives thereof, and JnJ-26854165 (serdematain; as disclosed in Tabernero et al., *Clin Cancer Res.* 2011 Oct. 1; 17(19):6313-21). Non-limiting examples of compounds that inhibit substrate binding activity include benzodiazepinediones (e.g., TDP521252 and TDP665759), isoindoline compounds and derivatives thereof (e.g., those disclosed in US 2011/0224274, hereby incorporated by reference in its entirety), cis-imidazoline derivatives (e.g., Nutlin-1, Nutlin-2, Nutlin-3, Nutlin-3a), benzoylthiourea derivatives (e.g., tenovin-1 as described in EP2099445, herein incorporated by reference in its entirety), spiro-oxindoles (e.g., MI-43, MI-63, MI-219, and MI-319), and thiophene derivatives (e.g., RITA (NSC652287)). The effects of members of each family of compounds toward Mdm2 and/or Mdm4 can be readily tested using the assays described supra. Amino acid compositions are also within the scope of the invention.

The invention pertains to uses of the above-described agents for therapeutic treatments as described infra. Accordingly, the agents of the present invention can be incorporated into pharmaceutical compositions suitable for administration. As used herein, the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral (e.g., intravenous), intradermal, subcutaneous, intraperitoneal, intramuscular, nasal, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity, such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N J) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, liquid polyethylene glycol, and the like), and suitable mixtures thereof. The proper fluidity can be maintained, e.g., by the use of a coating such as lecithin, by the maintenance of the required particle size in the case of dispersion, and by the use of surfactants. Prevention of the action of microorganisms can be achieved by various antibacterial and antifungal agents, e.g., parabens, chlorobutanol, phenol, ascorbic acid, thimerosal, and the like. In many cases, it will be preferable to include isotonic agents, e.g., sugars, polyalcohols such as mannitol, sorbitol, and sodium chloride in the composition. Prolonged absorption of the injectable compositions can be brought about by including in the composition an agent which delays absorption, e.g., aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches, and the like can contain any of the following ingredients, or compounds of a similar nature: e.g., a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal and transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodymanic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

In some embodiments, the agents (and other optional pharmacological agents) of the invention can be delivered directly via a pump device. For example, in some embodiments, the Mdm2 and/or Mdm4 inhibitor, and compositions thereof, of the invention are delivered directly by infusion into the diseased tissue, e.g., tissue from a subject with a neurological disorder, neurodevelopmental disorder, or psychiatric disorder. The preferred method of administering the compositions of the invention is by direct delivery of the compounds to the central nervous system, preferentially to the brain, especially near to or directly at the site of the disorder, e.g., the hippocampus in the case of Alzheimer's disease or the substantia nigra in the case of Parkinson's disease. Accordingly, administration may be into a ventricle, intrathecal, or intracerebral ventricular. For example, an Omaya reservoir-shunt with in-line filter can be surgically placed into the cisternal space. A therapeutic compound in an appropriate excipient (e.g., phosphate-buffered saline) is instilled into the shunt by injection on a prescribed basis.

The compounds can be administered, e.g., by intranasal delivery, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions can also be used as pharmaceutically acceptable carriers. These can be prepared according to methods known to those skilled in the art, e.g., as described in U.S. Pat. No. 4,522,811.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to non-affected tissue, and thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the compound which achieves a half-maximal inhibition of symptoms) as determined in cell culture. Such information can be used to more accurately determine useful doses in humans. Levels in plasma may be measured, e.g., by high performance liquid chromatography.

A therapeutically effective amount of a composition containing a compound of the invention (e.g., a Mdm2 and/or Mdm4 inhibitor, e.g., nutlin-3) (i.e., an effective dosage) is an amount that decreases Mdm2 and/or Mdm4 ubiquitin ligase activity, or interaction with substrates, by at least 10%. Higher percentages, e.g., 20, 30, 40, 50, 60, 70, 80, 90, 100% may be preferred in certain embodiments. The composition can be administered one or more times per week (e.g., up to 15 times, or up to 12 times, or up to 10 times, or up to 8 times, or up to 6 times, or up to 4 times, or up to 2 times per week) for between 1 to 10 weeks. The skilled artisan will appreciate that certain factors may influence the dosage and timing required to effectively treat a subject, including, but not limited to, the severity of the disease or disorder, previous treatments, the general health and/or age of the subject, and other diseases present. Moreover, treatment of a subject with a therapeutically effective amount of a composition can include a single treatment or a series of treatments. The skilled artisan will appreciate that the Mdm2 and/or Mdm4 inhibitors, and PSD-95 inhibitors, will be used at dosages below toxic levels associated with routine therapeutic treatment, optionally formulated to pass the blood-brain barrier as necessary.

It is furthermore understood that appropriate doses of a composition depend upon the potency of the composition with respect to the activity to be modulated (e.g., inhibition of Mdm2 and/or Mdm4 activity and/or inhibition of Mdm2 and/or Mdm4 interaction with substrates; or inhibition of PSD-95 binding with interacting proteins; or inhibition of post-translational modifications of endogenous PSD-95). When one or more of these molecules (e.g., up to 2, or up to 3, or up to 5, or up to 10 molecules) is to be administered to an animal (e.g., a human) to inhibit the activity of or affinity for substrates of Mdm2 and/or Mdm4, a physician, veterinarian, or researcher may, for example, prescribe a relatively low dose at first, subsequently increasing the dose until an appropriate response is obtained. In addition, it is understood that the specific dose level for any particular subject will depend on a variety of factors including the activity of the specific compound employed, the age, body weight, general health, gender, and diet of the subject, the time of administration, the route of administration, the rate of excretion, any drug combination, and the degree of activity or affinity to substrates being inhibited.

The pharmaceutical compositions described herein can be formulated to cross the blood-brain barrier as necessary.

V. Combinatorial Treatment

Compositions comprising a Mdm2 and/or Mdm4 inhibitor and/or PSD-95 inhibitor, and/or enantiomers and/or derivatives thereof, and pharmaceutical compositions comprising the same, can be used in the methods for the invention in combination with additional therapeutic agents [e.g., memantine (1-amino-3,5-dimethyl-adamantane)]. Such additional agents preferably contribute to alleviation of symptoms associated with a neurological disorder, neurodevelopmental disorder, or psychiatric disorder. Such additional agents may be administered to a subject prior to, simultaneously with, or subsequent to the administration of a Mdm2 and/or Mdm4 inhibitor or PSD-95 inhibitor. In the context of AD, for example, Mdm2 and/or Mdm4 inhibitors or PSD-95 inhibitors can be administered with acetylcholinesterase inhibitors (for mild to severe AD symptoms) and/or memantine (Namenda) (for moderate to severe cases).

VI. Kits Comprising Mdm2 and/or Mdm4 Inhibitors

The invention additionally provides kits comprising a composition comprising Mdm2 and/or Mdm4 inhibitors (e.g., Nutlin-3a and HLI-373) or PSD-95 inhibitors, and/or enantiomers and/or derivatives thereof and instructions for administration of the composition to a subject for treating a neurological disorder, neurodevelopmental disorder, or psychiatric disorder.

The kits of the invention may additionally contain an additional therapeutic agent that is known to be beneficial for treating a neurological disorder, neurodevelopmental disorder, or psychiatric disorder. In a preferred embodiment, the additional therapeutic agent is memantine (1-amino-3, 5-dimethyl-adamantane). Other additional therapeutic agents that can be included are well known in the art, and can be found at, e.g., the National Institute of Mental Health website (at www.nimh.nih.gov/index.shtml).

All publications, patents, and patent applications cited herein, whether supra or infra, are hereby incorporated by reference in their entirety.

The above disclosure generally describes the present disclosure, which is further exemplified by the following examples. These specific examples are described solely for purposes of illustration, and are not intended to limit the scope of this disclosure. Although specific targets, terms, and values have been employed herein, such targets, terms, and values will likewise be understood as exemplary and non-limiting to the scope of this disclosure.

EXAMPLES

While many studies have contributed to an understanding of the role of polyubiquitination and proteasome degradation in synapse remodeling, the function of monoubiquitination at the synapse is not known. While previous studies have implicated the ubiquitination and proteasome-dependent degradation of PSD-95 in NMDAR-induced AMPAR endocytosis (Colledge et al., 2003), other studies have implicated ubiquitination, but not proteasome function, in NMDAR-induced AMPAR endocytosis and LTD (Citri et al., 2009). Therefore, the underlying mechanisms by which ubiquitination of PSD-95 regulates NMDAR-induced internalization of AMPARs are unclear. The data presented in the following examples support a novel non-proteasomal signaling function for ubiquitinated PSD-95 in the regulation of NMDAR-induced AMPAR endocytosis. These data provide evidence that PSD-95 is monoubiquitinated on multiple sites and that this posttranslational modification functions in non-proteasomal signaling by promoting the interaction of β-adaptin with PSD-95. AMPAR endocytosis occurs at clathrin endocytic zones adjacent to the postsynaptic density (Blanpied et al., 2002; Racz et al., 2004), and the results suggest that monoubiquitination of PSD-95 promotes the recruitment of the AMPAR/PSD-95 complex to clathrin endocytic zones. Therefore, these studies suggest a model where NMDAR stimulation and/or Cdk5 inhibition promote monoubiquitination of PSD-95 by Mdm2 and the subsequent interaction of monoubiquitinated PSD-95 and associated AMPAR with the AP-2/clathrin endocytic complex, thus facilitating AMPAR endocytosis (FIG. 5C).

Previous studies have shown that PSD-95 is ubiquitinated by the E3 ligase Mdm2 (Colledge et al., 2003). The below data now demonstrate that Cdk5 activity inhibits PSD-95 ubiquitination and the colocalization and interaction of Mdm2 with PSD-95, suggesting that Cdk5 regulates the ubiquitination of PSD-95 by regulating the intracellular distribution of Mdm2. Mdm2 activity is regulated by numerous signaling pathways (Wade et al., 2010) as well as changes in the stability and intracellular distribution of Mdm2, which are affected by the interaction of Mdm2 with the tumor suppressor ARF and the oncoprotein Mdmx (Mdm4) (Mukhopadhyay and Riezman, 2007). Therefore these studies indicate that in neurons Cdk5 is a component of the complex signaling network regulating Mdm2 intracellular distribution and/or activity. Mdm2 can catalyze both monoubiquitination as well as polyubiquitination of the tumor suppressor p53 (Li et al., 2003). Although the discrete bands of ubiquitinated PSD-95 observed previously (Colledge et al., 2003) are consistent with monoubiquitination on multiple sites, PSD-95 ubiquitination was not characterized as polyubiquitination or monoubiquitination (Colledge et al., 2003). The following study provides the first evidence that PSD-95 is monoubiquitinated on multiple sites in vivo, given the differential immunoreactivity to the FK1 and FK2 antibodies. Consistent with monoubiquitination of PSD-95, no change in PSD-95 protein levels in p35 was observed in knockout brain in vivo as well as in roscovitine-treated neurons, while PSD-95 ubiquitination is increased more than two-fold. Previous studies have associated PSD-95 ubiquitination to its proteasomal degradation by showing that deletion of the PEST motif in PSD-95 or treatment with the proteasome inhibitor MG132 protect PSD-95 from degradation (Colledge et al., 2003). Interestingly, MG132 is also an inhibitor of the proteases calpain and cathepsins (Lee and Goldberg, 1998; Elliott et al., 2003) and PEST motifs have been implicated in proteolysis of proteins by the calcium-dependent intracellular proteases calpains (Rechsteiner and Rogers, 1996; Shumway et al., 1999). Calpains are activated by NMDARs (Vanderklish et al., 1995) and can mediate the degradation of PSD-95 (Lu et al., 2000; Vinade et al., 2001; Gascón et al., 2008). Thus, while calpains may play a role in PSD-95 degradation following deletion of the PEST sequence or MG132 treatment, our data demonstrate that PSD-95 monoubiquitination does not result in PSD-95 degradation and suggest an alternative function for PSD-95 ubiquitination.

A well-characterized non-proteolytic signaling function of ubiquitin is in the endocytic pathway, where ubiquitin serves as a signal for the entry of endocytic cargo into vesicles both at the plasma membrane and at the late endosome (Hicke and Dunn, 2003). A function for PSD-95 in endocytosis is suggested both by previous studies indicating that one motif within the C-terminus of PSD-95 is associated with clathrin-mediated endocytosis of a transmembrane receptor (Craven and Bredt, 2000) and by the association of PSD-95 with AP-2 detected in mass spectrometry studies (Fernandez, et al., 2009). The studies described below indicate that mono ubiquitination of PSD-95 induced by Cdk5 inhibition correlates in vivo with increased interaction of PSD-95 with β-adaptin, a component of clathrin adaptor protein complexes, while mice with a genetic deletion of Mdm2 have reduced interaction of β-adaptin with PSD-95. Therefore these results indicate a strong correlation between PSD-95 ubiquitination and interaction with β-adaptin and support a role for PSD-95 in receptor endocytosis.

NMDAR activity induces both rapid and transient PSD-95 ubiquitination and AMPAR endocytosis (Colledge et al., 2003). These studies indicate that NMDAR activity induces a time-dependent interaction of PSD-95 with β-adaptin and that this increase parallels the time-dependent increase in PSD-95 ubiquitination, supporting an NMDAR-dependent increase in PSD-95 ubiquitination and interaction with β-adaptin. Furthermore, it is demonstrated that, while in p53 knockout control mice NMDAR activity induces an increase in PSD-95 interaction with β-adaptin, this increase is greatly reduced in Mdm2/p53 double knockout mice. Together these results are consistent with a role for PSD-95 ubiquitination in regulating the interaction of PSD-95 with β-adaptin and support a role for ubiquitinated PSD-95 in the recruitment of β-adaptin/AP-2/clathrin complex to promote AMPAR endocytosis.

Materials and Methods
Western Blots of Brain Lysates.

Brains of adult p35 knockout mice and control littermates were gifts of Dr. Li-Huei Tsai (MIT). Brain lysates were prepared according to Zhang et al., (2008). Briefly, brains (without cerebellum) were first homogenized and lysed in 1% deoxycholate (DOC) lysis buffer (150 mM NaCl, 1% DOC, 50 mM Tris, pH 8.8), to which an equal volume of modified radioimmunoprecipitation assay (RIPA) buffer was added (150 mM NaCl, 1 mM ethylenediaminetetraacetic acid (EDTA), 1% Triton X-100, 0.1% SDS, 50 mM Tris/HCl pH 7.4) (Kalia et al., 2006). All buffers were supplemented with protease and phosphatase inhibitor cocktails (Roche). Immunoprecipitations and western blot analysis were carried out as previously described (Zhang et al., 2008). Protein concentrations of the lysates were determined by Detergent Compatible Protein Assay (Bio-Rad) and lysates (inputs) were analyzed by western blot to determine whether similar amounts of proteins were used in the experiments. Antibodies used were: mouse monoclonal β-adaptin antibody (BD Transduction); mouse monoclonal Mdm2 antibody (Millipore); mouse monoclonal PSD-95 antibody (Antibodies Incorporated); mouse monoclonal ubiquitin antibody (BD Transduction); mouse monoclonal FK1 antibody (Biomol/Enzo Life Sciences); and mouse monoclonal FK2 antibody (Biomol/Enzo Life Sciences). Western blots were visualized by enhanced chemiluminescence (ECL, Amersham) and immunoreactive bands were digitally scanned and quantified with ImageJ software (NIH). Values were expressed as mean±S.E.M. and statistically compared using Student's t-test.

Acute Forebrain Slices.

Acute forebrain slices were prepared as previously described (Patel et al., 2003; Zhang et al., 2008). Briefly, brains of adult wild-type, p53 knockout or Mdm2/p53 double knockout mice were isolated, and 300 μm coronal slices of forebrain (within the region corresponding approximately to Bregma −1.0 to −3.5 mm, containing the hippocampus) were prepared using a Vibratome (Leica Microsystems VT1000S) in ice-cold oxygenated artificial cerebrospinal fluid (ACSF: 117 mM NaCl, 1.7 mM KCl, 1.2 mM MgCl2, 2.5 mM $CaCl_2$, 1.2 mM NaH2PO4, 25 mM NaHCO3, 11.5 mM glucose). Slices were preincubated in ACSF for 1 h before treatments and all experiments were conducted at 32° C. in 95% O2 and 5% CO2 incubator. NMDA treatment was conducted by incubating slices with 100 μM NMDA for 3 min in ACSFcLTD (124 mM NaCl, 5 mM KCl, 1.5 mM MgCl2, 2.5 mM CaCl2, 1.25 mM NaH2PO4, 26 mM NaHCO3, 10 mM glucose) (Lee et al., 1998). After agonist washout, the slices were further incubated in ACSF-cLTD for the time indicated (5-10 min). Slice lysates were prepared as previously described (Zhang et al., 2008) and PSD-95 immunoprecipitated from the lysates was analyzed by Western blot and quantified as described above. Values were expressed as mean±S.E.M. and statistically compared using analysis of variance (ANOVA).

Cell Culture and Transfections.

CAD cells were maintained in Dulbecco's Modified Eagle Medium (DMEM) supplemented with 10% fetal bovine serum and transfected using Lipofectamine 2000 (Invitrogen) according to the manufacturer's instructions. cDNAs used in transfections were: PSD-95 in pcDNA3 (Morabito et al., 2004), pRK5-HA-Ubiquitin-K0 (Addgene), p35, Cdk5, DNCdk5 in pcDNA3 (Li-Huei Tsai, MIT, Morabito et al., 2004). Cells were collected and lysed 18-20 hr after transfection, at which time there is no apparent degradation of proteins or cell death. Analysis of the immunoprecipitated PSD-95 was performed as described above and values were expressed as mean±S.E.M.

Dissociated Hippocampal Cultures and Immunocytochemistry.

Dissociated hippocampal cultures were prepared from E17-E18 rat brains as described previously (Zhang et al., 2008). Hippocampal neurons were plated on coverslips coated with poly-D-lysine and laminin at a density of 6600/cm2 and grown in Neurobasal medium supplemented with B27 and GlutaMax (Invitrogen) for 17-21 days in vitro (DIV). Cultures were treated for 45 min with 10 μM roscovitine or DMSO as control, fixed in 4% paraformaldehyde, 5% sucrose in PBS for 15 minutes, then permeabilized in blocking buffer (10% bovine serum albumin (BSA), 0.2% Triton-X100 in PBS) for 1 hr. Cultures were then stained using rabbit polyclonal PSD-95 antibody (Zymed) together with either mouse monoclonal μ-adaptin antibody (BD Transduction) or mouse monoclonal Mdm2 antibody (Millipore) and secondary antibodies (Alexa488- and Alexa594-conjugated, Molecular Probes), and mounted in Vectashield (Vector Laboratories). Omission of primary antibody was used as a control for specificity of staining. Each experimental treatment and analysis was performed blind using raw images from three experiments and six coverslips. Images were captured using a Leica TCS laser-scanning confocal microscope under identical conditions (63× objective, 1024×1024 pixel format, and identical settings). Images from each experiment were thresholded using identical values and analyzed by MetaMorph software. The colocalization was expressed as mean±S.E.M. and statistically compared using Student's t-test.

Mice.

Mdm2/p53 double knockout mice, p53 knockout mice, and p35 knockout mice have been described previously (Chae et al., 1997; Jones et al., 1995; Donehower et al., 1992). All mice were bred and analyzed in accordance with institutional guidelines and as approved by Institutional Animal Care and Use Committee.

Example 1

Figure 1:
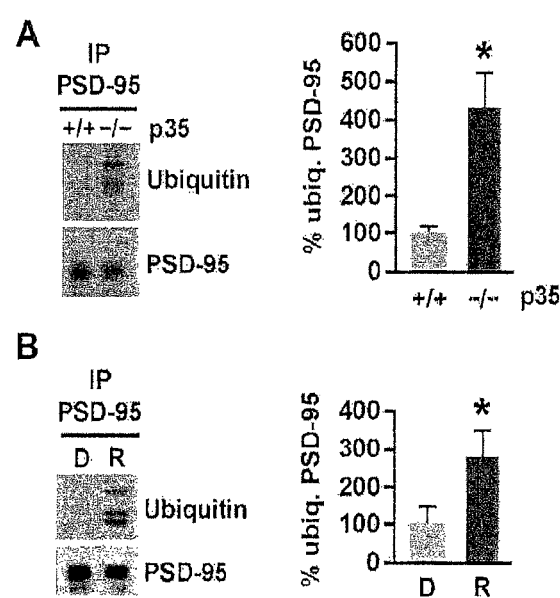
FIG. 1. Reduced Cdk5 activity increases PSD-95 ubiquitination

Reduced Cdk5 Activity Increases the Interaction of PSD-95 with Mdm2 and PSD-95 Ubiquitination To assess whether PSD-95 ubiquitination is regulated by Cdk5, the levels of PSD-95 ubiquitination were analyzed in p35 knockout mice, in which the activity of Cdk5 is reduced by 78% (Hallows et al., 2006). Immunoblotting of PSD-95 immunoprecipitated from brain using an ubiquitin antibody revealed discrete bands resembling the ubiquitinated species observed by Colledge et al. (2003) and a more than 4-fold increase in PSD-95 ubiquitination in p35 knockout mice compared to wild-type littermates (431.3%±84.4% versus wild-type 100%±18.5%, n=3, p<0.05; FIG. 1A). The levels of PSD-95 ubiquitination were also determined in acute mouse forebrain slices in which Cdk5 was inhibited pharmacologically by treatment with the Cdk5 inhibitor roscovitine (10 μM, 45 min) (FIG. 1B). Consistent with the increase in PSD-95 ubiquitination observed in p35 knockout, pharmacological inhibition of Cdk5 by roscovitine resulted in a more than 2-fold increase in PSD-95 ubiquitination (274.6%±71.6% versus 100%±54.5% in untreated control slices, n=4, p<0.01). These data indicate that decreased Cdk5 activity results in increased PSD-95 ubiquitination.

Mdm2 has been identified as the ubiquitin ligase for PSD-95 in ubiquitination assays and in transfected Mdm2 knockout mouse embryonic fibroblasts (Colledge et al., 2003). Since the ubiquitination of PSD-95 is dependent on Mdm2, the increase in PSD-95 ubiquitination that we observed under reduced Cdk5 activity could reflect an increased interaction of Mdm2 with PSD-95. To investigate whether Cdk5 regulates the interaction between Mdm2 and PSD-95, PSD-95 immunoprecipitated from brain lysates was analyzed in p35 knockout mice and wild-type littermates by immunoblotting with an Mdm2 antibody (FIG. 2A). Consistent with the increase in ubiquitinated PSD-95 in p35 knockout, the interaction of Mdm2 with PSD-95 was increased more than 3-fold in p35 knockout mice compared to wild-type (360.5%±65.6% versus wild-type 100%±20.6%, n=3; p<0.05). These results indicate that reduced Cdk5 activity increases the interaction of Mdm2 with PSD-95. The degree of colocalization of Mdm2 with PSD-95 was also assessed in cultured hippocampal neurons, and the impact of Cdk5 activity on the colocalization, by immunocytochemical analysis of roscovitine-treated cultures (FIG. 2B). It was found that roscovitine treatment promoted the colocalization of Mdm2 with PSD-95 puncta compared to DMSO control sister cultures (149%±27.4% versus control 100%±24.8%, n=4; p<0.05), indicating that reduced Cdk5 activity increases the colocalization of Mdm2 with PSD-95. Together these data show that decreased Cdk5 activity induces the recruitment of Mdm2 to PSD-95 puncta and the interaction of Mdm2 with PSD-95, thus promoting PSD-95 ubiquitination by Mdm2.

Example 2

PSD-95 is Monoubiquitinated on Multiple Lysines without Affecting its Protein Levels Ubiquitination may occur by the addition of a single ubiquitin moiety to one or multiple lysine residues (monoubiquitination and multiubiquitination, respectively) or by addition of polymeric ubiquitin chains formed through lysines within ubiquitin (polyubiquitination) (DiAntonio and Hicke, 2004; d'Azzo et al., 2005). While Mdm2 can catalyze both monoubiquitination as well as polyubiquitination (Li et al., 2003), the discrete ubiquitinated species observed by Bianchetta et al. (2011) and Colledge et al. (2003) suggest the addition of single ubiquitin moieties to PSD-95. To determine whether the ubiquitination of PSD-95 reflects multiubiquitination or polyubiquitination, the FK1 and FK2 antibodies were used, both of which recognize polyubiquitinated proteins, while only the FK2 antibody detects monoubiquitin conjugates (Fujimuro et al., 1994). Immunoblotting of PSD-95 immunoprecipitated from p35 knockout brain revealed that ubiquitination of PSD-95 was detected by the FK2 but not the FK1 antibody (FIG. 3A), and similar results were obtained with roscovitine-treated acute forebrain slices (FIG. 3B). The presence of polyubiquitinated species in the input lanes serves as control for FK1 immunoreactivity. Together these data indicate that the increased ubiquitination of PSD-95 (observed when Cdk5 activity is reduced) corresponds to monoubiquitination of PSD-95 on multiple lysines.

Nano-Liquid Chromatography-Tandem Mass Spectrometry (nLC-MS/MS) analysis with the hybrid LTQ-Orbitrap mass spectrometer using PSD-95 immunoprecipitated from acute mouse forebrain slices treated with the Cdk5 inhibitor roscovitine resulted in the identification of K10, 403, 544, 588, and 591 as preferentially ubiquitinated under Cdk5 inhibition conditions. Similar analysis under naïve control conditions (DMSO), resulted in obtaining >90% coverage.

While polyubiquitination has been associated with the targeting of polyubiquitinated proteins for degradation by the 26S proteasome, monoubiquitination and multiubiquitination have been implicated in protein-protein recognition, protein sorting and intracellular localization (DiAntonio and Hicke, 2004; d'Azzo et al., 2005). While PSD-95 ubiquitination has not been characterized as polyubiquitination or monoubiquitination, it has been associated with proteasomal degradation (Colledge et al., 2003). Since these data indicate PSD-95 monoubiquitination, the levels of PSD-95 were analyzed in brain lysates derived from p35 knockout and wild-type littermates (FIG. 3C) to assess the relationship between PSD-95 monoubiquitination and protein levels. No significant change in PSD-95 protein levels was observed (normalized to actin) in p35 knockout mice by immunoblot (120.7%±30.5% versus wild-type 100%±15.7%, n=4, p>0.5). Similarly, roscovitine treatment (10 μM, 45 min) of acute forebrain slices did not alter the levels of PSD-95 (103.7%±18.7% versus control slices 100%±15.8%, n=3, p>0.5; FIG. 3D). Thus, these results indicate that ubiquitination of PSD-95 does not correlate with decreased PSD-95 protein levels in vivo and are consistent with PSD-95 monoubiquitination. Together these data demonstrate that monoubiquitination of PSD-95 does not result in proteasome degradation of PSD-95, suggesting a nonproteolytic function for monoubiquitinated PSD-95 at the synapse.

Example 3

PSD-95 Monoubiquitination Promotes the Interaction of PSD-95 with β-Adaptin

Monoubiquitination and multiubiquitination have been implicated in a number of processes including endocytic adaptor function, trafficking, and sorting (Hicke and Dunn, 2003; Praefcke et al, 2004; Lefkowitz et al, 2006). PSD-95 ubiquitination has been implicated in NMDAR-induced AMPAR endocytosis (Colledge et al., 2003), which is mediated by the clathrin endocytic complex (Carroll et al., 1999; Man et al., 2000). The C-terminus of PSD-95 contains two copies of the tyrosine-based motif YXXΦ (Craven and Bredt, 2000), which mediates interaction with the plasma membrane adaptor complex AP-2, a complex involved in clathrin-mediated endocytosis (Ohno et al., 1995; Traub, 2009). Furthermore, there is evidence that PSD-95 interacts with AP-2 (Fernandez, et al., 2009) and that one YXXΦ motif of PSD-95 is sufficient to mediate clathrin-mediated endocytosis of a transmembrane receptor (Craven and Bredt, 2000). These studies and data indicating that PSD-95 is multiubiquitinated suggest a signaling function for ubiquitinated PSD-95 in the regulation of the interaction with AP-2 to mediate AMPAR endocytosis.

To evaluate whether monoubiquitination of PSD-95 regulates its interaction with the AP-2 complex, the impact of a HA-tagged ubiquitin mutant (HA-Ubi K0) (Lim et al., 2005) in which all lysines are mutated to arginine and therefore supports only mono-/multiubiquitination was analyzed, in transfected Cath.a-differentiated (CAD) cells (Qi et al., 1997). CAD cells, which express endogenous Mdm2 (data not shown), were transfected with PSD-95 and p35-Cdk5 or p35-DNK5, a dominant negative mutant of Cdk5 (Zhang et al., 2008), with or without HA-Ubi K0, and lysates were analyzed by immunoblot to control for the expression levels of transfected constructs (FIG. 4A). PSD-95 immunoprecipitated from transfected cells was analyzed for AP-2 interaction by immunoblotting for β-adaptin, a subunit of AP-2. Quantification of the immunoblots revealed that coexpression of HA-Ubi K0 with p35-DNK5 (inactive kinase) increases the interaction of β-adaptin with PSD-95 (97.2±52.5, n=2) compared to cells expressing only p35-DNK5 (10.6±4.3, n=2), or expressing HA-Ubi K0 and p35-Cdk5 (active kinase) (11.5±5.4, n=2) or only p35-Cdk5 (4.4±1.1, n=2). The increase in interaction of β-adaptin with PSD-95 was accompanied by an increase in ubiquitinated PSD-95 as indicated by the FK2 immunoblot (FIG. 4A). These data are consistent with a function for monoubiquitination in promoting PSD-95 interaction with the AP-2 complex.

To assess whether PSD-95 monoubiquitination correlates with increased PSD-95 interaction with AP-2 in vivo, p35 knockout mice were analyzed, which have increased PSD-95 monoubiquitination. PSD-95 immunoprecipitated from brain lysates of p35 knockout and wildtype littermates was analyzed by β-adaptin immunoblot (FIG. 4B). The interaction of β-adaptin with PSD-95 was significantly increased in p35 knockout mice (265%±55.8% versus wild-type, 100%±16.4%, n=4; p<0.05), indicating that reduced Cdk5 activity promotes the interaction of β-adaptin with PSD-95. To examine whether β-adaptin colocalization with PSD-95 puncta is also increased upon reduction of Cdk5 activity, the degree of colocalization in cultured hippocampal neurons in which Cdk5 was inhibited pharmacologically by roscovitine (FIG. 4C) was analyzed. Immunocytochemistry analysis of these cultures revealed that roscovitine treatment promotes increased colocalization of β-adaptin with PSD-95 puncta compared to DMSO control sister cultures (192.5%±19% versus control cultures 100%±15.6%, n=5, p<0.01). Together these data indicate that decreased Cdk5 activity recruits β-adaptin to PSD-95 puncta and promotes the interaction of β-adaptin with PSD-95. Since PSD-95 monoubiquitination is increased in these experimental conditions, these data are consistent with the interaction of monoubiquitinated PSD-95 with AP-2.

To further assess whether PSD-95 monoubiquitination regulates its interaction with AP-2 in vivo, mice mutant for Mdm2 were used. While mice deficient for Mdm2 die early in development, mice deficient for both Mdm2 and p53 develop normally and are viable (Jones et al., 1995). Therefore, PSD-95 immunoprecipitated from brain lysates of Mdm2/p53 double knockout mice and control p53 knockout mice were analyzed to determine the level of PSD-95 interaction with AP-2 (FIG. 4D). Immunoblot analysis of Mdm2/p53 double knockout brain lysates revealed decreased interaction of PSD-95 with β-adaptin compared to control p53 knockout mice (63.7%±8.8% versus control 100%±10.8%, n=5, p<0.05), indicating a correlation between PSD-95 monoubiquitination by Mdm2 and interaction with β-adaptin. Together these results demonstrate that PSD-95 monoubiquitination positively regulates the interaction of PSD-95 with β-adaptin and the AP-2/clathrin endocytic complex.

Example 4

Ubiquitination Promotes NMDAR-Dependent Interaction of β-Adaptin with PSD-95

PSD-95 is important for NMDAR-induced endocytosis of synaptic AMPARs (Colledge et al., 2003; Bhattacharyya et al., 2009) and a brief application of NMDA induces both a rapid and transient increase in PSD-95 ubiquitination, which peaks approximately 10 min after the onset of NMDA treatment (Colledge et al., 2003). Since our data suggest that monoubiquitination of PSD-95 promotes the interaction of β-adaptin with PSD-95, we investigated whether NMDA treatment induces a transient increase in β-adaptin interaction with PSD-95 that correlates with PSD-95 ubiquitination. Following a brief (3 min) stimulation with 100 μM NMDA, a treatment that induces AMPAR endocytosis (Bhattacharyya et al., 2009), acute forebrain slices from adult wildtype mice were analyzed at 5 min and 10 min after agonist washout. PSD-95 immunoprecipitated from slice lysates was analyzed for coimmunoprecipitation of β-adaptin and ubiquitination (FIG. 5A). The immunoblots indicate an increase in both PSD-95 interaction with β-adaptin and PSD-95 ubiquitination 10 min after the end of stimulation, indicating that NMDARs regulate both PSD-95 ubiquitination and interaction with β-adaptin and further supporting a correlation between PSD-95 ubiquitination and AP-2 interaction.

To further investigate whether ubiquitination of PSD-95 promotes the interaction of PSD-95 with β-adaptin, this interaction was investigated in acute brain slices derived from mice with a genetic deletion of the ubiquitin ligase Mdm2. Acute forebrain slices from adult Mdm2/p53 double knockout mice and control p53 knockout mice were analyzed at 5 min and 10 min after NMDA (100 μM, 3 min) washout. The interaction of PSD-95 with β-adaptin was assessed by immunoblot of PSD-95 immunoprecipitated from slice lysates (FIG. 5B). Analysis of PSD-95 from control p53 knockout mice revealed an increase in the interaction of PSD-95 with β-adaptin at 5 min after the end of NMDA treatment compared to unstimulated control (209.0%±72.6%, versus control 100%±14.9%, n=3) and a further increase at 10 min (549.8%±168%, n=3). The unstimulated slices from Mdm2/p53 double knockout mice had decreased interaction of PSD-95 with β-adaptin (50.5%±13.8% versus unstimulated control p53 knockout mice 100%±14.9%, n=3). In contrast to the p53 knockout mice, the NMDAR-dependent increase in PSD-95 interaction with β-adaptin was greatly reduced in Mdm2/p53 double knockout mice 5 min (45.6%±1.8%, n=3) and 10 min (99.8%±43.7%, n=3) after the end of NMDA treatment. These data demonstrate that Mdm2 regulates the NMDAR-induced interaction of PSD-95 with β-adaptin. Together these results indicate an NMDAR-induced time-dependent regulation of PSD-95 interaction with β-adaptin and implicate ubiquitination of PSD-95 in this regulation, consistent with a signaling function of ubiquitinated PSD-95 in the regulation of NMDAR-induced AMPAR endocytosis.

Example 5

Nutlin-3 Reduces Mdm2 Binding to PSD-95

Nutlin-3 is a potent pharmacological inhibitor of Mdm2 currently in a Phase I clinical trial for cancer therapy. Its mechanism of action involves disrupting the interaction of Mdm2 with the tumor suppressor p53, thereby inhibiting p53 ubiquitination by Mdm2. Given that p53 and several other Mdm2 substrates bind to the same region of Mdm2 (Marine and Lozano, 2010), it was hypothesized that Nutlin-3 would also inhibit PSD-95 ubiquitination, a known substrate of Mdm2 (College et al., 2003).

To test this hypothesis, acute mouse forebrain slices were prepared and subjected to treatment with or without Nutlin-3. The interaction between PSD95 and Mdm2 was assessed by immunoprecipitation of Mdm2, followed by Western blot analysis to assess the extent of PSD-95 binding. Consistent with PSD-95 binding to the same region of Mdm2 as other Mdm2 substrates, Nutlin-3 decreased the interaction between PSD-95 with Mdm2 by 60% (FIGS. 6A and B).

Example 6

Nutlin-3 Reduces NMDAR-Induced AMPAR Endocytosis

Brief stimulation of NMDARs induces AMPAR endocytosis in cultured neurons (Colledge et al., 2003; Bhattacharyya et al., 2009). To determine whether Nutlin-3a antagonizes NMDA-induced AMPAR endocytosis, measured as loss of surface AMPAR staining, the surface expression of GluA2 (a subunit of AMPARs in rat hippocampal cultures) was assessed. Surface GluA2 were labeled in vivo by an antibody feeding protocol using an antibody that recognizes an extracellular domain of GluA2 (Ehlers, 2000; Lin et al., 2000; Bhattacharyya et al., 2009). Neurons were pretreated with Nutlin-3a (5 μM for 30 min) prior to NMDA treatment. After brief stimulation with NMDA (100 μM for 3 min) and agonist washout, neurons were incubated for an additional 15 min (with or without Nutlin-3a) before immunocytochemical analysis of PSD-95 and surface GluA2 by confocal microscopy under the same settings. Immunostained puncta were quantified using MetaMorph software (3 neurons from 2 coverslips with approximately 450 puncta analyzed/condition) and the number of GluA2 puncta was normalized to the number of PSD-95 puncta.

Naïve and NMDA-stimulated conditions were used as controls. GluA2 surface expression was decreased following NMDA stimulation, as expected, and this decrease was attenuated in neurons treated with Nutlin-3 (41.95±9.63% and 60.86±3.98%, respectively, versus 100%±9.47%, naïve control, n=3, p<0.01, ANOVA) (FIGS. 7A and B). Importantly, PSD-95 puncta did not decrease following NMDA stimulation of naïve cultures, a result consistent with unchanged PSD-95 protein levels in rat cortical neuronal cultures stimulated with NMDA (data not shown), with the monoubiquitination of PSD-95 on multiple sites and the similar PSD-95 protein levels observed under conditions that promote PSD-95 ubiquitination. These findings suggest a decrease in AMPAR internalization upon Nutlin-3a treatment and are consistent with the hypothesis that inhibitors of Mdm2 antagonize the endocytosis of AMPARs induced by NMDAR. Similar results are expected with other inhibitors of PSD-95 ubiquitination by Mdm2 and/or Mdm4, such as inhibitors that inhibit the interaction between PSD-95 and Mdm2 and/or Mdm4.

Example 7

Nutlin-3 and HLI373 Reduce Aft-Induced AMPAR Endocytosis

Cognitive impairment in Alzheimer's Disease (AD) correlates strongly with increased levels of soluble amyloid beta (Aβ) peptides and with alterations and loss of synapses. Soluble Aβ peptides affect cognitive processes by depressing excitatory synaptic transmission and disrupting synaptic structure and function. A molecular correlate of Aβ-induced synaptic dysfunction is a decrease in the surface expression of glutamate AMPA- and NMDA-type receptors. Thus pharmacological strategies that block Aβ-induced endocytosis of glutamate receptors may prevent the synaptic dysfunction and cognitive decline observed in AD.

Soluble amyloid beta (Aβ) peptides contribute directly to synapse loss and decreased dendritic spine density and glutamate receptors at the synapse. Moreover, Aβ has been reported to induce AMPAR internalization in cultured neurons. To evaluate the effect of Mdm2 inhibitors on this process, cultured rat hippocampal neurons were treated for 2 hrs with Aβ (or Aβ together with either Nutlin-3 (5 µM) or HLI-373 (15 µM). Aβ can be prepared from 7PA2 Chinese hamster ovary (CHO) cells stably expressing human amyloid precursor protein (APP)751 containing the V717 mutation (Walsh et al., 2005; Shankar et al., 2007; Shankar et al., 2011), and is also available commercially from, e.g., rPeptide (Bogart, G A). The concentration of Aβ in the hippocampal cultures was 0.3 ng/mL. Naïve and Nutlin-3 and HLI-373 treatments were used as controls. Surface expression of AMPARs was measured by labeling the cultured neurons in vivo with an antibody to the AMPAR subunit GluA1, followed by confocal microscopy and immunofluorescence quantification by MetaMorph. The number of GluA1 puncta was normalized to SV2 puncta (a presynaptic marker) and to the value in control naïve cultures (see FIGS. 8A and B).

In control cultures, Nutlin-3 treatment did not result in substantial changes in GluA1 surface expression compared to naïve cultures, while HLI-373 treatment resulted in an increase in GluA1 surface expression (90.6%±3.71% and 170.95%±5.37% respectively, versus 100%±4% naïve control; n=3, p<0.001, ANOVA), suggesting a larger effect of HLI-373, possibly due to the direct inhibition of Mdm2 activity, which could affect a wider range of Mdm2 substrates than Nutlin-3a. After treatment with Aβ, there was an expected decrease in surface expression of GluA1 (58.34%±2% versus 100%±4% naïve control; n=3, p<0.01, ANOVA). When neurons were co-treated with Aβ and either Nutlin-3a or HLI373, a clear decrease in Aβ-induced internalization of GluA1 was observed (152.29%±19.88% and 132.18%±11.33%, respectively, versus 100%±4% naïve control; n=3, p<0.001, ANOVA). These data are consistent with the blockage of Aβ-induced endocytosis of AMPARs with Nutlin-3a and HLI-373. Minimum inhibitor concentrations of Nutlin-3a or HLI-373, as well as any other Mdm2 inhibitor identified using the screens described supra, can be readily determined by using different ranges of inhibitor concentrations and assessing the effects of the particular concentrations on surface expression of AMPARs. Similar results are expected with other inhibitors of PSD-95 ubiquitination by Mdm2, such as PSD-95 inhibitors.

Example 8 (Prophetic)

Effects of Nutlin-3a, HLI373, and PSD-95 Inhibitors on Surface Expression of Receptors in Neurons Cultured from an AD Model Cultured neurons derived from transgenic AD mouse models secrete elevated levels of Aβ and have altered pre- and post-synaptic compartments with decreased levels of AMPARs and NMDARs and fewer synapses (Almeida et al., 2005; Snyder et al., 2005). AMPAR internalization can also be induced by treating cultured hippocampal neurons with Aβ prepared from 7PA2 cells (Walsh et al. 2005; Shankar et al., 2007; Shankar et al., 2011). As demonstrated in Example 7, Nutlin-3a and HLI-373 reduce AMPAR endocytosis induced by exogenous Aβ. Moreover, a reduction in surface expression of NMDARs is observed in cultured neurons treated with exogenous Aβ peptides as well as in neuronal cultures from an AD mouse model (Snyder et al., 2005).

To further evaluate the efficacy of Mdm2 inhibitors in reducing Aβ-induced synaptic alterations, embryonic hippocampal neurons are cultured from E16 triple transgenic (3xTg-AD) AD mice, which produce endogenous Aβ (Oddo et al., 2003), and are treated with or without Nutlin-3a or HLI-373. Controls are cultures derived from wild-type mice. AMPAR and NMDAR surface expression are assessed by labeling AMPAR subunits GluA1 and/or GluA2 or NMDAR subunit NR1 by an antibody feeding protocol and analyzing the density and size of AMPAR or NMDAR puncta (Ehlers, 2000; Lin et al., 2000; Bhattacharyya et al., 2009). Briefly, surface AMPARs or NMDARs are labeled in live neurons with an antibody against the extracellular portion of GluA1 or GluA2, or NR1, respectively, as carried out by art-recognized methods. After treatments, neurons are fixed, labeled with conjugated secondary antibodies (to label the GluA1 or GluA2, or NR1, still on the surface), then permeabilized and immunostained for postsynaptic markers such as PSD-95 (to analyze the colocalization with GluA1/GluA2 or NR1 puncta) and for presynaptic markers such as synapsin 1 or Bassoon (to identify synapses). Control experiments are conducted to assure the specificity of the immunostaining. Experiments are done using sister cultures. All images are collected by confocal microscopy using similar settings and analyzed blind, with 10-20 neurons/condition, each from 3-5 separate experiments. Maximum projection reconstructions of Z-series confocal images are used and the number and size of GluA1 or GluA2, PSD-95, and presynaptic puncta are quantified by MetaMorph software as done routinely in the laboratory (Zhang et al., 2008; Bianchetta et al., 2011). These experiments will determine the range of concentration and length of Nutlin-3a or HLI373 treatments necessary to observe an antagonistic effect on Aβ-induced AMPAR endocytosis.

Surface biotinylation assays (Lin et al., 2000; Man et al., 2000) are also carried out for a biochemical readout of surface AMPAR and NMDAR expression. The surface biotinylation assay involves incubating hippocampal or cortical neuron cultures with Sulfo-NHS-LC-Biotin (commercially available from, e.g., Thermo Scientific) to label proteins expressed on the cell surface after the various treatments described supra. The biotin-labeled proteins are isolated by incubation with neutravidin agarose beads (commercially available from, e.g., ThermoScientific) and analyzed by quantitative western blots using GluA1 or GluA2 antibodies (for AMPARs) or NR1 antibodies (for NMDARs), or transferrin antibody as control. The amount of GluA1- or GluA2-containing AMPARs or NR1-containing NMDARs still at the cell surface after the treatments are compared with the amount in naïve cultures and cultures treated only with Aβ. In complementary experiments, the amount of internalized AMPAR or NMDAR subunits is assessed after the various treatments. Briefly, receptors on the cell-surface of cultured neurons are labeled with Sulfo-NHS-LC-Biotin prior to treatments, the remaining surface biotin will be cleaved with glutathione, and cultures are lysed. Biotinylated proteins are then be isolated by neutravidin agarose beads and analyzed by quantitative immunoblot.

Further, dendritic spine density and electrophysiological properties (by patch-clamp whole-cell recordings) are assessed using art-recognized methods as described in, e.g., Honig and Hume 1986; Kim et al., 2007; Futai et al., 2007; Bhattacharyya et al., 2009; and Kim et al., 2007.

Treatment of these neurons with Nutlin-3a and HLI-373 are expected to increase the surface expression of AMPARs and NMDARs, increase dendritic spine density, and increase the frequency and amplitude of miniature excitatory postsynaptic currents compared to untreated or vehicle treated cells. Any increase observed in the cell surface expression of AMPARs or NMDARs is indicative of an effect of Mdm2 inhibitors on GluA1-containing AMPARs or NR1-containing NMDARs.

Example 9 (Prophetic)

Treatment of Cognitive Deficits and Synaptic Dysfunction in Neurological Disorders 3xTg-AD mice will be used as a model neurological disorder to test the effects of Mdm2 inhibitors on cognitive deficits and synaptic dysfunction observed in these mice. 3xTg-AD mice develop age-related cognitive decline and impairment in synaptic plasticity, with robust cognitive decline and LTP deficits by 6 months of age (Oddo et al., 2003; Billings et al., 2005). Moreover, decreased dendritic spine density has been reported in transgenic mouse models of AD (Dong et al., 2007; Spires-Jones et al., 2007; Bittner et al., 2010).

Nutlin-3a is initially administered by oral gavage, at 100 mg/kg once daily. At this dose, Nutlin-3a reaches a concentration of 1-2 µM in brain tissue between 1-8 hours after administration (Zhang et al., 2011). Nutlin-3a can be replaced with HLI-373 (inhibits Mdm2 activity by binding to the catalytic domain; Kitagaki et al., 2008) or any other known Mdm2 and/or Mdm4 inhibitor or PSD-95 inhibitor that can cross the blood-brain barrier. It is within the abilities of one of ordinary skill to determine whether a Mdm2 and/or Mdm4 inhibitor or PSD-95 inhibitor can cross the blood-brain barrier, and optimal concentrations can be readily determined.

A second series of experiments will test chronic Nutlin-3a or PSD-95 inhibitor treatment (at a daily dose of 100 mg/kg for a total of 14 days) by art-recognized behavioral (e.g., novel object recognition tasks to test non-spatial hippocampal-dependent memory, Y-maze to assess spontaneous alteration behavior), electrophysiological (i.e., to assess excitatory synaptic transmission and synaptic plasticity), and synapse/dendritic spine analysis as described supra. 3xTg-AD mice are known to be significantly impaired in the Y-maze task at 6 months (Billings et al., 2005). Controls include wild type mice and vehicle treated littermates treated with Nutlin-3a or PSD-95 inhibitor. Nutlin-3a is not expected to be toxic in mice (Van Maerken et al., 2009). Methods of electrophysiological and dendritic spine analyses are carried out using methods known in the art (e.g., as described in Honig et al., 1986; Kim et al., 2007, Bhattacharyya et al., 2009; Futai et al., 2007; Nakagawa et al., 2004; and Schluter et al., 2006) and as described supra.

It is expected that Nutlin-3a- or PSD-95 inhibitor-treated 3xTg-AD mice will exhibit improvements in cognitive tasks, electrophysiology, and synapse/dendritic spine density compared to vehicle treated 3xTg-AD mice. Methods for carrying out these evaluations are well-established.

While this embodiment is specific to an AD mouse model, it is within the abilities of one of ordinary skill to carry out related experiments and assess the same parameters (e.g., behavior, electrophysiology, dendritic spine morphology and density) in different animal models using similar techniques as that described supra.

REFERENCES

Almeida C G, Tampellini D, Takahashi R H, Greengard P, Lin M T, Snyder E M, Gouras G K. (2005). Beta-amyloid accumulation in APP mutant neurons reduces PSD-95 and GluR1 in synapses. Neurobiol Dis. 20: 187-198.

Altschul, et al. (1990) J. Mol. Biol. 215:403-10.

Angelo M, Plattner F, Giese K P. (2006). Cyclin-dependent kinase 5 in synaptic plasticity, learning and memory. J. Neurochem. 99:3 53-70.

Armstrong D M, Ikonomovic M D, Sheffield R, Wenthold R J. (1994). AMPA-selective glutamate receptor subtype immunoreactivity in the entorhinal cortex of non-demented elderly and patients with Alzheimer's disease. Brain Res. 639: 207-216.

Askew et al., Am. J. Chem. Soc. 111:1082-1090

Badciong J C and Haas A L. (2002). MdmX is a RING finger ubiquitin ligase capable of synergistically enhancing Mdm2 ubiquitination. JBC. 277: 49668-75.

Bats C, Groc L, Choquet D. (2007). The interaction between Stargazin and PSD-95 regulates AMPA receptor surface trafficking. Neuron. 53: 719-34.

Béïque J C, Andrade R. (2003). PSD-95 regulates synaptic transmission and plasticity in rat cerebral cortex. J. Physiol. 546: 859-67.

BéïJ C, Lin D T, Kang M G, Aizawa H, Takamiya K, Huganir R L. (2006). Synapse-specific regulation of AMPA receptor function by PSD-95. Proc Natl Acad Sci USA. 103: 19535-40.

Benosman S, Gross I, Clarke N, Jochemsen A G, Okamoto K, Loeffler J P, Gaiddon C. Multiple neurotoxic stresses converge on MDMX proteolysis to cause neuronal apoptosis. Cell Death Differ. 2007 December; 14(12):2047-57. Epub 2007 Sep. 7.

Bhattacharyya S, Biou V, Xu W, Schlüter O, Malenka R C. (2009). A critical role for PSD-95/AKAP interactions in endocytosis of synaptic AMPA receptors. Nat. Neurosci. 12: 172-81.

Bianchetta M J, Lam T T, Jones S N, Morabito M A. (2011). Cyclin-dependent kinase 5 regulates PSD-95 ubiquitination in neurons. J. Neurosci. 31:12029-12035.

Billings L M, Oddo S, Green K N, McGaugh J L, LaFerla F M. (2005). Intraneuronal Abeta causes the onset of early Alzheimer's disease-related cognitive deficits in transgenic mice. Neuron 45:675-688

Bingol B, Schuman E M. (2004). A proteasome-sensitive connection between PSD-95 and GluR1 endocytosis. Neuropharmacology. 47: 755-63.

Bittner T, Fuhrmann M, Burgold S, Ochs S M, Hoffmann N, Mitteregger G, Kretzschmar H, LaFerla F M, Herms J. (2010). Multiple events lead to dendritic spine loss in triple transgenic Alzheimer's disease mice. PLoS One. 5:e15477.

Blanpied T A, Scott D B, Ehlers M D. Neuron. 2002 Oct. 24; 36(3):435-49.

Carroll R C, Beattie E C, Xia H, Liischer C, Altschuler Y, Nicoll R A, Malenka R C, von Zastrow M. (1999). Dynamin-dependent endocytosis of ionotropic glutamate receptors. Proc Natl Acad Sci USA. 96: 14112-7.

Carter T L, Rissman R A, Mishizen-Eberz A J, Wolfe B B, Hamilton R L, Gandy S, Armstrong D M. (2004). Differential preservation of AMPA receptor subunits in the hippocampi of Alzheimer's disease patients according to Braak stage. Exp Neurol. 187: 299-309.

Casten K S, Gray A C, Burwell R D. Discrimination learning and attentional set formation in a mouse model of Fragile X. Behav Neurosci. 2011 June; 125(3):473-9.

Cha J H, Farrell L A, Ahmed S F, Frey A, Hsiao-Ashe K K, Young A B, Penney J B, Locascio J J, Hyman B T, Irizarry M C. (2001). Glutamate receptor dysregulation in the hippocampus of transgenic mice carrying mutated human amyloid precursor protein. Neurobiol Dis. 8: 90-102.

Chae T, Kwon Y T, Bronson R, Dikkes P, Li E, Tsai L H. (1997). Mice lacking p35, a neuronal specific activator of Cdk5, display cortical lamination defects, seizures, and adult lethality. Neuron 18: 29-42.

Chang E H, Savage M J, Flood D G, Thomas J M, Levy R B, Mahadomrongkul V, Shirao T, Aoki C, Huerta P T. (2006). AMPA receptor downscaling at the onset of Alzheimer's disease pathology in double knockin mice. Proc Natl Acad Sci USA. 103: 3410-3415.

Chen L, Chetkovich D M, Petralia R S, Sweeney N T, Kawasaki Y, Wenthold R J, Bredt D S, Nicoll R A. (2000). Stargazin regulates synaptic targeting of AMPA receptors by two distinct mechanisms. Nature 408: 936-43.

Chène P. Inhibition of the p53-MDM2 interaction: targeting a protein-protein interface. Mol Cancer Res. 2004 January; 2(1):20-8.

Cheung Z H, Fu A K, Ip N Y. (2006). Synaptic roles of Cdk5: implications in higher cognitive functions and neurodegenerative diseases. Neuron 50: 13-8.

Chin J H, Ma L, MacTavish D, Jhamandas J H. (2007). Amyloid beta protein modulates glutamate-mediated neurotransmission in the rat basal forebrain: involvement of presynaptic neuronal nicotinic acetylcholine and metabotropic glutamate receptors. J. Neurosci. 27: 9262-9269.

Chin J. Selecting a mouse model of Alzheimer's disease. Methods Mol. Biol. 2011; 670:169-89. Review.

Citri A, Soler-Llavina G, Bhattacharyya S, Malenka R C. (2009). N-methyl-D-aspartate receptor and metabotropic glutamate receptor-dependent long-term depression are differentially regulated by the ubiquitin-proteasome system. Eur J. Neurosci. 30: 1443-50.

Cleary J P, Walsh D M, Hofineister J J, Shankar G M, Kuskowski M A, Selkoe D J, Ashe K H. (2005). Natural oligomers of the amyloid-beta protein specifically disrupt cognitive function. Nat. Neurosci. 8: 79-84.

Coligan et al. (Current Protocols in Immunology, John Wiley & Sons, Inc., 1994, see Volume 1, chapter 2)

Colledge M, Snyder E M, Crozier R A, Soderling J A, Jin Y, Langeberg L K, Lu H, Bear M F, Scott J D. (2003). Ubiquitination regulates PSD-95 degradation and AMPA receptor surface expression. Neuron 40: 595-607.

Craven S E, Bredt D S. (2000). Synaptic targeting of the postsynaptic density protein PSD-95 mediated by a tyrosine-based trafficking signal. J Biol. Chem. 275: 20045-51.

*CRC Handbook of Parvoviruses*, vol. I & II (P. Tijssen, ed.)

d'Azzo A, Bongiovanni A, Nastasi T. (2005). E3 ubiquitin ligases as regulators of membrane protein trafficking and degradation. Traffic 6: 429-41.

Dehay B, Bezard E. New animal models of Parkinson's disease. Mov Disord. 2011 June; 26(7):1198-1205. Review.

DeKosky S T, Scheff S W. (1990). Synapse loss in frontal cortex biopsies in Alzheimer's disease: correlation with cognitive severity. Ann Neurol. 27: 457-464.

DeKosky S T, Scheff S W, Styren S D. (1996). Structural correlates of cognition in dementia: quantification and assessment of synapse change. Neurodegeneration. 5: 417-421.

Design pp. 189-193 (Alan R. Liss, Inc., 1989)

DiAntonio A, Hicke L. (2004). Ubiquitin-dependent regulation of the synapse. Annu Rev Neurosci. 27: 223-46.

*DNA Cloning: A Practical Approach*, vol. I & II (D. Glover, ed.)

Donehower L A, Harvey M, Slagle B L, McArthur M J, Montgomery C A Jr, Butel J S, Bradley A. (1992). Mice deficient for p53 are developmentally normal but susceptible to spontaneous tumours. Nature 356: 215-21.

Dong H, Martin M V, Chambers S, Csernansky J G. (2007). Spatial relationship between synapse loss and beta-amyloid deposition in Tg2576 mice. J Comp Neurol. 500: 311-321.

Ehlers M D. (2000). Reinsertion or degradation of AMPA receptors determined by activity-dependent endocytic sorting. Neuron. 28: 511-525.

Ehlers M D. (2003). Activity level controls postsynaptic composition and signaling via the ubiquitin-proteasome system. Nat. Neurosci. 6: 231-42. Ehrlich I, Malinow R. (2004). Postsynaptic density 95 controls AMPA receptor incorporation during long-term potentiation and experience-driven synaptic plasticity. J. Neurosci. 24: 916-27.

El-Husseini A E, Schnell E, Chetkovich D M, Nicoll R A, Bredt D S. (2000). PSD-95 involvement in maturation of excitatory synapses. Science 290: 1364-8.

Elias G M, Funke L, Stein V, Grant S G, Bredt D S, Nicoll R A. (2006). Synapse-specific and developmentally regulated targeting of AMPA receptors by a family of MAGUK scaffolding proteins. Neuron. 52: 307-20.

Elias G M, Nicoll R A. (2007). Synaptic trafficking of glutamate receptors by MAGUK scaffolding proteins. Trends Cell Biol. 17: 343-52.

Elliott P. J., Zollner T. M. and Boehncke W. H., (2003). Proteasome inhibition: a new antiinflammatory strategy, J. Mol. Med. 81: 235-245.

Fernandez E, Collins M O, Uren R T, Kopanitsa M V, Komiyama N H, Croning M D R, Zografos L, Armstrong J D, Choudhary J S, Grant S G N. (2009). Targeted tandem affinity purification of PSD-95 recovers core postsynaptic complexes and schizophrenia susceptibility proteins. Mol Sys Biol. 5: 269.

Fischer P M. Peptide, peptidomimetic, and small-molecule antagonists of the p53-HDM2 protein-protein interaction. Int J Peptide Res Ther 2006; 12:3-19.

Fujimuro M, Sawada H, Yokosawa H. (1994). Production and characterization of monoclonal antibodies specific to multi-ubiquitin chains of polyubiquitinated proteins. FEBS Lett. 349: 173-80.

*Fundamental Virology*, 2nd Edition, vol. I & II (B. N. Fields and D. M. Knipe, eds.)

Funke L, Dakoji S, Bredt D S. (2005). Membrane-associated guanylate kinases regulate adhesion and plasticity at cell junctions. Annu Rev Biochem. 74: 219-45.

Futai K, Kim M J, Hashikawa T, Scheiffele P, Sheng M, Hayashi Y. (2007). Retrograde modulation of presynaptic release probability through signaling mediated by PSD-95-neuroligin. Nat. Neurosci. 10: 186-95.

Garcia R A, Vasudevan K, Buonanno A. The neuregulin receptor ErbB-4 interacts with PDZ-containing proteins at neuronal synapses. Proc Natl Acad Sci USA. 2000 Mar. 28; 97(7):3596-601

Gascón S, Sobrado M, Roda J M, Rodríguez-Peña A, Diaz-Guerra M. (2008). Excitotoxicity and focal cerebral ischemia induce truncation of the NR2A and NR2B subunits of the NMDA receptor and cleavage of the scaffolding protein PSD-95. Mol Psychiatry 13: 99-114.

Gavin A C, Bösche M, Krause R, Grandi P, Marzioch M, Bauer A, Schultz J, Rick J M, Michon A M, Cruciat C M, Remor M, Höfert C, Schelder M, Brajenovic M, Ruffner H, Merino A, Klein K, Hudak M, Dickson D, Rudi T, Gnau V, Bauch A, Bastuck S, Huhse B, Leutwein C, Heurtier M A, Copley R R, Edelmann A, Querfurth E, Rybin V, Drewes G, Raida M, Bouwmeester T, Bork P, Seraphin B, Kuster B, Neubauer G, Superti-Furga G. Nature. 2002 Jan. 10; 415(6868):141-7.

Geddes J W, Ulas J, Brunner L C, Choe W, Cotman C W. (1992). Hippocampal excitatory amino acid receptors in elderly, normal individuals and those with Alzheimer's disease: non-N-methyl-D-aspartate receptors. Neuroscience. 50: 23-34.

Goodman and Ro., Peptidomimetics for Drug Design, in "Burger's Medicinal Chemistry and Drug Discovery" Vol. 1 (ed. M. E. Wolff; John Wiley and Sons 1995).

Hallows J L, Iosif R E, Biasell R D, Vincent I. (2006). p35/p25 is not essential for tau and cytoskeletal pathology or neuronal loss in Niemann-Pick type C disease. J. Neurosci. 26: 2738-44.

Hawasli A H, Benavides D R, Nguyen C, Kansy J W, Hayashi K, Chambon P, Greengard P, Powell C M, Cooper D C, Bibb J A. (2007). Cyclin-dependent kinase 5 governs learning and synaptic plasticity via control of NMDAR degradation. Nat. Neurosci. 10: 880-6.

Hamajima et al. (1998), Clin. Immunol. Immunopathol., 88(2), 205-10.

Hardcastle I R. Inhibitors of the MDM2-p53 interaction as anticancer drugs. Drugs Fut 2007; 32:883-96.

Hawasli A H, Bibb J A. (2007). Alternative roles for Cdk5 in learning and synaptic plasticity. Biotechnol J. 2: 941-8.

Hicke L, Dunn R. (2003). Regulation of membrane protein transport by ubiquitin and ubiquitin binding proteins. Annu Rev Cell Dev Biol. 19: 141-72.

Hoe H S, Pocivaysek A, Chakraborty G, Fu Z, Vicini S, Ehlers M D, Rebeck G W. Apolipoprotein E receptor 2 interactions with the N-methyl-D-aspartate receptor. J Biol. Chem. 2006 Feb. 10; 281(6):3425-31.

Honig M G, Hume R I. (1986). Fluorescent carbocyanine dyes allow living neurons of identified origin to be studied in long-term cultures. J. Cell Biol. 103: 171-187.

Houghten et al., Nature 354:84-86, 1991

Hsieh H, Boehm J, Sato C, Iwatsubo T, Tomita T, Sisodia S, Malinow R. (2006). AMPAR removal underlies Abeta-induced synaptic depression and dendritic spine loss. Neuron. 52: 831-843.

Hu C Q, Hu Y Z. Small molecule inhibitors of the p53-MDM2. Curr Med. Chem. 2008; 15(17):1720-30.

Hunsaker M R, Argue G, Berman R F, Willemsen R, Hukema R K. Mouse models of the fragile x premutation and the fragile x associated tremor/ataxia syndrome. Results Probl Cell Differ. 2012; 54:255-69.

Ikonomovic M D, Sheffield R, Armstrong D M. (1995). AMPA-selective glutamate receptor subtype immunoreactivity in the hippocampal formation of patients with Alzheimer's disease. Hippocampus. 5: 469-486.

Jones S N, Roe A E, Donehower L A, Bradley A. (1995). Rescue of embryonic lethality in Mdm2-deficient mice by absence of p53. Nature. 378: 206-8.

Kalia L V, Pitcher G M, Pelkey K A, Salter M W. (2006). PSD-95 is a negative regulator of the tyrosine kinase Src in the NMDA receptor complex. EMBO J. 25: 4971-82.

Karlin and Altschul (1990) Proc. Natl. Acad. Sci. USA 87:2264-68.

Karlin and Altschul (1993) Proc. Natl. Acad. Sci. USA 90:5873-77.

Karlsgodt K H, Sun D, Jimenez A M, Lutkenhoff E S, Wilhite R, van Erp T G, Cannon T D. Developmental disruptions in neural connectivity in the pathophysiology of schizophrenia. Dev Psychopathol. 2008 Fall; 20(4): 1297-327.

Kim E, Sheng M. (2004). PDZ domain proteins of synapses. Nat Rev Neurosci. 5: 771-81.

Kim M J, Futai K, Jo J, Hayashi Y, Cho K, Sheng M. (2007). Synaptic accumulation of PSD-95 and synaptic function regulated by phosphorylation of serine-295 of PSD-95. Neuron. 56:488-502.

Kitagaki J, Agama K K, Pommier Y, Yang Y, Weissman A M. Mol Cancer Ther. 2008 August; 7(8):2445-54. Targeting tumor cells expressing p53 with a water-soluble inhibitor of Hdm2.

Knobloch M, Mansuy I M. (2008). Dendritic spine loss and synaptic alterations in Alzheimer's disease. Mol. Neurobiol. 37: 73-82.

Krogan N J, Greenblatt J F. Mol Cell Biol. 2001 December; 21(23):8203-12.

Lacor P N, Buniel M C, Chang L, Fernandez S J, Gong Y, Viola K L, Lambert M P, Velasco P T, Bigio E H, Finch C E, Krafft G A, Klein W L. (2004). Synaptic targeting by Alzheimer's-related amyloid beta oligomers. J. Neurosci. 24: 10191-10200.

Lacor P N, Buniel M C, Furlow P W, Clemente A S, Velasco P T, Wood M, Viola K L, Klein W L (2007). Abeta oligomer-induced aberrations in synapse composition, shape, and density provide a molecular basis for loss of connectivity in Alzheimer's disease. J. Neurosci. 27: 796-807.

Lai K O, Ip N Y. (2009). Recent advances in understanding the roles of Cdk5 in synaptic plasticity. Biochim Biophys Acta. 1792: 741-5

Lam et al., Nature 354:82-84, 1991

Lambert M P, Barlow A K, Chromy B A, Edwards C, Freed R, Liosatos M, Morgan T E, Rozovsky I, Trommer B, Viola K L, Wals P, Zhang C, Finch C E, Krafft G A, Klein W L. (1998). Diffusible, nonfibrillar ligands derived from Abeta1-42 are potent central nervous system neurotoxins. Proc Natl Acad Sci USA. 95: 6448-6453.

Lavezzari G, McCallum J, Dewey C M, Roche K W. J. Neurosci. 2004 Jul. 14; 24(28):6383-91.

Lee D H and Goldberg A L. (1998). Proteasome inhibitors: valuable new tools for cell biologists. Trends Cell Biol. 8: 397-403.

Lee H K, Kameyama K, Huganir R L, Bear M F. (1998). NMDA induces long-term synaptic depression and dephosphorylation of the GluR1 subunit of AMPA receptors in hippocampus. Neuron 21: 1151-62.

Lefkowitz R J, Rajagopal K, Whalen E J. (2006). New roles for beta-arrestins in cell signaling: not just for seven-transmembrane receptors. Mol. Cell. 24: 643-52.

Lewis and Dean, Proc. R. Soc. Lond. 236:125-140, 141-162, 1989

Li M, Brooks C L, Wu-Baer F, Chen D, Baer R, Gu W. (2003). Mono-versus polyubiquitination: differential control of p53 fate by Mdm2. Science. 302: 1972-5.

Li S, Hong S, Shepardson N E, Walsh D M, Shankar G M, Selkoe D. (2009). Soluble oligomers of amyloid Beta protein facilitate hippocampal long-term depression by disrupting neuronal glutamate uptake. Neuron. 62: 788-801.

Li et al., *JBC* 2002; 277:50607-11

Li Z, Jo J, Jia J M, Lo S C, Whitcomb D J, Jiao S, Cho K, Sheng M. (2010). Caspase-3 activation via mitochondria is required for long-term depression and AMPA receptor internalization. Cell. 141: 859-71.

Lim K L, Chew K C, Tan J M, Wang C, Chung K K, Zhang Y, Tanaka Y, Smith W, Engelender S, Ross C A, Dawson V L, Dawson T M. (2005). Parkin mediates nonclassical, proteasomal-independent ubiquitination of synphilin-1: implications for Lewy body formation. J. Neurosci. 25: 2002-9.

Lin J W, Ju W, Foster K, Lee S H, Ahmadian G, Wyszynski M, Wang Y T, Sheng M. (2000). Distinct molecular mechanisms and divergent endocytotic pathways of AMPA receptor internalization. Nat. Neurosci. 3: 1282-1290.

Lu X, Rong Y, Baudry M. (2000). Calpain-mediated degradation of PSD-95 in developing and adult rat brain. Neurosci Lett. 286: 149-53.

Lue L F, Kuo Y M, Roher A E, Brachova L, Shen Y, Sue L, Beach T, Kurth J H, Rydel R E, Rogers J. (1999). Soluble amyloid beta peptide concentration as a predictor of synaptic change in Alzheimer's disease. Am J. Pathol. 155: 853-862.

Mabb A M, Ehlers M D. (2010). Ubiquitination in postsynaptic function and plasticity. Annu Rev Cell Dev Biol. 26: 179-210.

Malinow R, Malenka R C. (2002). AMPA receptor trafficking and synaptic plasticity. Annu Rev Neurosci. 25: 103-126.

Man H Y, Lin J W, Ju W H, Ahmadian G, Liu L, Becker L E, Sheng M, Wang Y T. (2000). Regulation of AMPA receptor-mediated synaptic transmission by clathrin-dependent receptor internalization. Neuron 25: 649-62.

Marine J C, Lozano G. (2010) Mdm2-mediated ubiquitilation: p53 and beyond. Cell Death Differ. 17: 93-102.

Masliah E. (1997). Role of amyloid precursor protein in the mechanisms of neurodegeneration in Alzheimer's disease. Lab Invest. 77: 197-209.

Mayes L C. Developing brain and in utero cocaine exposure: effects on neural ontogeny. Dev Psychopathol. 1999 Fall; 11(4):685-714.

McCaffrey et al. (2002), Nature, 418(6893), 38-9 (hydrodymanic transfection)

McCoy et al., PNAS 2003; 100:1645-48

McKinaly and Rossmann, Ann. Rev. Pharmacol. Toxicol. 29:111-122, 1989

McLean C A, Chemy R A, Fraser F W, Fuller S J, Smith M J, Beyreuther K, Bush A I, Masters C L. (1999). Soluble pool of Abeta amyloid as a determinant of severity of neurodegeneration in Alzheimer's disease. Ann Neurol. 46: 860-866.

Moll U M, Petrenko O. The MDM2-p53 interaction. Mol Cancer Res. 2003 December; 1(14):1001-8.

Morabito M A, Sheng M, Tsai L H. (2004). Cyclin-dependent kinase 5 phosphorylates the N-terminal domain of the postsynaptic density protein PSD-95 in neurons. J. Neurosci. 24: 865-76.

Moy S S, Nadler J J. Advances in behavioral genetics: mouse models of autism. *Mol. Psychiatry.* 2008 January; 13(1):4-26.

Murray J K, Gellman S H. Targeting protein-protein interactions: lessons from p53/MDM2. Biopolymers 2007; 88:657-86.

Mukhopadhyay D, Riezman H. (2007). Proteasome-independent functions of ubiquitin in endocytosis and signaling. Science. 315: 201-5.

Nakagawa T, Futai K, Lashuel H A, Lo I, Okamoto K, Walz T, Hayashi Y, Sheng M. (2004). Quaternary structure, protein dynamics, and synaptic function of SAP97 controlled by L27 domain interactions. Neuron. 44: 453-67.

Nestler E J, Hyman S E. Animal models of neuropsychiatric disorders. Nat. Neurosci. 2010 October; 13(10):1161-9. Epub 2010 Sep. 27. Review.

Niethammer M, Kim E, Sheng M. J. Neurosci. 1996 Apr. 1; 16(7):2157-63.

*Nucleic Acid Hybridization* (B. Hames & S. Higgins, eds., Current Edition)

Obulesu M, Rao D M. Animal models of Alzheimer's disease: an understanding of pathology and therapeutic avenues. Int J. Neurosci. 2010 August; 120(8):531-7. Review.

Oddo S, Caccamo A, Shepherd J D, Murphy M P, Golde T E, Kayed R, Metherate R, Mattson M P, Akbari Y, LaFerla F M (2003). Triple-transgenic model of Alzheimer's disease with plaques and tangles: intracellular Abeta and synaptic dysfunction. Neuron 39: 409-421.

*Oligonucleotide Synthesis* (N. Gait, ed., Current Edition)

Ohno H, Stewart J, Fournier M C, Bosshart H, Rhee I, Miyatake S, Saito T, Gallusser A, Kirchhausen T, Bonifacino J S. (1995). Interaction of tyrosine-based sorting signals with clathrin-associated proteins. Science 269: 1872-5.

Ohshima T, Ogura H, Tomizawa K, Hayashi K, Suzuki H, Saito T, Kamei H, Nishi A, Bibb J A, Hisanaga S, Matsui H, Mikoshiba K. (2005). Impairment of hippocampal long-term depression and defective spatial learning and memory in p35 mice. J. Neurochem. 94: 917-25.

Pardo C A, Eberhart C G. The neurobiology of autism. Brain Pathol. 2007 October; 17(4):434-47.

Patel J, Mooslehner K A, Chan P M, Emson P C, Stamford J A. (2003). Presynaptic control of striatal dopamine neurotransmission in adult vesicular monoamine transporter 2 (VMAT2) mutant mice. J. Neurochem. 85: 898-910.

Payne H L. (2008). The role of transmembrane AMPA receptor regulatory proteins (TARPs) in neurotransmission and receptor trafficking. Mol Membr Biol. 25: 353-62.

Perry and Davies, OSAR: Quantitative Structure-Activity Relationships in Drug

Pickart, C M. (2001). Mechanisms underlying ubiquitination. Annu Rev Biochem. 70: 503-533.

Praefcke G J, Ford M G, Schmid E M, Olesen L E, Gallop J L, Peak-Chew S Y, Vallis Y, Babu M M, Mills I G, McMahon H T. (2004). Evolving nature of the AP2 alpha-appendage hub during clathrin-coated vesicle endocytosis. EMBO J. 23: 4371-83.

Putnam (1996), Am. J. Health Syst. Pharm. 53(2), 151-160, erratum at Am. J. Health Syst. Pharm. 53(3), 325

Qi Y, Wang J K, McMillian M, Chikaraishi D M. (1997). Characterization of a CNS cell line, CAD, in which morphological differentiation is initiated by serum deprivation. J. Neurosci. 17: 1217-25.

Rácz B, Blanpied T A, Ehlers M D, Weinberg R J. (2004). Lateral organization of endocytic machinery in dendritic spines. Nat. Neurosci. 7: 917-8.

Rachidi M, Lopes C. Mental retardation and associated neurological dysfunctions in Down syndrome: a consequence of dysregulation in critical chromosome 21 genes and associated molecular pathways. Eur J Paediatr Neurol. 2008 May; 12(3):168-82.

Rechsteiner, M. & Rogers, S. W. (1996). PEST sequences and regulation by proteolysis. Trends Biochem. Sci., 21: 267-271.

Ripka, New Scientist 54-57 (Jun. 16, 1988)

Rotivinen et al., Acta Pharmaceutical Fennica 97:159-166, 1988

Sambrook, et al. *Molecular Cloning: A Laboratory Manual* (Current Edition)

Schnell E, Sizemore M, Karimzadegan S, Chen L, Bredt D S, Nicoll R A. (2002). Direct interactions between PSD-95 and stargazin control synaptic AMPA receptor number. Proc Natl Acad Sci USA. 99: 13902-7.

Schlüter O M, Xu W, Malenka R C. (2006). Alternative N-terminal domains of PSD-95 and SAP97 govern activity-dependent regulation of synaptic AMPA receptor function. Neuron. 51: 99-111.

Scott D B, Michailidis I, Mu Y, Logothetis D, Ehlers M D. J. Neurosci. 2004 Aug. 11; 24(32):7096-109.

Segawa M, Nomura Y. Rett syndrome. Curr Opin Neurol. 2005 April; 18(2):97-104.

Shankar G M, Bloodgood B L, Townsend M, Walsh D M, Selkoe D J, Sabatini B L. (2007). Natural oligomers of the Alzheimer amyloid-beta protein induce reversible synapse loss by modulating an NMDA-type glutamate receptor-dependent signaling pathway. J. Neurosci. 27: 2866-75.

Shankar G M, Li S, Mehta T H, Garcia-Munoz A, Shepardson N E, Smith I, Brett F M, Farrell M A, Rowan M J, Lemere C A, Regan C M, Walsh D M, Sabatini B L, Selkoe D J. (2008). Amyloid-beta protein dimers isolated directly from Alzheimer's brains impair synaptic plasticity and memory. Nat. Med. 14: 837-842.

Shankar G M, Welzel A T, McDonald J M, Selkoe D J, Walsh D M. (2011). Isolation of low-n amyloid β-protein oligomers from cultured cells, CSF, and brain. Methods Mol. Biol. 670: 33-44.

Shimizu H, Hupp T R. Intrasteric regulation of MDM2. Trends Biochem Sci. 2003 July; 28(7):346-9.

Shughrue P J, Acton P J, Breese R S, Zhao W Q, Chen-Dodson E, Hepler R W, Wolfe A L, Matthews M, Heidecker G J, Joyce J G, Villarreal S A, Kinney G G. (2010). Anti-ADDL antibodies differentially block oligomer binding to hippocampal neurons. Neurobiol Aging 31: 189-202.

Shumway S D, Maki M, Miyamoto S. (1999). The PEST domain of IkappaBalpha is necessary and sufficient for in vitro degradation by mu-calpain. J Biol. Chem. 274: 30874-30881.

Snyder E M, Nong Y, Almeida C G, Paul S, Moran T, Choi E Y, Nairn A C, Salter M W, Lombroso P J, Gouras G K, Greengard P. (2005). Regulation of NMDA receptor trafficking by amyloid-beta. Nat. Neurosci. 8: 1051-1058.

Songyang et al., Cell 72:767-778, 1993

Spires-Jones T L, Meyer-Luehmann M, Osetek J D, Jones P B, Stern E A, Backsai B J, Hyman B T. (2007). Impaired spine stability underlies plaque-related spine loss in an Alzheimer's disease mouse model. Am J. Pathol. 171: 1304-1311.

Stein V, House D R, Bredt D S, Nicoll R A. (2003). Postsynaptic density-95 mimics and occludes hippocampal long-term potentiation and enhances long-term depression. J. Neurosci. 23: 5503-6.

Sun et al., *Cell Research* (2009) 19:612-624

Tabernero J, Dirix L, Schöffski P, Cervantes A, Lopez-Martin J A, Capdevila J, van Beijsterveldt L, Platero S, Hall B, Yuan Z, Knoblauch R, Zhuang S H. Clin Cancer Res. 2011 Oct. 1; 17(19):6313-21. Epub 2011 Aug. 10

Terry R D, Masliah E, Salmon D P, Butters N, DeTeresa R, Hill R, Hansen L A, Katzman R. (1991). Physical basis of cognitive alterations in Alzheimer's disease: synapse loss is the major correlate of cognitive impairment. Ann Neurol. 30: 572-80.

*Transcription and Translation* (B. Hames & S. Higgins, eds., Current Edition)

Ting J T, Kelley B G, Lambert T J, Cook D G, Sullivan J M. (2007). Amyloid precursor protein overexpression depresses excitatory transmission through both presynaptic and postsynaptic mechanisms. Proc Natl Acad Sci USA. 104: 353-358.

Townsend M, Shankar G M, Mehta T, Walsh D M, Selkoe D J. (2006). Effects of secreted oligomers of amyloid beta-protein on hippocampal synaptic plasticity: a potent role for trimers. J. Physiol. 572: 477-492.

Traub L M. (2009). Tickets to ride: selecting cargo for clathrin-regulated internalization. Nat Rev Mol Cell Biol. 10: 583-96.

Van Maerken T, Ferdinande L, Taildeman J, Lambertz I, Yigit N, Vercruysse L, Rihani A, Michaelis M, Cinatl J Jr, Cuvelier C A, Marine J C, De Paepe A, Bracke M, Speleman F, Vandesompele J. (2009). Antitumor activity of the selective MDM2 antagonist nutlin-3 against chemoresistant neuroblastoma with wild-type p53. J. Natl Cancer Inst. 101: 1562-1574.

Vanderklish P, Saido T C, Gall C, Arai A, Lynch G. (1995). Proteolysis of spectrin by calpain accompanies theta-burst stimulation in cultured hippocampal slices. Brain Res Mol Brain Res 32: 25-35.

Vinade L, Petersen J D, Do K, Dosemeci A, Reese T S. (2001). Activation of calpain may alter the postsynaptic density structure and modulate anchoring of NMDA receptors. Synapse 40: 302-9.

Wade M, Wang Y V, Wahl G M. (2010). The p53 orchestra: Mdm2 and Mdmx set the tone. Trends Cell Biol. 20: 299-309.

Walsh D M, Klyubin I, Fadeeva J V, Cullen W K, Anwyl R, Wolfe M S, Rowan M J, Selkoe D J. (2002). Naturally secreted oligomers of amyloid beta protein potently inhibit hippocampal long-term potentiation in vivo. Nature. 416: 535-539.

Walsh D M, Klyubin I, Shankar G M, Townsend M, Fadeeva J V, Betts V, Podlisny M B, Cleary J P, Ashe K H, Rowan M J, Selkoe D J. (2005). The role of cell-derived oligomers of Abeta in Alzheimer's disease and avenues for therapeutic intervention. Biochem Soc Trans. 33:1087-1090.

Wang H W, Pasternak J F, Kuo H, Ristic H, Lambert M P, Chromy B, Viola K L, Klein W L, Stine W B, Krafft G A, Trommer B L. (2002). Soluble oligomers of beta amyloid (1-42) inhibit long-term potentiation but not long-term depression in rat dentate gyrus. Brain Res. 924: 133-140.

Wei F Y, Tomizawa K, Ohshima T, Asada A, Saito T, Nguyen C, Bibb J A, Ishiguro K, Kulkarni A B, Pant H C, Mikoshiba K, Matsui H, Hisanaga S. (2005). Control of cyclin-dependent kinase 5 (Cdk5) activity by glutamatergic regulation of p35 stability. J. Neurochem. 93: 502-12.

Xia et al. (2002), Nature Biotechnol., 20(10), 1006-10 (viral-mediated delivery)

Xu W, Schliiter O M, Steiner P, Czervionke B L, Sabatini B, Malenka R C. Neuron. 2008 Jan. 24; 57(2):248-62.

Yasuda R P, Ikonomovic M D, Sheffield R, Rubin R T, Wolfe B B, Armstrong D M. (1995). Reduction of AMPA-selective glutamate receptor subunits in the entorhinal cortex of patients with Alzheimer's disease pathology: a biochemical study. Brain Res. 678: 161-167.

Young J W, Zhou X, Geyer M A. Animal models of schizophrenia. Curr Top Behav Neurosci. 2010; 4:391-433. Review.

Zhang et al., *JBC* (2007) 282:15778-89

Zhang S, Edelmann L, Liu J, Crandall J E, Morabito M A. (2008). Cdk5 regulates the phosphorylation of tyrosine 1472 NR2B and the surface expression of NMDA receptors. J. Neurosci. 28: 415-24.

Zhang F, Throm S L, Murley L L, Miller L A, Steven Zatechka D Jr, Kiplin Guy R, Kennedy R, Stewart C F. (2011). MDM2 antagonist nutlin-3a reverses mitoxantrone resistance by inhibiting breast cancer resistance protein mediated drug transport. Biochem Pharmacol. 82: 24-34.

We claim:

1. A method of improving one or more cognitive deficits in a subject with Alzheimer's disease (AD), comprising administering Nutlin-3 to the subject in an amount affective to reduce amyloid beta (Aβ)-induced α-Amino-3-hydroxy-5-methyl-4-isoxazolepropionic acid receptor (AMPAR) endocytosis in neuronal cells in the subject.

2. The method of claim 1, wherein the one or more cognitive deficits are selected from the group consisting of cognitive impairment, cognitive decline, memory loss and dementia.

3. The method of claim 1, wherein Nutlin-3 is administered to the subject in a pharmaceutical composition.

4. The method of claim 3, wherein the pharmaceutical composition is administered to the subject parenterally, intradermally, subcutaneously, transmucosally, orally or nasally.

5. The method of claim 4, wherein the pharmaceutical composition is administered to the subject orally.

* * * * *